US012800558B2

(12) United States Patent
Zhang et al.

(10) Patent No.: US 12,800,558 B2
(45) Date of Patent: Nov. 17, 2026

(54) METHOD FOR SCREENING PESTICIDE RESIDUES IN MEDICINE FOOD HOMOLOGY CHARACTERISTIC AGRICULTURAL PRODUCTS

(71) Applicant: Changchun Customs Technology Center, Changchun (CN)

(72) Inventors: Xun Zhang, Changchun (CN); Tao Liu, Changchun (CN); TingTing Hu, Changchun (CN); JiaHui Wang, Changchun (CN); Yao Fu, Changchun (CN); GuangYu Chen, Changchun (CN); XueSong Chen, Changchun (CN); Xue Jiang, Changchun (CN)

(73) Assignee: Changchun Customs Technology Center, Changchun (CN)

( * ) Notice: Subject to any disclaimer, the term of this patent is extended or adjusted under 35 U.S.C. 154(b) by 596 days.

(21) Appl. No.: 18/469,539

(22) Filed: Sep. 18, 2023

(65) Prior Publication Data

US 2024/0102976 A1 Mar. 28, 2024

(30) Foreign Application Priority Data

Sep. 23, 2022 (CN) ......................... 202211165456.4

(51) Int. Cl.
*G01N 30/72* (2006.01)
*G01N 30/02* (2006.01)
(Continued)

(52) U.S. Cl.
CPC ......... *G01N 30/7266* (2013.01); *G01N 30/60* (2013.01); *G16C 20/62* (2019.02);
(Continued)

(58) Field of Classification Search
CPC ............... G01N 30/7266; G01N 30/60; G01N 2030/3007; G01N 2030/027; G16C 20/64; G16C 20/62
See application file for complete search history.

(56) References Cited

FOREIGN PATENT DOCUMENTS

| | | | | |
|---|---|---|---|---|
| CN | 107817306 A | * 3/2018 | ............ | G01N 30/02 |
| CN | 111830141 A | * 10/2020 | ............ | G01N 30/06 |

(Continued)

OTHER PUBLICATIONS

Cn112326812a, Machine Translation (Year: 2021).*
(Continued)

*Primary Examiner* — Benjamin L Lebron
*Assistant Examiner* — Mahmoud Motaz Abdel Latif

(57) ABSTRACT

A method for screening pesticide residues in medicine food homology (MFH) characteristic agricultural products includes step 1, a liquid chromatography-mass spectrometry database of pesticides is constructed, standard solution are prepared for the pesticides and liquid chromatography and mass spectrometry are used to detect the standard solutions; step 2, a sample is processed and then is detected to obtain a liquid chromatography-mass spectrogram; step 3, the liquid chromatography-mass spectrogram obtained from step 2 and liquid chromatography-mass spectrograms in the liquid chromatography-mass spectrometry database obtained from step 1 are compared and analyzed individually. The advances are as follows: a high-resolution rapid method for no less than 300 pesticide residues has been established, the method has high qualitative accuracy, controls the probability of quality accidents to almost zero, and provides reliable technical support for customs supervision of import and export of the MFH agricultural products.

6 Claims, 30 Drawing Sheets

(51) Int. Cl.
*G01N 30/30* (2006.01)
*G01N 30/60* (2006.01)
*G16C 20/62* (2019.01)
*G16C 20/64* (2019.01)

(52) U.S. Cl.
CPC ....... *G16C 20/64* (2019.02); *G01N 2030/027* (2013.01); *G01N 2030/3007* (2013.01)

(56) References Cited

FOREIGN PATENT DOCUMENTS

| | | | | |
|---|---|---|---|---|
| CN | 112326812 A | * | 2/2021 | ............. G01N 30/34 |
| CN | 112924561 A | * | 6/2021 | ............. G01N 30/06 |
| WO | WO-2019200947 A1 | * | 10/2019 | ............. G01N 30/06 |

OTHER PUBLICATIONS

WO2019200947A1 Machine Translation (Year: 2019).*
Francesca Barbetti et al., "Pesticide residues screening and quantitation analysis in olive oil using an Orbitrap Exploris 240 HRMS." Thermo Fisher Scientific (Year: 2020).*
Cn112924561a, Machine Translation (Year: 2021).*
CN107817306A, Machine Translation (Year: 2018).*
"Understanding Gradient HPLC: An Excerpt from LCGC's e-Learning Tutorial on HPLC for Understanding Gradient HPLC at CHROMacademy.Com." LC GC Europe Jul. 1, 2013: 426. Print. (Year: 2013).*
CN111830141A, Machine Translation (Year: 2020).*

* cited by examiner

METHOD FOR SCREENING PESTICIDE RESIDUES IN MEDICINE FOOD HOMOLOGY CHARACTERISTIC AGRICULTURAL PRODUCTS

TECHNICAL FIELD

The disclosure relates to the technical field of pharmaceutical analysis, and particularly to a method for screening pesticide residues in medicine food homology (MFH) characteristic agricultural products.

BACKGROUND

MFH products are a health food produced based on the national catalog of medicinal food homology, which is between health products and medicines. The MFH products have both the therapeutic effect of medicines and the safety and stability of food. The MFH agricultural products include *ginseng, acanthopanax senticosus, epimedium*, and *Ganoderma lucidum.*

In recent years, safety issues related to the MFH products have been frequently exposed, among which poisoning incidents caused by excessive pesticide residues are particularly serious. There are many kinds of pesticides with different chemical structures and properties, as well as complex sample matrices, so methods for detecting the pesticides require precise operational means, high sensitivity, and strong specificity. At present, a multi-residue analysis technology is often used to detect agricultural and veterinary medicine residues in MFH agricultural products, but the detection items are numerous and the sample matrixes are complex. The main detection techniques used based on national, industry, and local standards are gas chromatography-mass spectrum/mass spectrometry and liquid chromatography-mass spectrum/mass spectrometry, and to ensure the specificity of the detection methods, a tandem mass spectrometry technology is often used. With the annual growth of Chinese bureau's detection business and the urgent need for safety detection of the MFH agricultural products at home and abroad, it is urgent to establish a fast and accurate screening and detection method for agricultural and veterinary medicine residues in food. The U.S. Food and Drug Administration (FDA) began research and development on high-resolution screening of pesticides in 2010. Due to the high selectivity of high-resolution mass spectrometry, the anti-interference ability is further enhanced, and it can be accurately and reliably applied to rapid screening and confirmation of target compounds related to food safety, as well as high sensitivity and high flux multi-residue analysis. With the annual growth of detection business of the MFH agricultural products exported from China, and the urgent need for safety detection of the MFH agricultural products at home and abroad, it is urgent to establish a rapid and accurate screening and detection method for pesticide residues in the MFH agricultural products.

SUMMARY

In order to establish a rapid and accurate detection method for pesticide residues in medicine food homology (MFH) agricultural products, the disclosure provides a method for screening pesticide residues in the MFH characteristic agricultural products.

The method for screening the pesticide residues in the MFH characteristic agricultural products includes the following steps:

step 1, a liquid chromatography-mass spectrometry database of pesticides is constructed. Standard solutions are prepared for the pesticides and liquid chromatography and mass spectrometry are used to detect the standard solutions, a detection condition of the liquid chromatography includes:

- a liquid chromatography column: an Accucore™ aQ C18 hydrophilic interaction liquid chromatography (HPLC) column, 150 millimeter (mm)×2.1 mm (internal diameter, i.d.), a particle size of 2.6 micrometer (μm);
- a mobile phase A: ammonium formate of 5 millimol per liter (mM) and a 0.1% formic acid aqueous solution;
- a mobile phase B: ammonium formate of 5 Mm and a 0.1% formic acid methanol solution
- a column temperature: 25° C., and a detection condition of the mass spectrometry includes:

- an ion source: an electrospray ionization;
- a temperature of the ion source: 325° C.;
- a temperature of a heater: 350° C.;
- a sheath gas flow rate: 40 atmospheres relative to vacuum (arb);
- an aux gas flow rate: 10 arb, step 2, a sample is processed to obtain a processed sample, and the processed sample is detected to obtain a liquid chromatography-mass spectrogram of the processed sample;

step 3, the liquid chromatography-mass spectrogram obtained from step 2 and the liquid chromatography-mass spectrograms in the liquid chromatography-mass spectrometry database obtained from step 1 are compared and analyzed individually.

The liquid chromatography-mass spectrometry database includes: names of compounds, molecular formulas of the compounds, accurate masses of the compounds, retention times of the compounds and accurate masses of characteristic ion fragments.

The pesticides in step 1 includes acephate, acetamiprid, aminocarb, azamethiphos, benalaxyl, bendiocarb, benfuracarb, bensulide, benzoximate, bifenazate, bupirimate, butafenacil, butoxycarboxim, buturon, carpropamid, carbaryl, carbendazim, carbetamide, carbofuran, carboxin, clethodim, clothianidin, cyazofamid, cycloxydim, cyprodinil, desmedipham, dicrotophos, diethofencarb, dimethoate, dinotefuran, dioxycarb, ethiofencarb, ethirimol, ethofumesate, fenazaquin, fenhexamid, fenobucarb, fenoxycarb, fenpropidine, flufenacet, fuberidazole, furalaxyl, furathiocarb, hexythiazox, hydramethylnon, imidachloprid, indoxacarb, isoprocarb, mefenacet, mepanipyrim, mepronil, metalaxyl, methamidophos, methomyl, methoxyfenozide, m-tolyl methylcarbamate, metribuzin, napropamide, nitenpyram, nuarimol, omethoate, oxamyl, pencycuron, primicarb, propamocarb, propargite, propoxur, prosulfocarb, pyrimethanil, quinoxyfen, rotenone, spirodiclofen, tebufenozide, tebutam, temephos, thiabendazole, thiacloprid, thiamethoxam, thiobencarb, thiodicarb, thiophanate-methyl, trichlorfon, vamidothion, ametryn, atrazine, azoxystrobin, benodanil, benoxacor, bitertanol, boscalid, buprofezin, butylate, chlorfluazuron, cumyluron, cyanazine, cycluron, cyproconazole, cyromazine, diclobutrazole, diflufenican, dimepiperate, dimethametryn, dimethenamid, dimethomorph, diniconazole, diphenamid, dipropetryn, diuron, dodemorph, epoxiconazole, ethiprole, etobenzanid, fenbuconazole, fenpropathrin, fenpropimorph, fenpyroximate, fenuron, flufenoxuron, fluometuron, flurtamone, flusilazole, flutolanil, flutriafol, forchlorfenuron, imazalil, imibenconazole, isoproturon, linuron, metconazole, methabenzthiazuron, methoprotryne, metobromuron, metoxuron, monolinuron, myclobutanil, neburon, paclobutrazole, penconazole, phenmedipham, picoxystrobin, prochloraz, prometon, prometryne, propazine, propiconazole, pymetrozine, pyraclostrobin, pyriproxyfen, sebutylazine, secbumeton, simeconazole, simetryn, tebuconazole, tebuthiuron, terbuthylazine, terbumeton, terbutryne, tetraconazole, thenylchlor, triadimefon, triadimenol, tridemorph, trifloxystrobin, triticonazole, acetochlor, alachlor, allidochlor, butachlor, butralin, chlordimeform, dazomet, dinitramine, diphenylamine, dithiopyr, fenoxanil, florasulam, flumetsulam, haloxyfop-2-ethoxyethyl, hexazinone, isopropalin, isoprothiolane, isoxaben, metazachlor, metolachlor, metosulam, metamitron, norflurazon, ofurace, picolinafen, pretilachlor, propachlor, propanil, propisochlor, prosulfocarb, pyrifenox, pyroquinolone, tepraloxydim, thiazopyr, tralkoxydim, allethrin, anilofos, aspon, bromfenvinfos, cadusafos, chlorpyrifos, coumaphos, crufomate, cycloate, cyphenothrin, defoliant, demeton-S-methyl, demeton-S-methylsulphone, dichlorvos, ditalimfos, eradicane, ethion, etrimfos, famphur, fenamiphossulfone, fenamiphos metabolite, fensulfothion, fenthion, fenthionsulfone, fenthionsulfoxide, heptenephos, iprobenfos, isazofos, isocarbamid, malathion, molinate, pebulate, phenthoate, phorate, phosalone, phosphamidon, phoxim, piperophos, pirimiphos-methyl, profenofos, propetamphos, pyraclofos, pyrazophos, pyridaphenthion, quinalphos, resmethrin, tebupirimfos, terbufos, terbufos sulfone, tetrachlorvinphos, tolclofos-methyl, triazophos, trietazine, vernolate, chloridazon, flumiclorac-pentyl, imazamethabenz-methyl, benzothiadiazole, butocarboxim, piperonyl-butoxide, propham, fludioxonil, hexaflumuron, fluorourea, cyclanilide, nitralin, terbacil, chlorthiophos, cypermethrin, demeton, phorate sulfoxide, thiometon, imazaquin, chlorpyrifos-methyl, benzoylprop, thifensulfuron-methyl, chlortoluron, trimethacarb, clomazone, bromuconazole (cis), mecarbam, propaquizafop, aldicarb, aldicarb sulfoxide, atratone, deethylatrazine, azinphos-ethyl, aziprotryn, benzofenap, bioallethrin, bioresmethrin, sulprofos, bromacil, brompyrazon, chlorimuron, cycocel, chlorpoxime, chlorsulfuron, cinidon-ethyl, cinosulfuron, coumatetralyl, cyclosulfamuron, cythioate, diethyltoluamide, desmetryne, dialifos, diallate, dichlofenthion, dichlofluanid, dichlorobenzamide, dicyclohexyl phthalate, dimefox, dimethirimol, dimethyl phthalate, dioxabenzofos, disulfoton-sulfone, dimethylbenzenesulfonamide, dodine, emamectin benzoate-Bla, emamectin benzoate-B1b, etaconazole, ethiofencarb-sulfoxide, ethoprophos, ethoxysulfuron, ethylene thiourea, ofurace, fentrazamide, flamprop-isopropyl, flamprop-methyl, fluazifop-butyl, fluazuron, flubenzimine, flurochloridone, fluridone, fluthiacet, fonofos, furmecyclox, azinphos-methyl, pyrflumetoclోprid, imazapic, imazethapyr, isofenphos, isomethiozin, isouron, kadethrin, kresoxim-methyl, malaoxon, mefenpyr-diethyl, mephosfolan, mefenoxam, methfuroxam, paraoxon-methyl, monalide, monuron, naptalam, nicotine, oxycarboxin, oxydemeton-methyl, phorate-sulfone, phosfolan, pirimiphos-ethyl, propyzamide, propylenethiourea, pyrazosulfuron methyl, pyrethrin 1, pyributicarb, pyriftalid, pyrimidifen, pyrithiobac-sodium, quinoclamine, quizalofop, rabenzazole, simeton, pleocidin A, pleocidin D, tabatrex, sulfotepp, tau-fluvalinate, tetraethyl diphosphate, terbucarb, thiofanox sulfoxide, thionazin, thiophanate, triallate, triazoxide, tri-n-butyl phosphate, tri-iso-butyl phosphate, uniconazole, vamidothion sulfone and/or sulfallate.

A flow rate of the liquid chromatography is a range of 0.35-0.45 milliliters per minute (mL/min). And a condition of gradient elution is as follows: an initial proportion of the mobile phase A is 100%, the initial proportion of the mobile phase A gradually decreases to a first proportion of 80% within 4 minutes, the first proportion gradually decreases to a second proportion of 60% within 1.5 minutes, the second proportion gradually decreases to a third proportion of 0% within 4 minutes, following by remaining for 2.4 minutes, and then the third proportion gradually increases to the initial proportion of 100%.

The flow rate of the liquid chromatography is 0.4 mL/min.

A scanning range of the mass spectrometry includes: 100-900 mass-to-charge ratios (M/Z) in a positive ion mode, or 100-700 M/Z in a negative ion mode.

A resolution of the liquid mass spectrometry includes: 70000 in full mass spectrometry scanning, or 17500 in tandem mass spectrometry (MS/MS).

The method for screening the pesticide residues in the MFH characteristic agricultural products includes: step 1, the liquid chromatography-mass spectrometry database of pesticides is constructed. The standard solutions are prepared for the pesticides and the liquid chromatography and the mass spectrometry are used to detect the standard solutions; step 2, the sample is processed to obtain a processed sample, and the processed sample is detected to obtain a liquid chromatography-mass spectrogram of the processed sample; step 3, the liquid chromatography-mass spectrogram obtained from step 2 and the liquid chromatography-mass spectrograms in the liquid chromatography-mass spectrometry database obtained from step 1 are compared and analyzed. The advances of the method are as follows: a high-resolution rapid screening method for no less than 300 pesticide residues is established. the method further enhances anti-interference ability of the detection due to the high selectivity of high-resolution mass spectrometry and can be accurately and reliably applied to the rapid screening and confirmation of non-target compounds related to the safety of the MFH agricultural products, as well as high sensitivity and high-throughput multi residue analysis. The method has high qualitative accuracy and controls the probability of quality accidents to almost zero, providing a reliable technical support for the supervision of imported and exported the MFH agricultural products by customs.

DETAILED DESCRIPTION OF EMBODIMENTS

Embodiment 1

Figure 1:
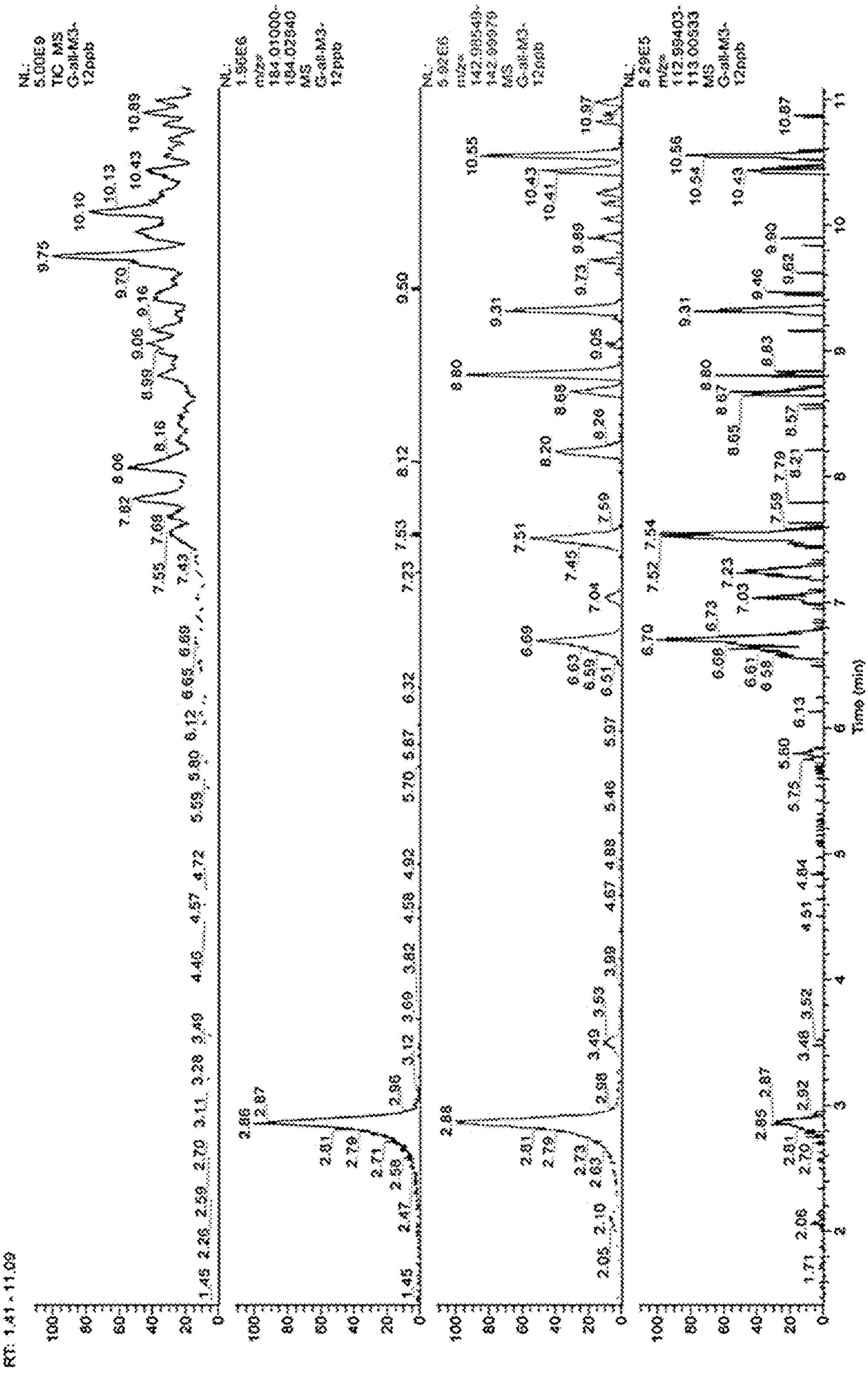
FIG. 1 is a chromatogram of acephate standard in a full-scan mass spectrometry/data-dependent tandem mass spectrometry (MS/ddMS$^2$) mode.
Figure 2:
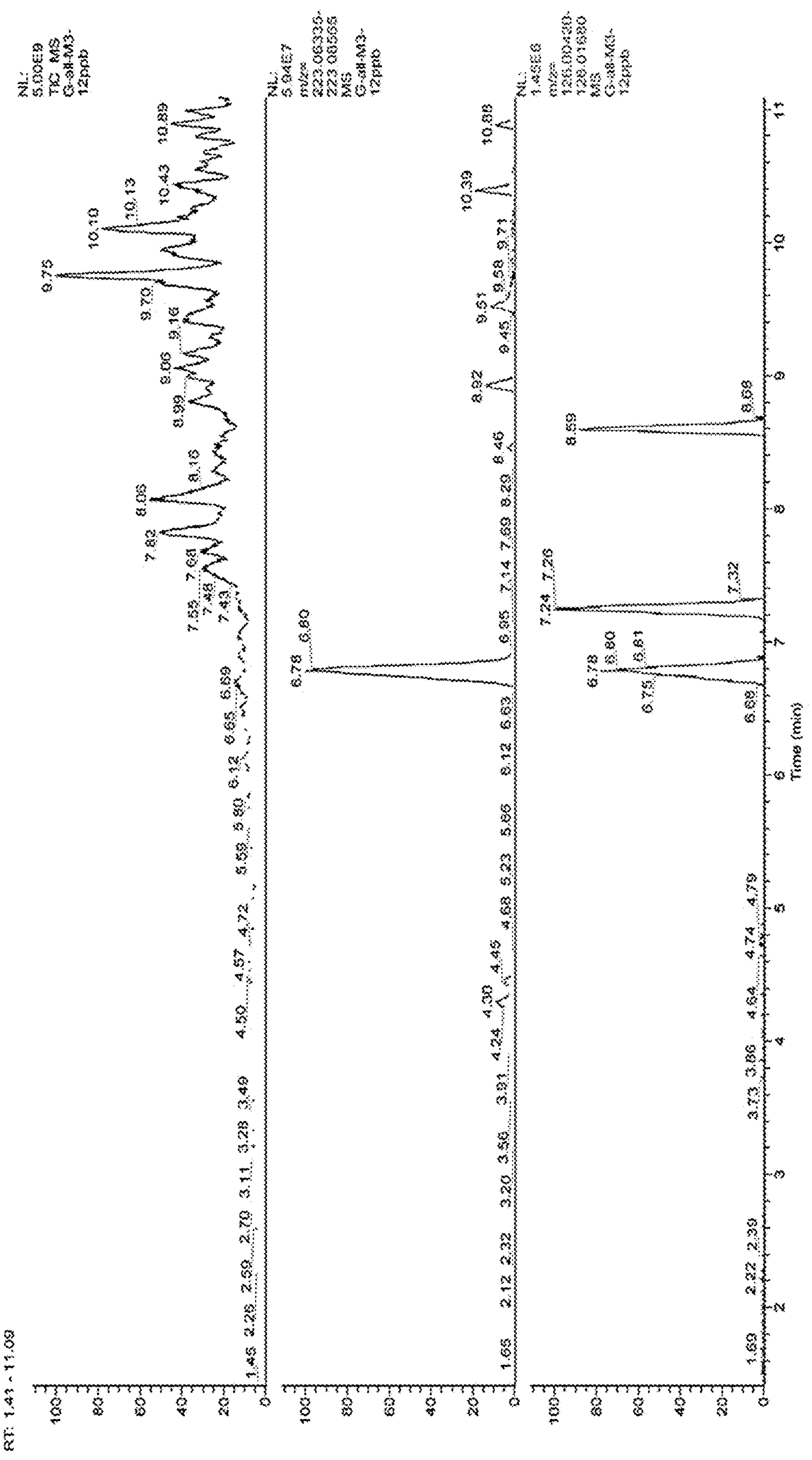
FIG. 2 is a chromatogram of acetamiprid standard in a full MS/ddMS$^2$ mode.
Figure 3:
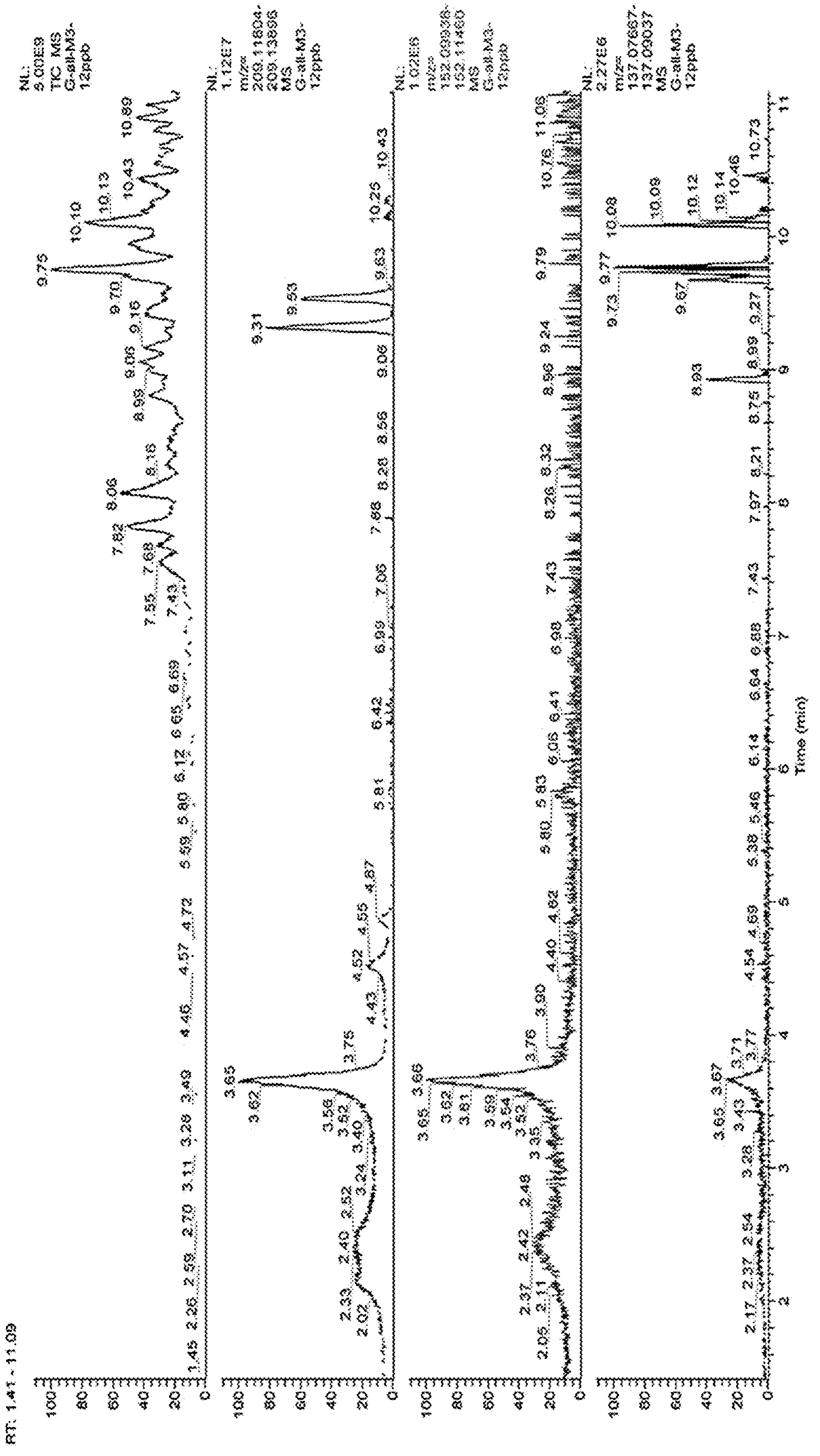
FIG. 3 is a chromatogram of aminocarb standard in a full MS/ddMS$^2$ mode.
Figure 4:
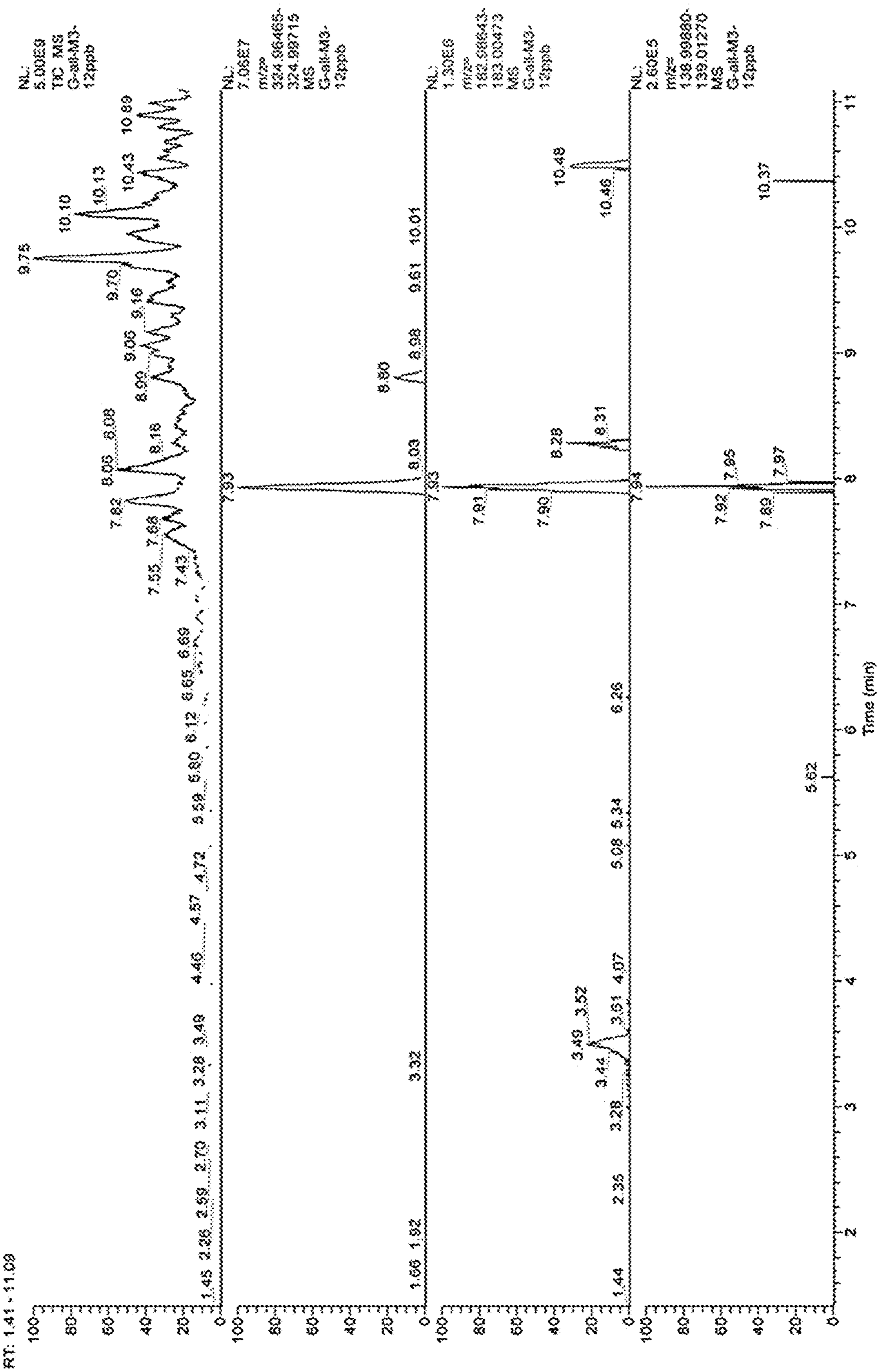
FIG. 4 is a chromatogram of azamethiphos standard in a full MS/ddMS$^2$ mode.
Figure 5:
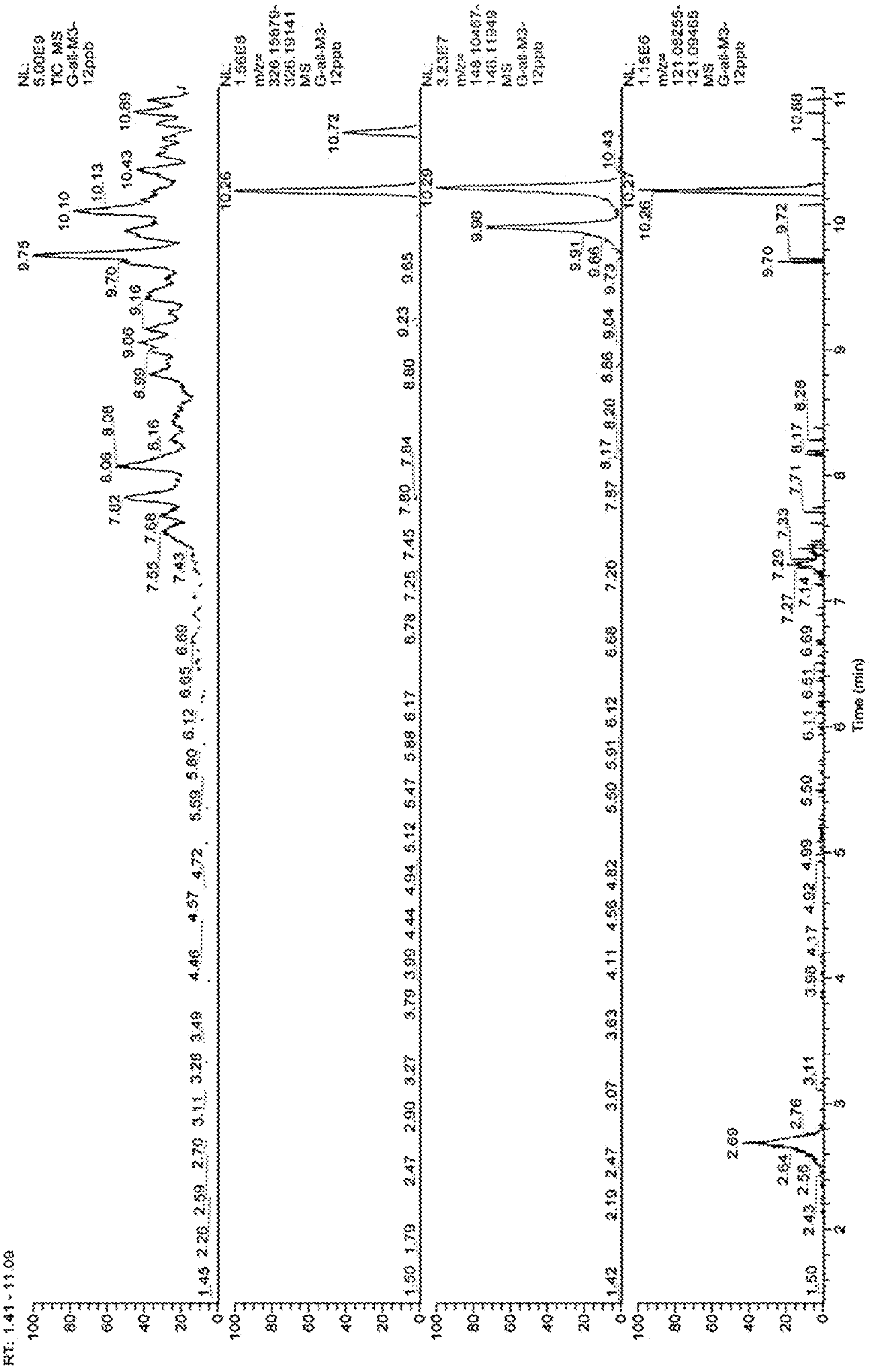
FIG. 5 is a chromatogram of benalaxyl standard in a full MS/ddMS$^2$ mode.
Figure 6:
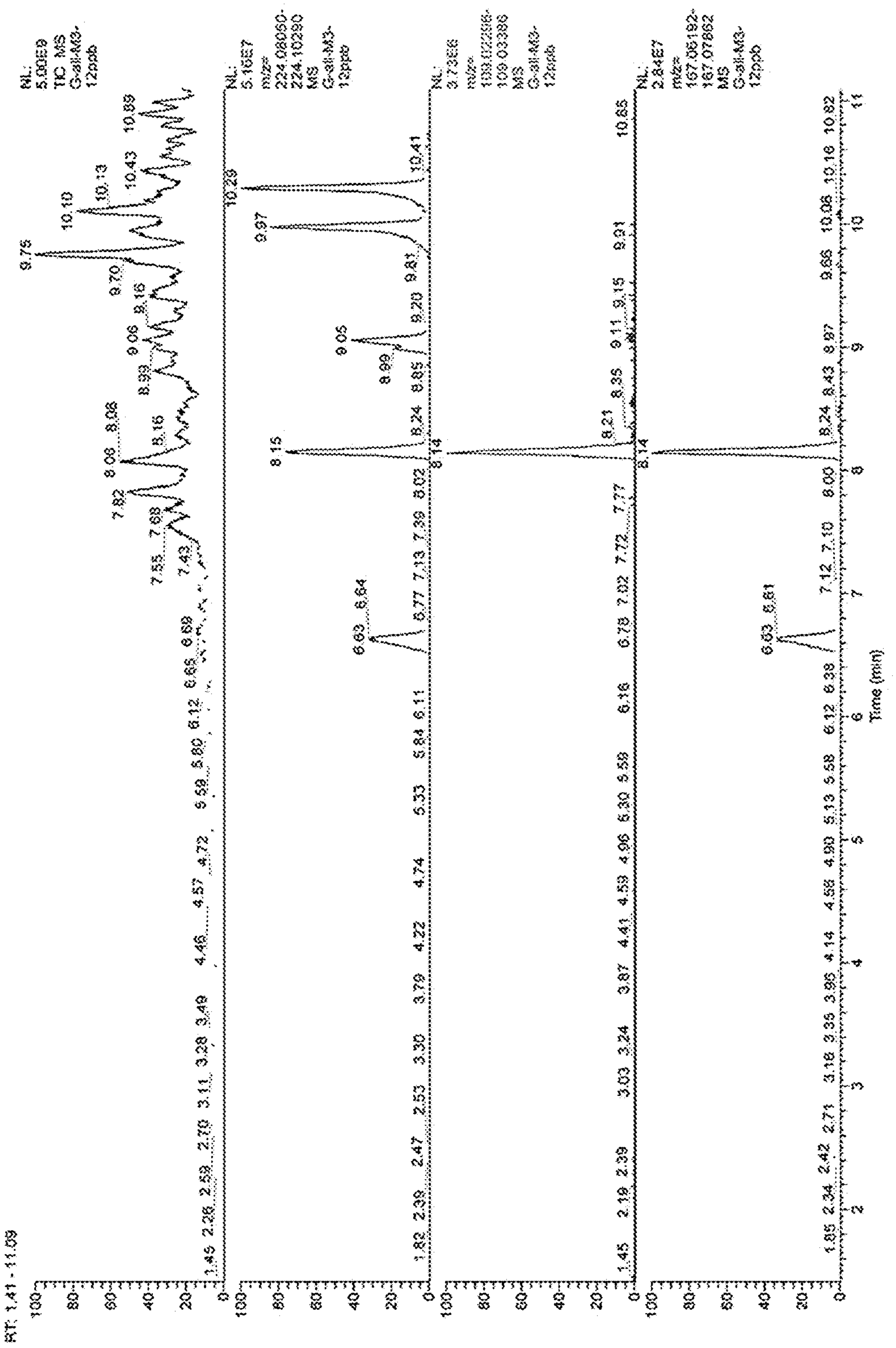
FIG. 6 is a chromatogram of bendiocarb standard in a full MS/ddMS$^2$ mode.
Figure 7:
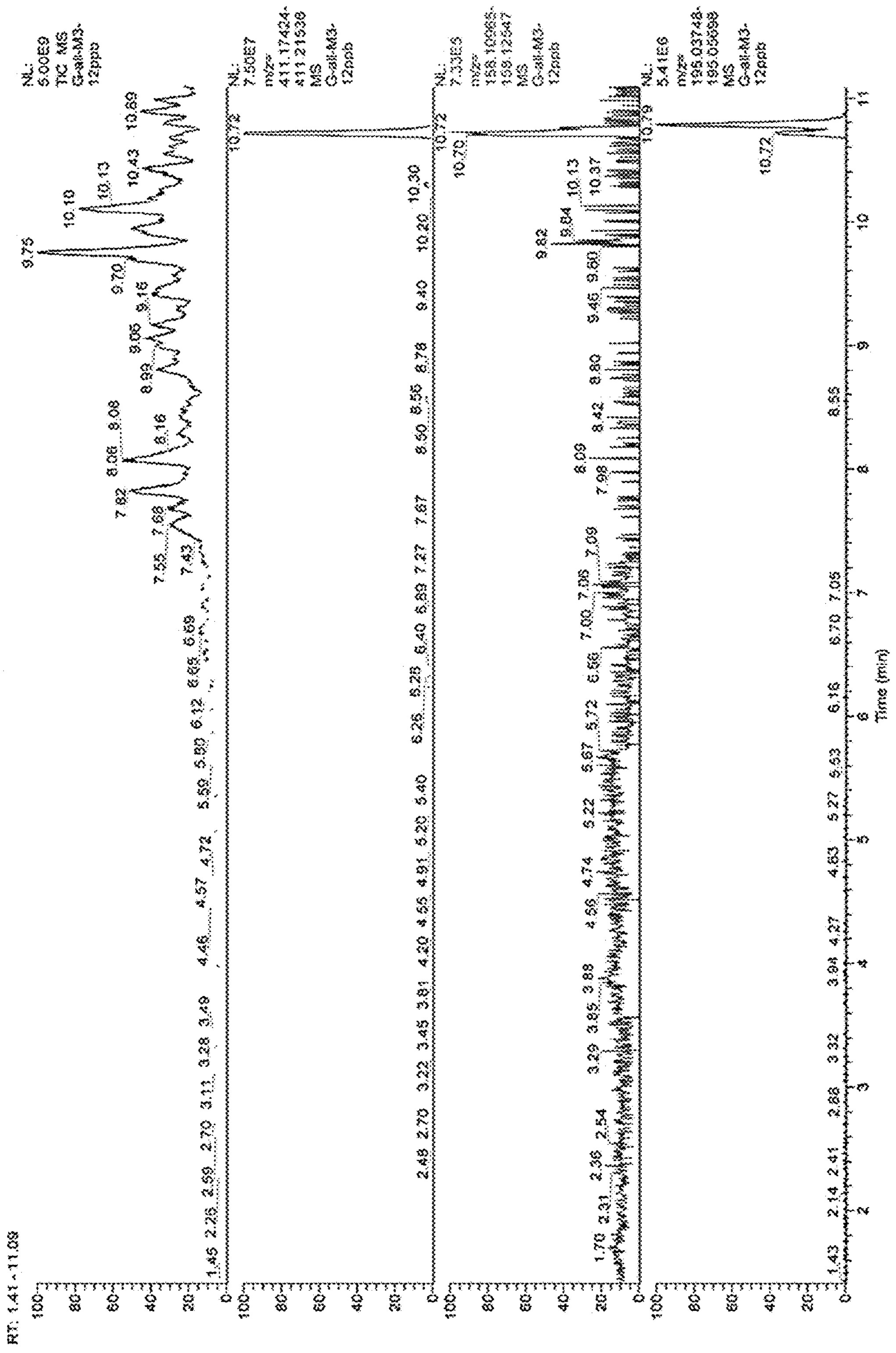
FIG. 7 is a chromatogram of benfuracarb standard in a full MS/ddMS$^2$ mode.
Figure 8:
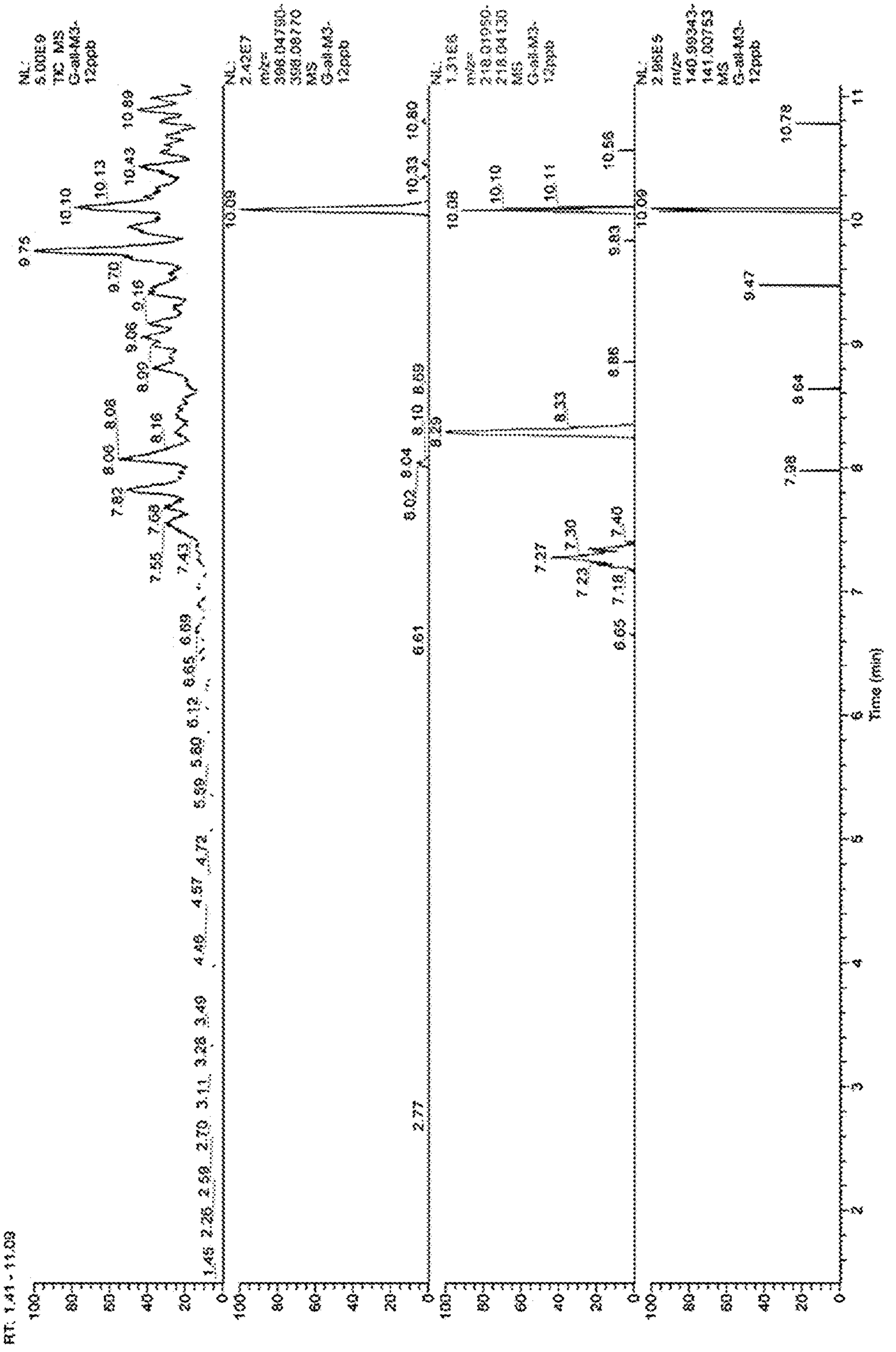
FIG. 8 is a chromatogram of bensulide standard in a full MS/ddMS$^2$ mode.
Figure 9:
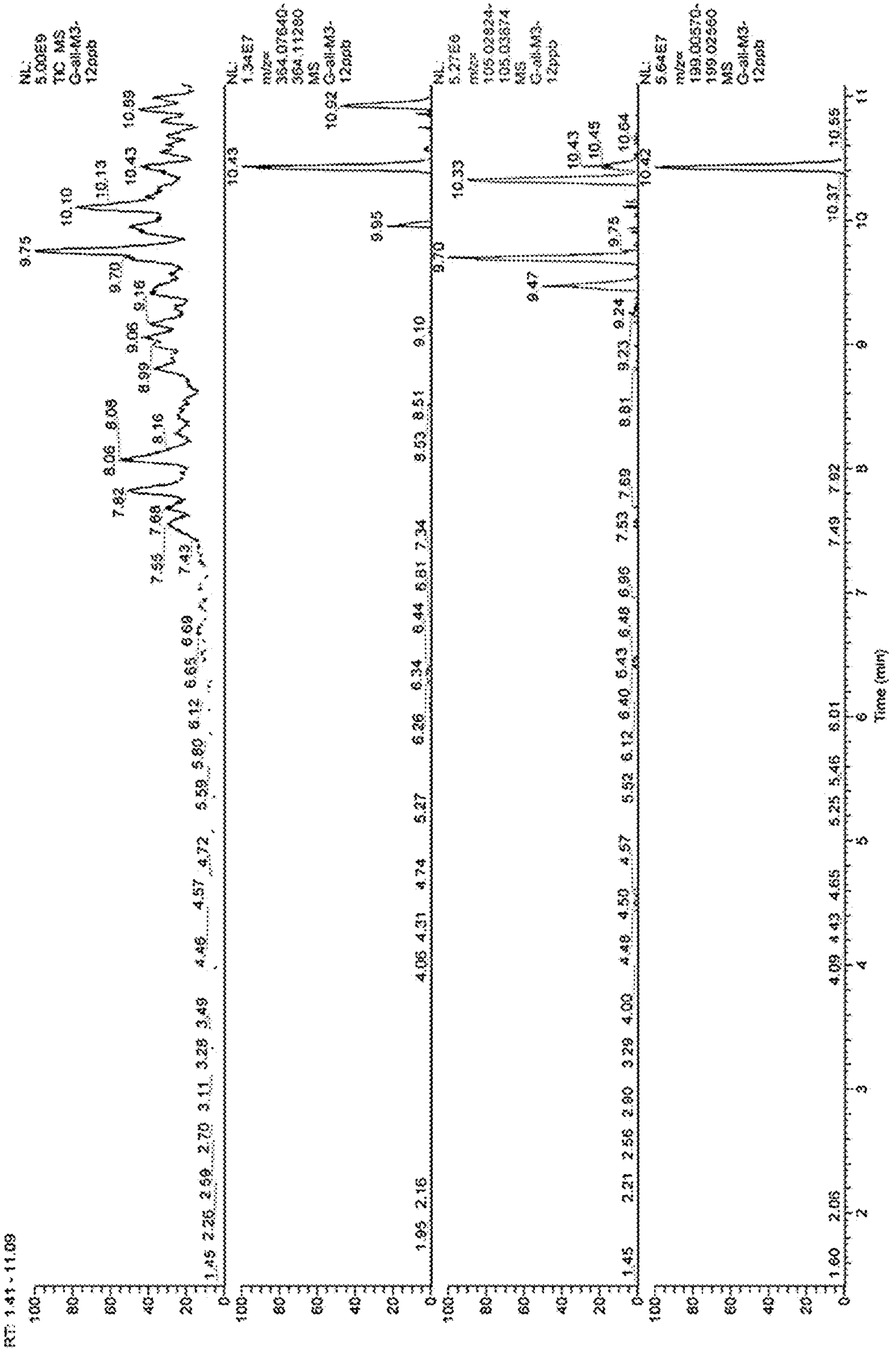
FIG. 9 is a chromatogram of benzoximate standard in a full MS/ddMS$^2$ mode.
Figure 10:
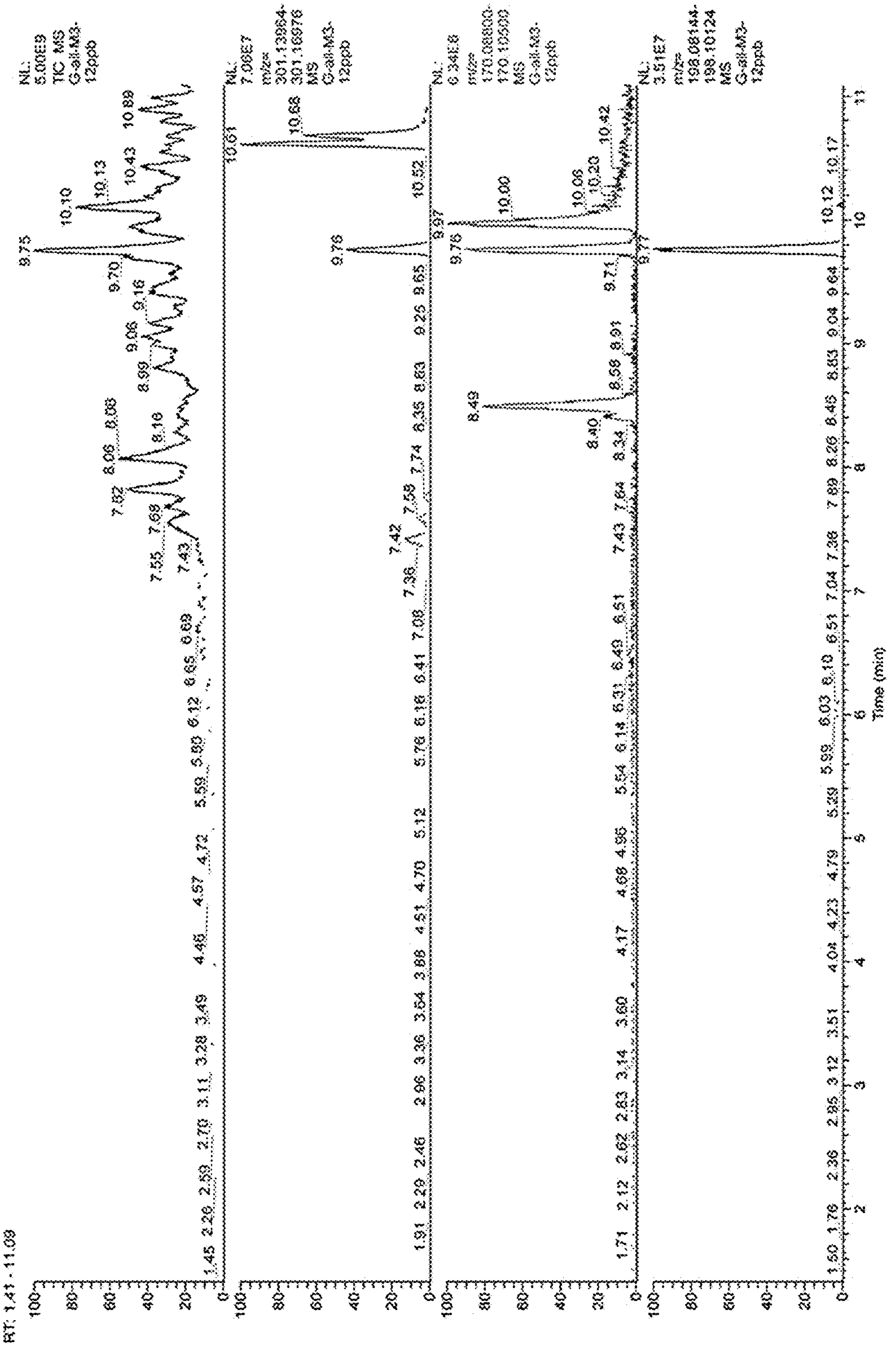
FIG. 10 is a chromatogram of bifenazate standard in a full MS/ddMS$^2$ mode.
Figure 11:
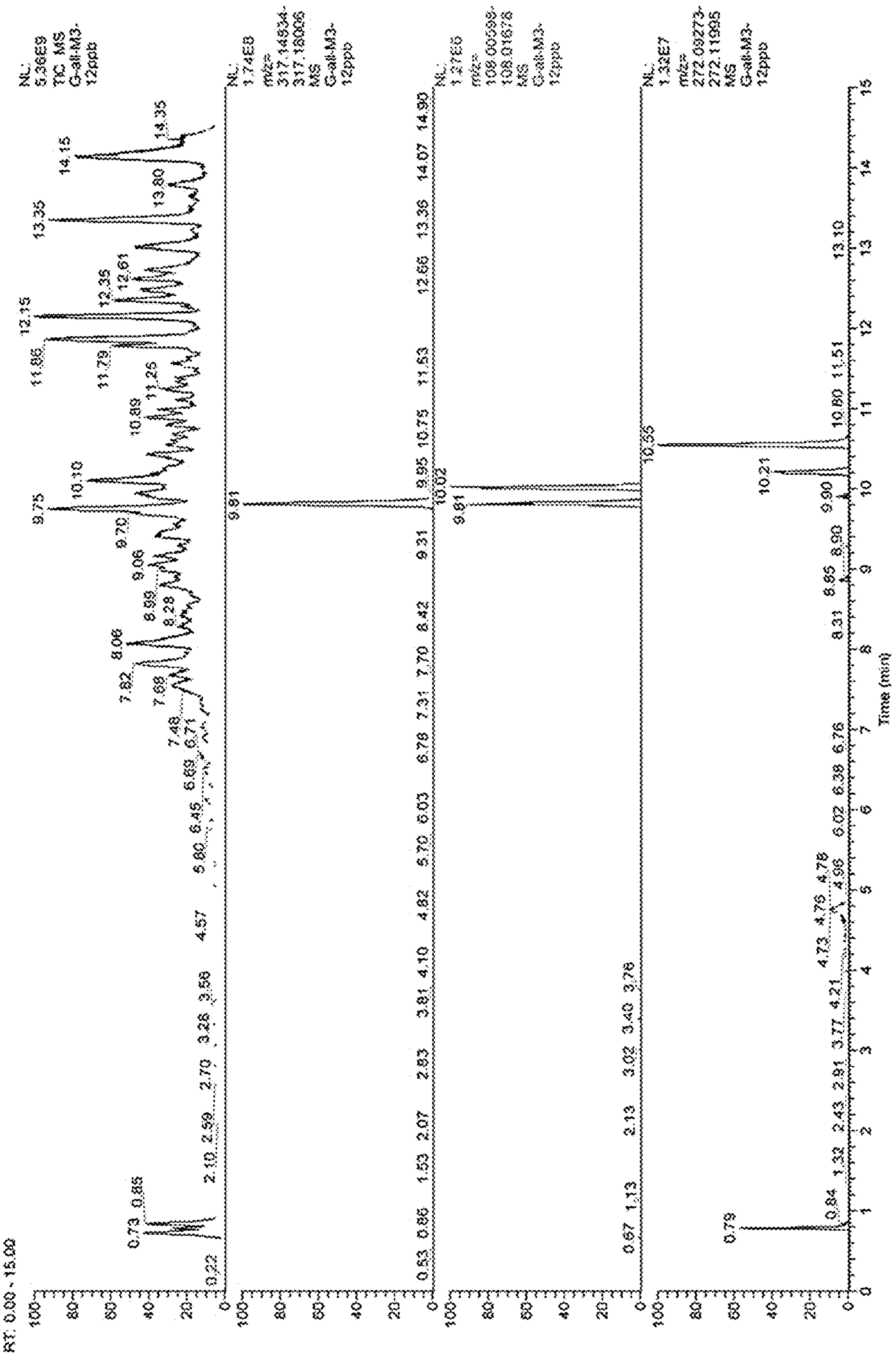
FIG. 11 is a chromatogram of bupirimate standard in a full MS/ddMS$^2$ mode.
Figure 12:
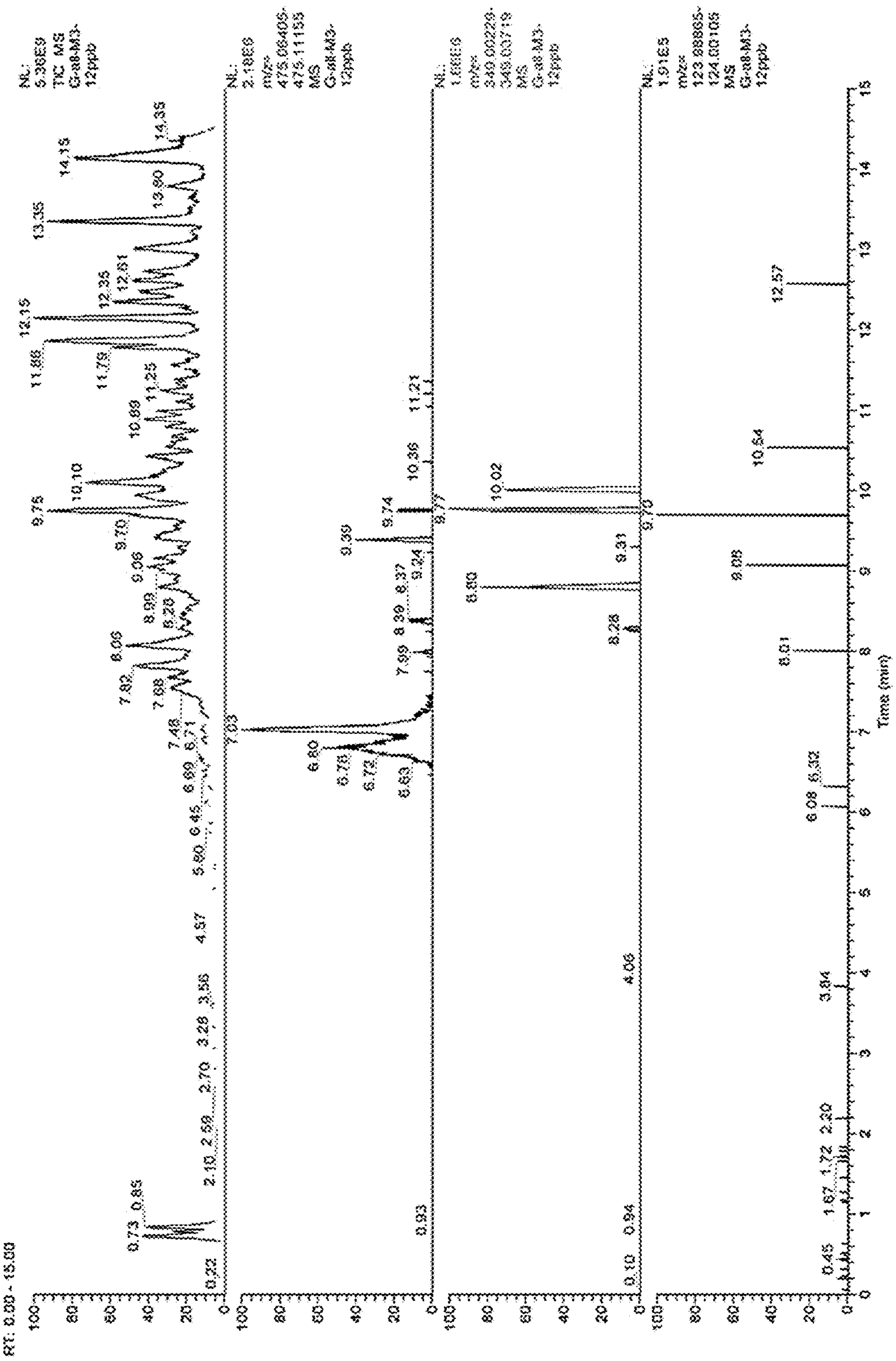
FIG. 12 is a chromatogram of butafenacil standard in a full MS/ddMS$^2$ mode.
Figure 13:
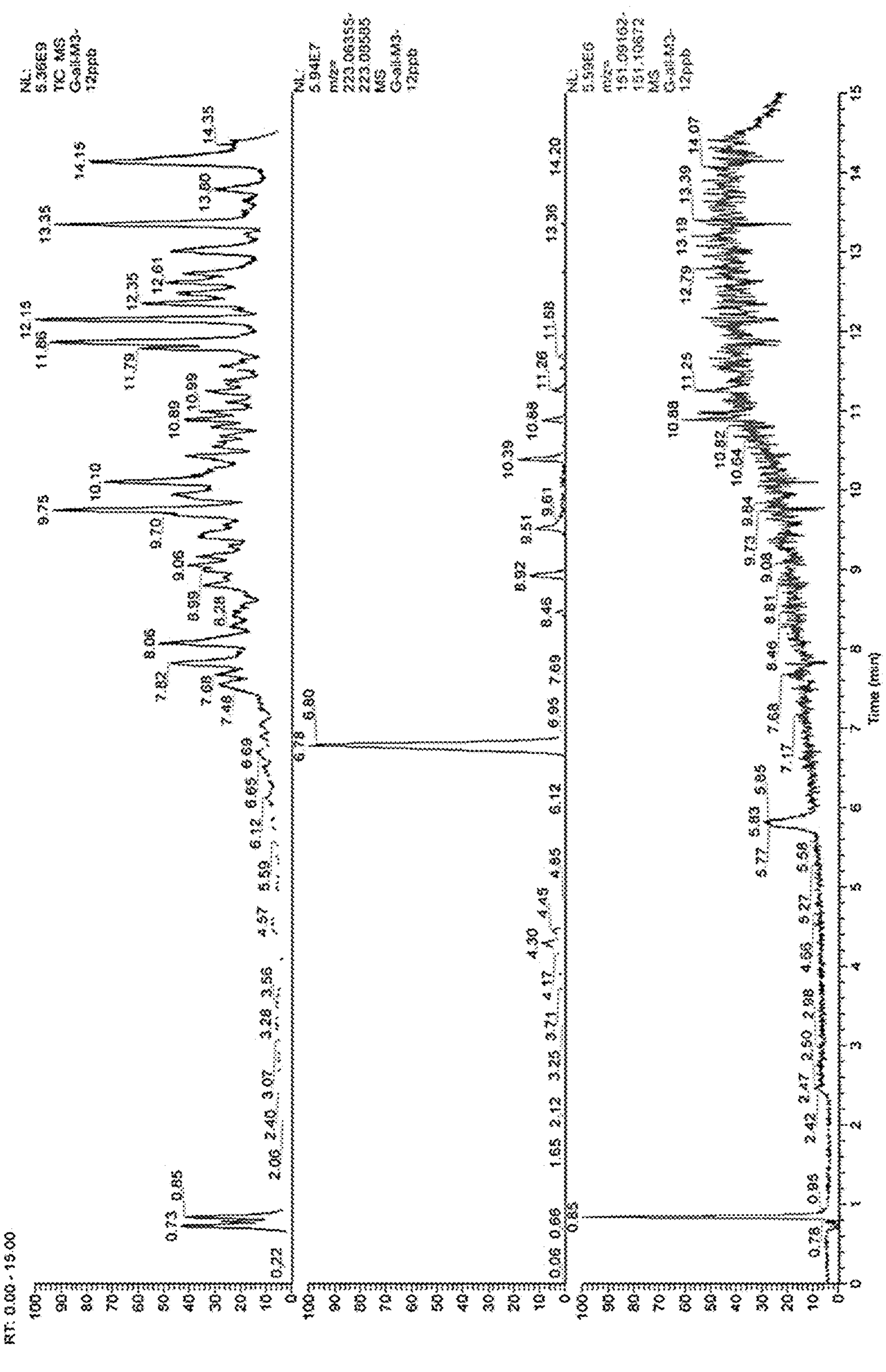
FIG. 13 is a chromatogram of butoxycarboxim standard in a full MS/ddMS$^2$ mode.
Figure 14:
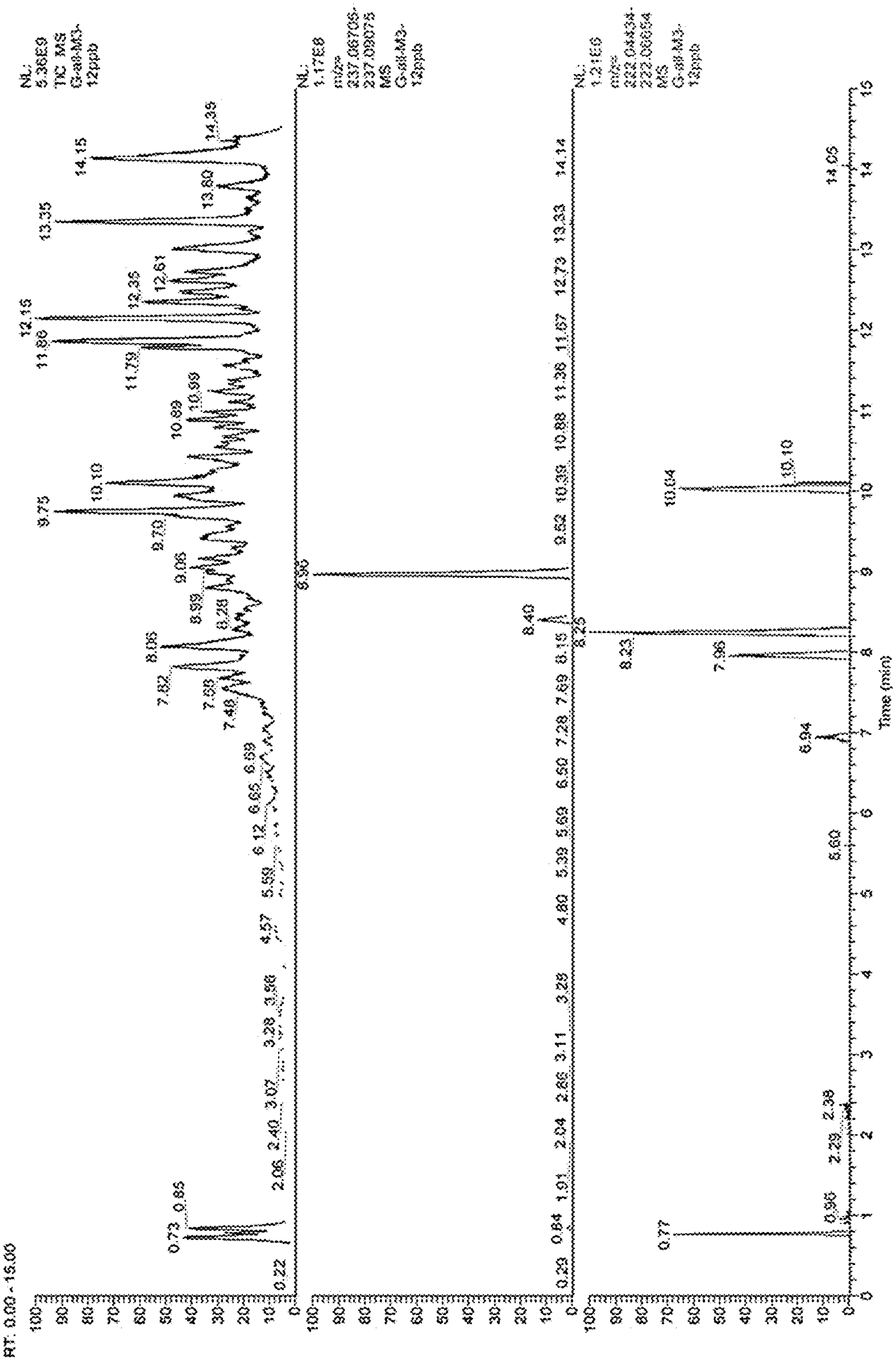
FIG. 14 is a chromatogram of buturon standard in a full MS/ddMS$^2$ mode.
Figure 15:
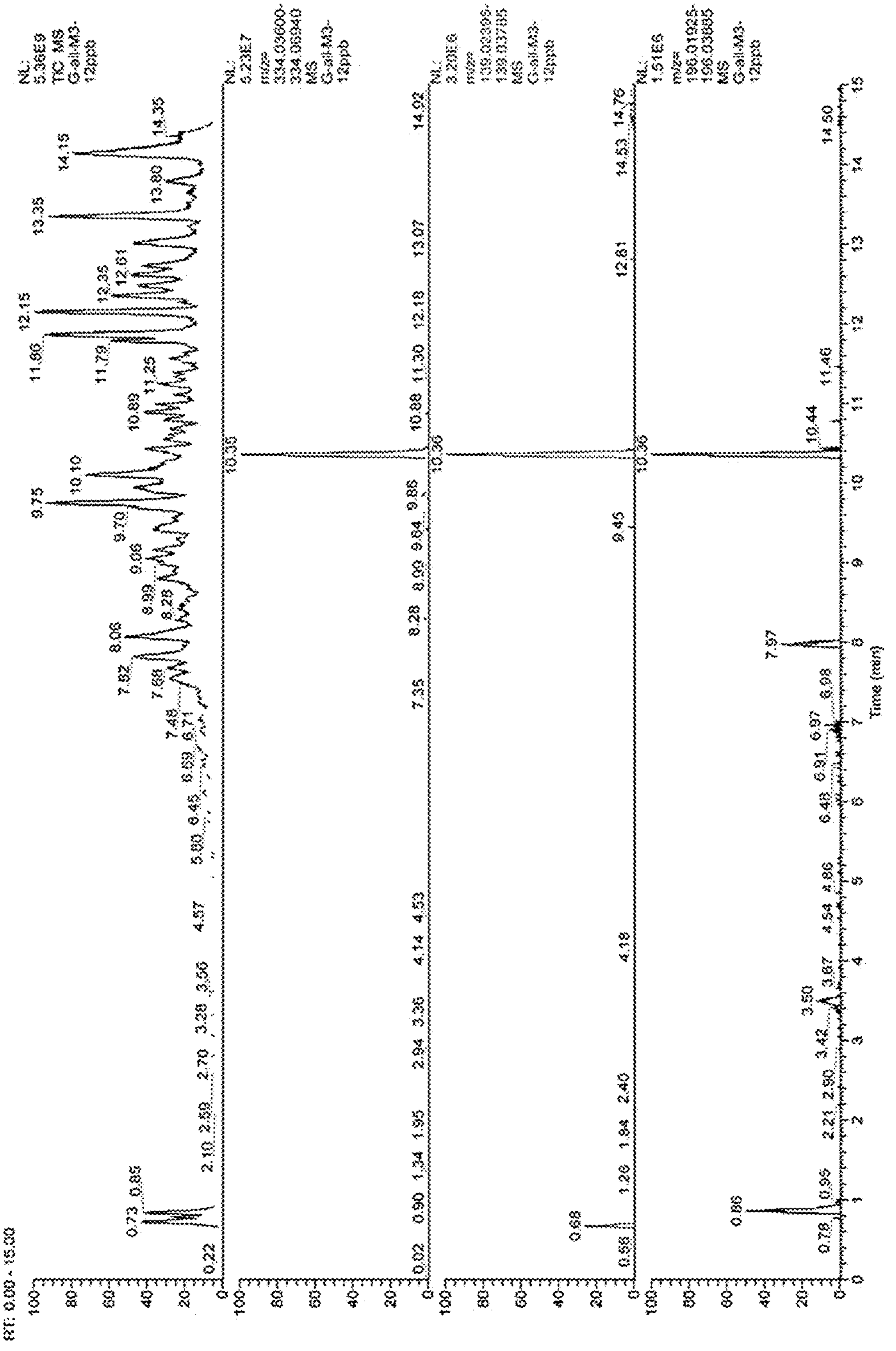
FIG. 15 is a chromatogram of carpropamid standard in a full MS/ddMS$^2$ mode.
Figure 16:
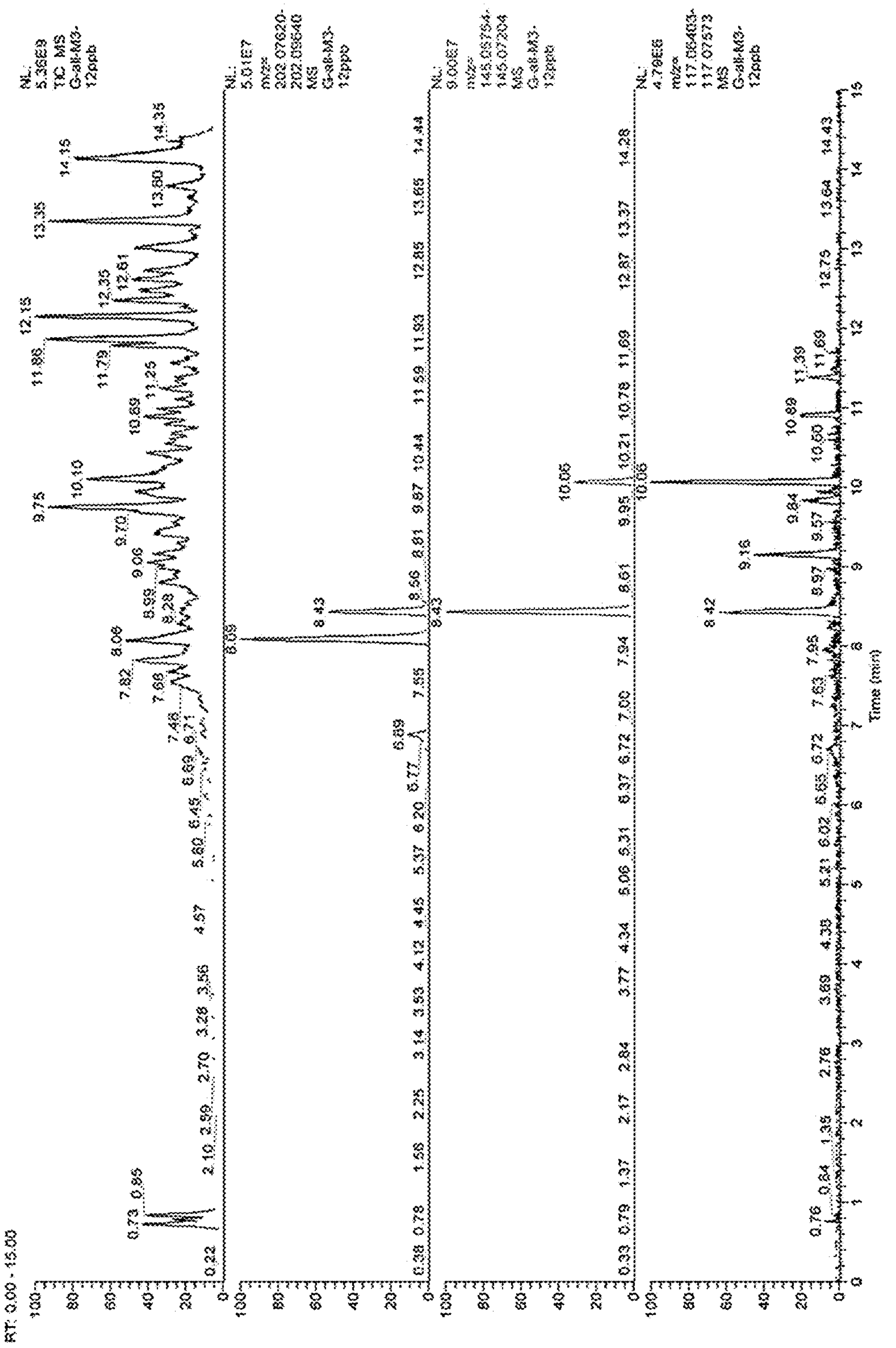
FIG. 16 is a chromatogram of carbaryl standard in a full MS/ddMS$^2$ mode.
Figure 17:
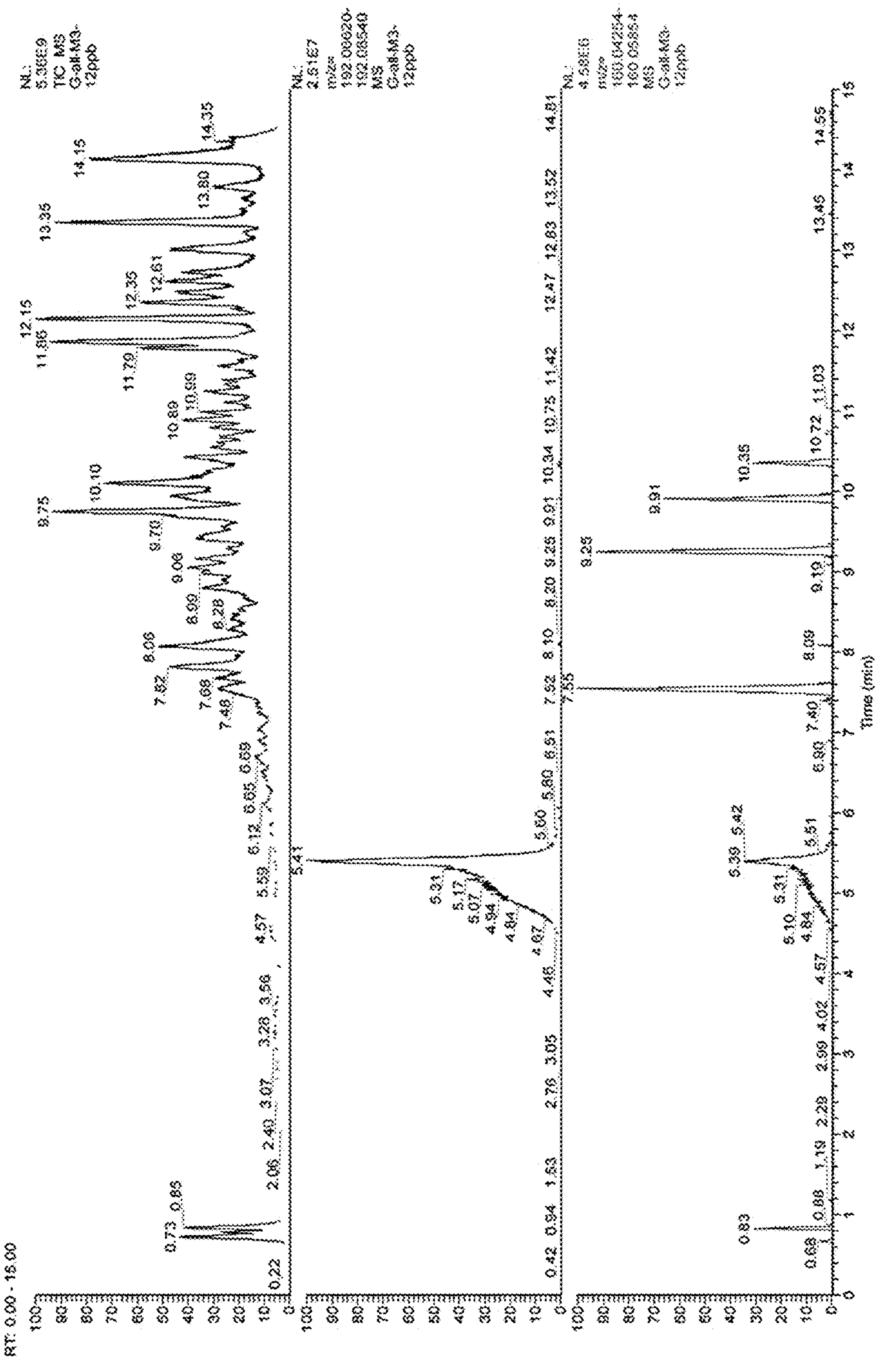
FIG. 17 is a chromatogram of carbendazim standard in a full MS/ddMS$^2$ mode.
Figure 18:
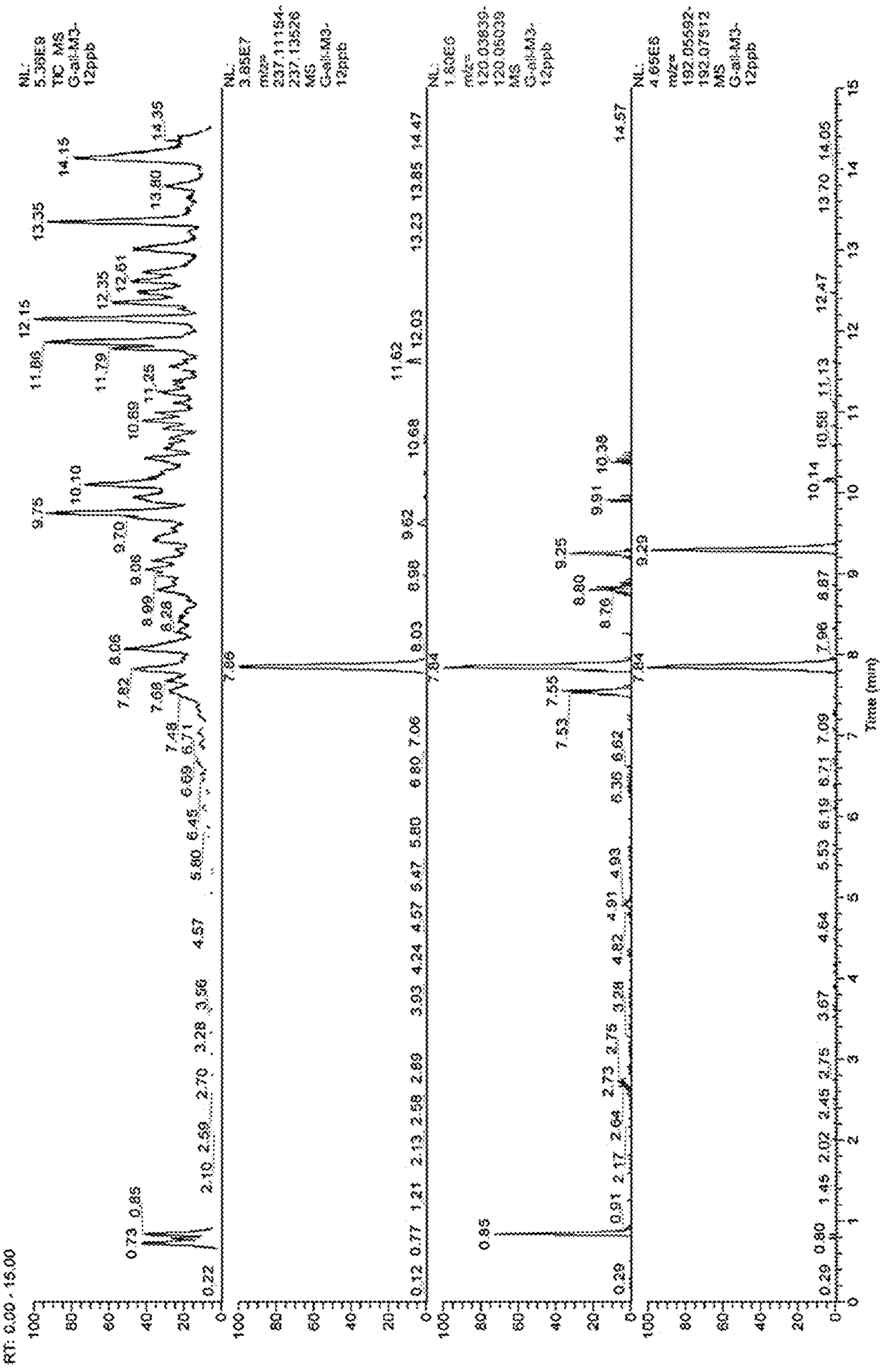
FIG. 18 is a chromatogram of carbetamide standard in a full MS/ddMS$^2$ mode.
Figure 19:
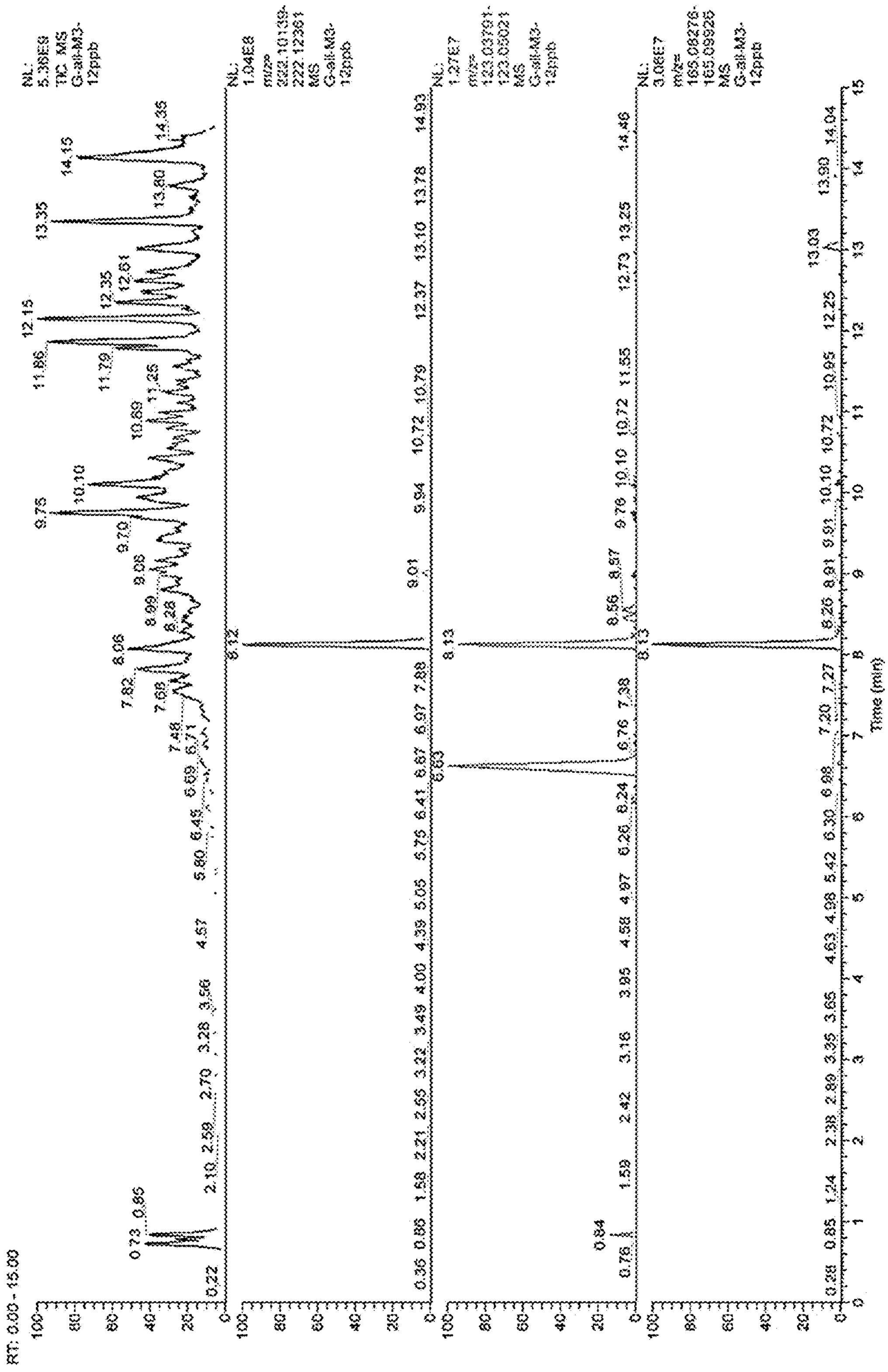
FIG. 19 is a chromatogram of carbofuran standard in a full MS/ddMS$^2$ mode.
Figure 20:
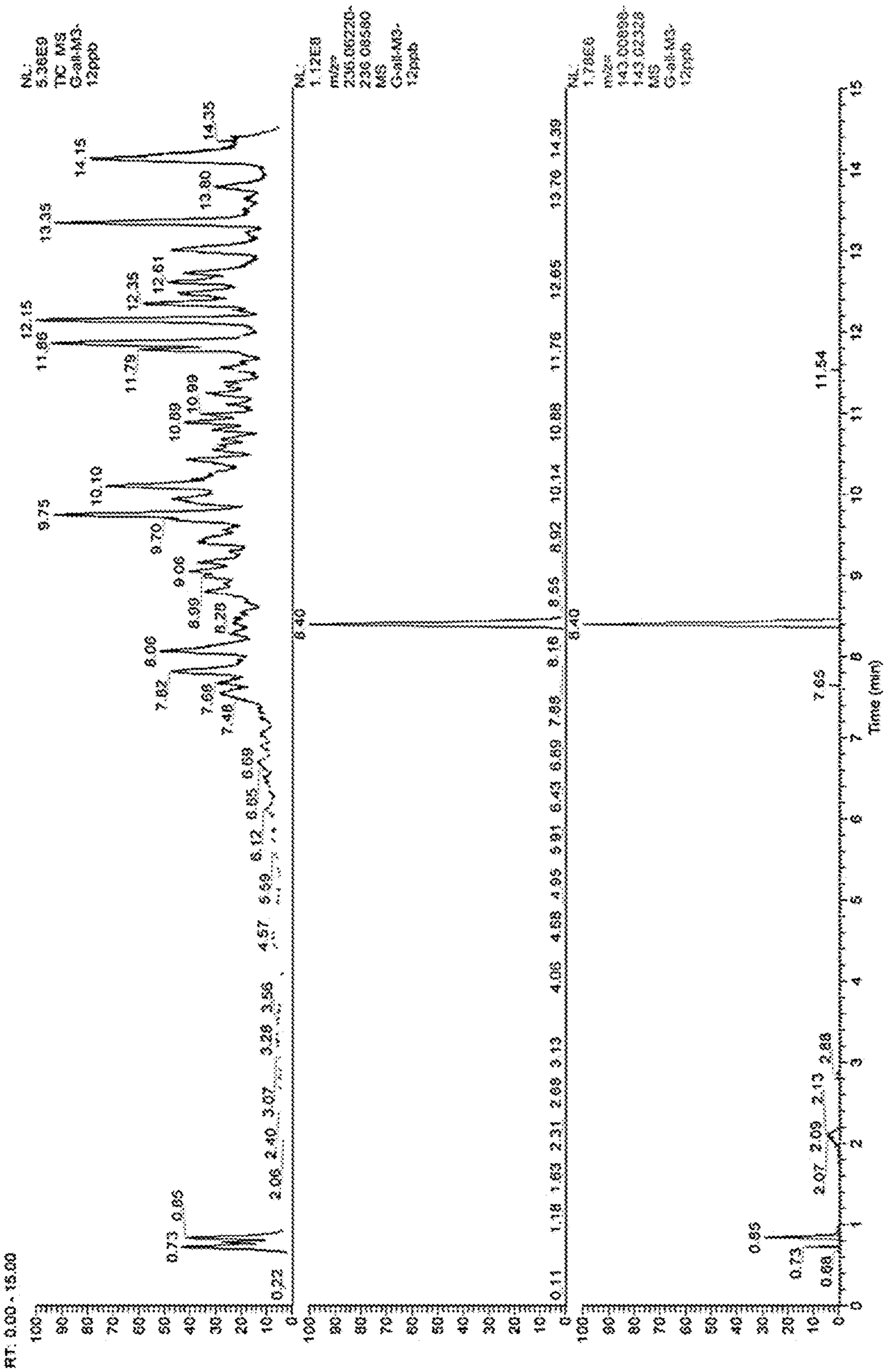
FIG. 20 is a chromatogram of carboxin standard in a full MS/ddMS$^2$ mode.
Figure 21:
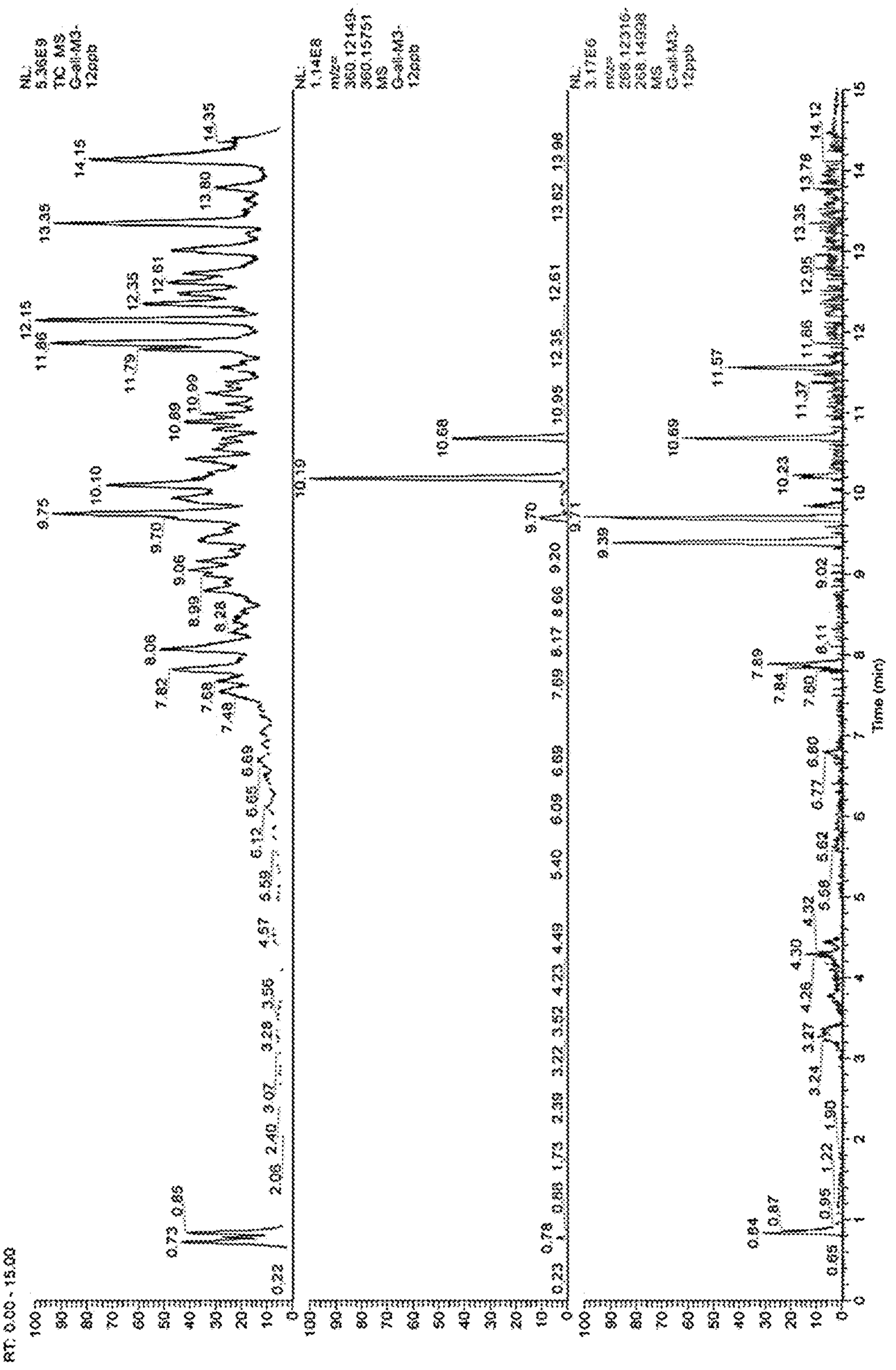
FIG. 21 is a chromatogram of clethodim standard in a full MS/ddMS$^2$ mode.
Figure 22:
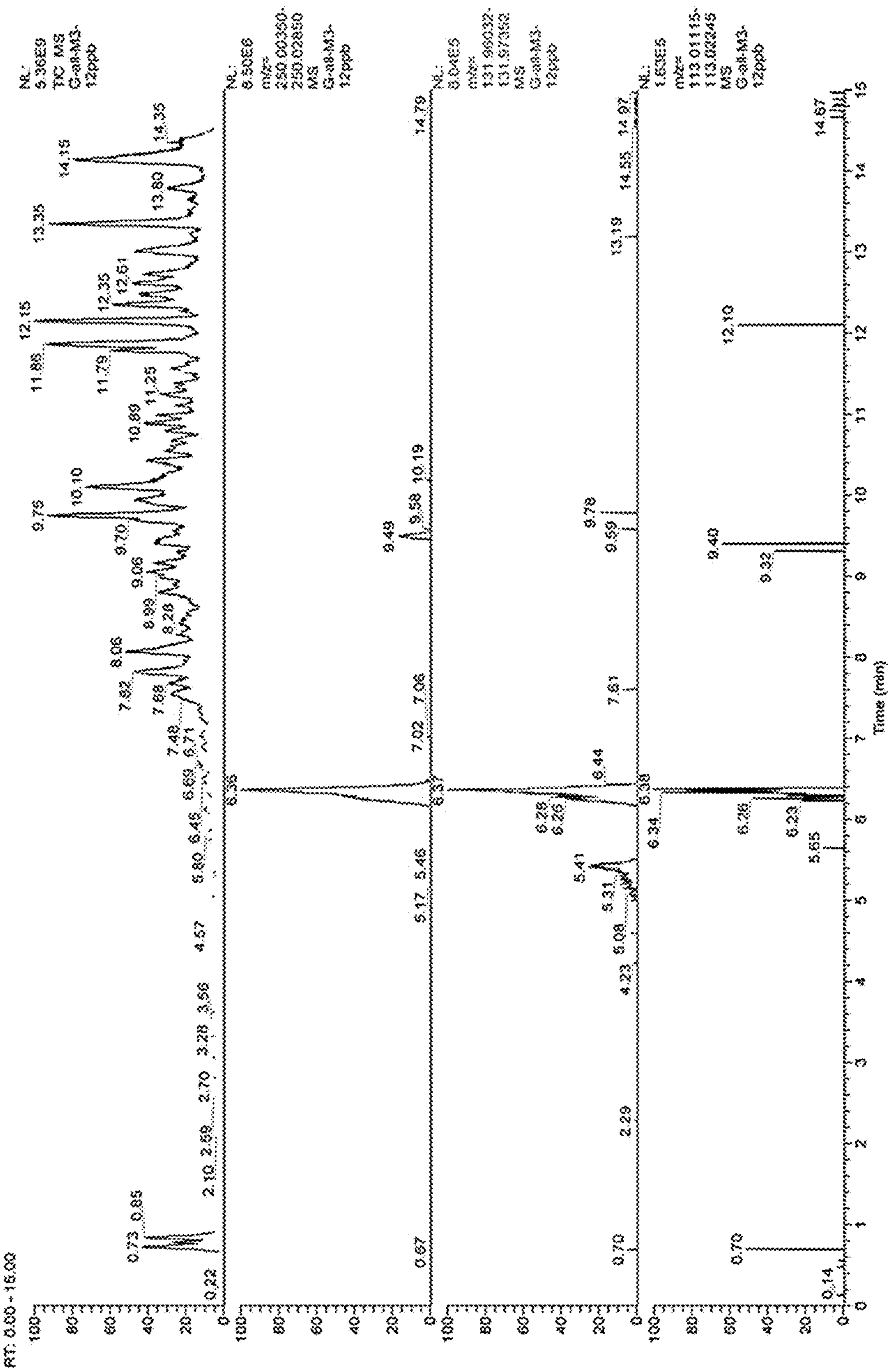
FIG. 22 is a chromatogram of clothianidin standard in a full MS/ddMS$^2$ mode.
Figure 23:
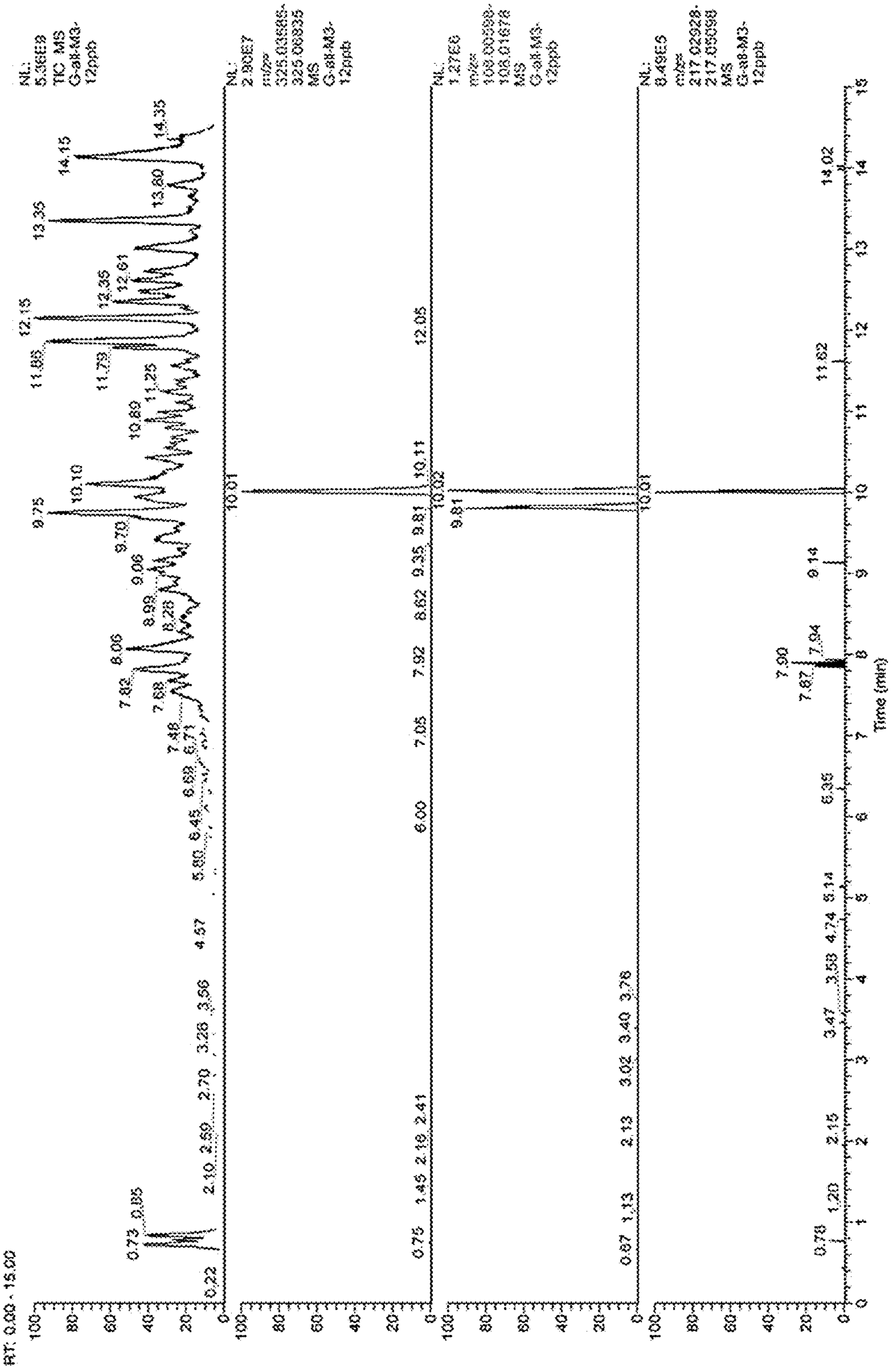
FIG. 23 is a chromatogram of cyazofamid standard in a full MS/ddMS$^2$ mode.
Figure 24:
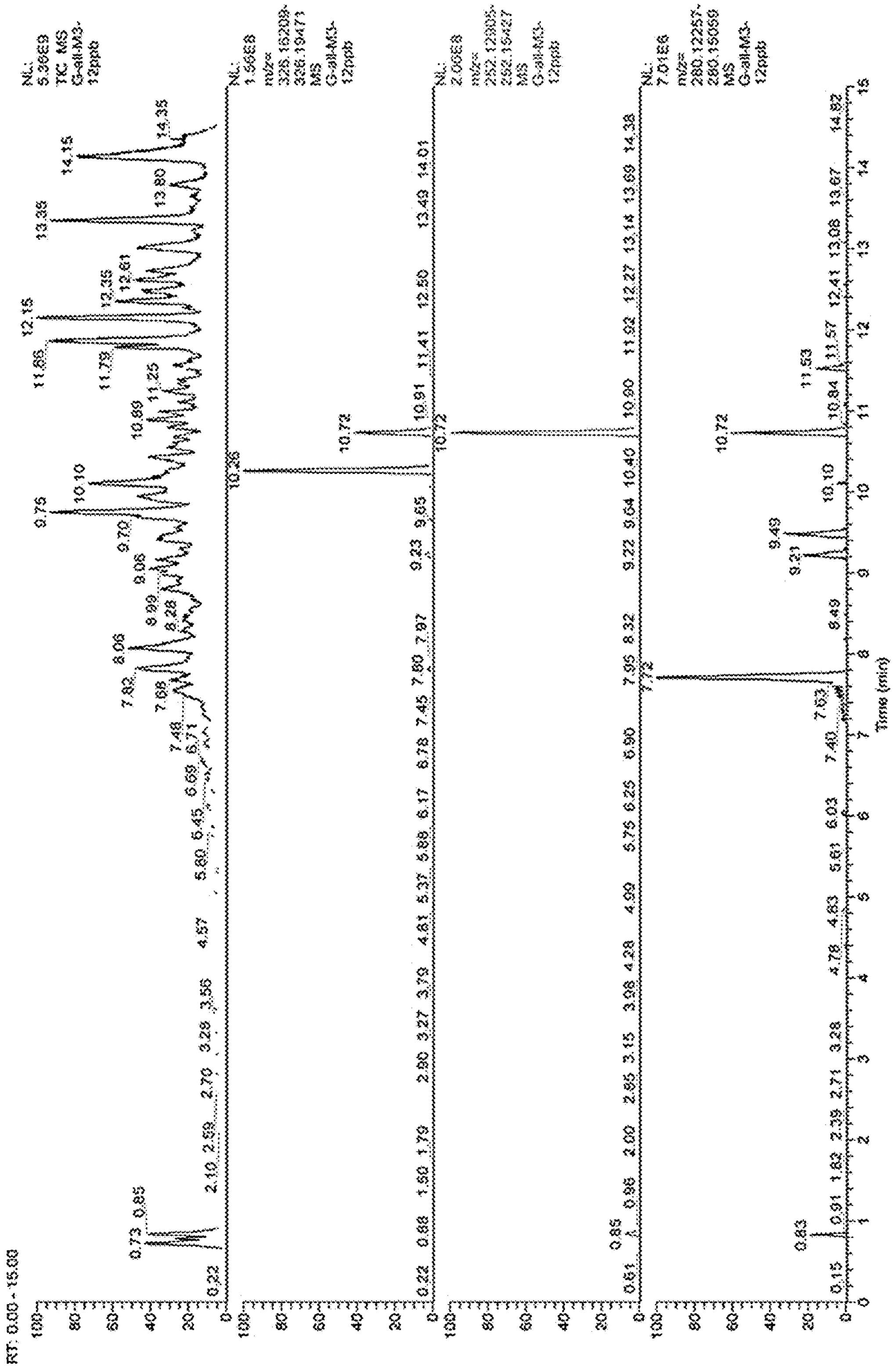
FIG. 24 is a chromatogram of cycloxydim standard in a full MS/ddMS$^2$ mode.
Figure 25:
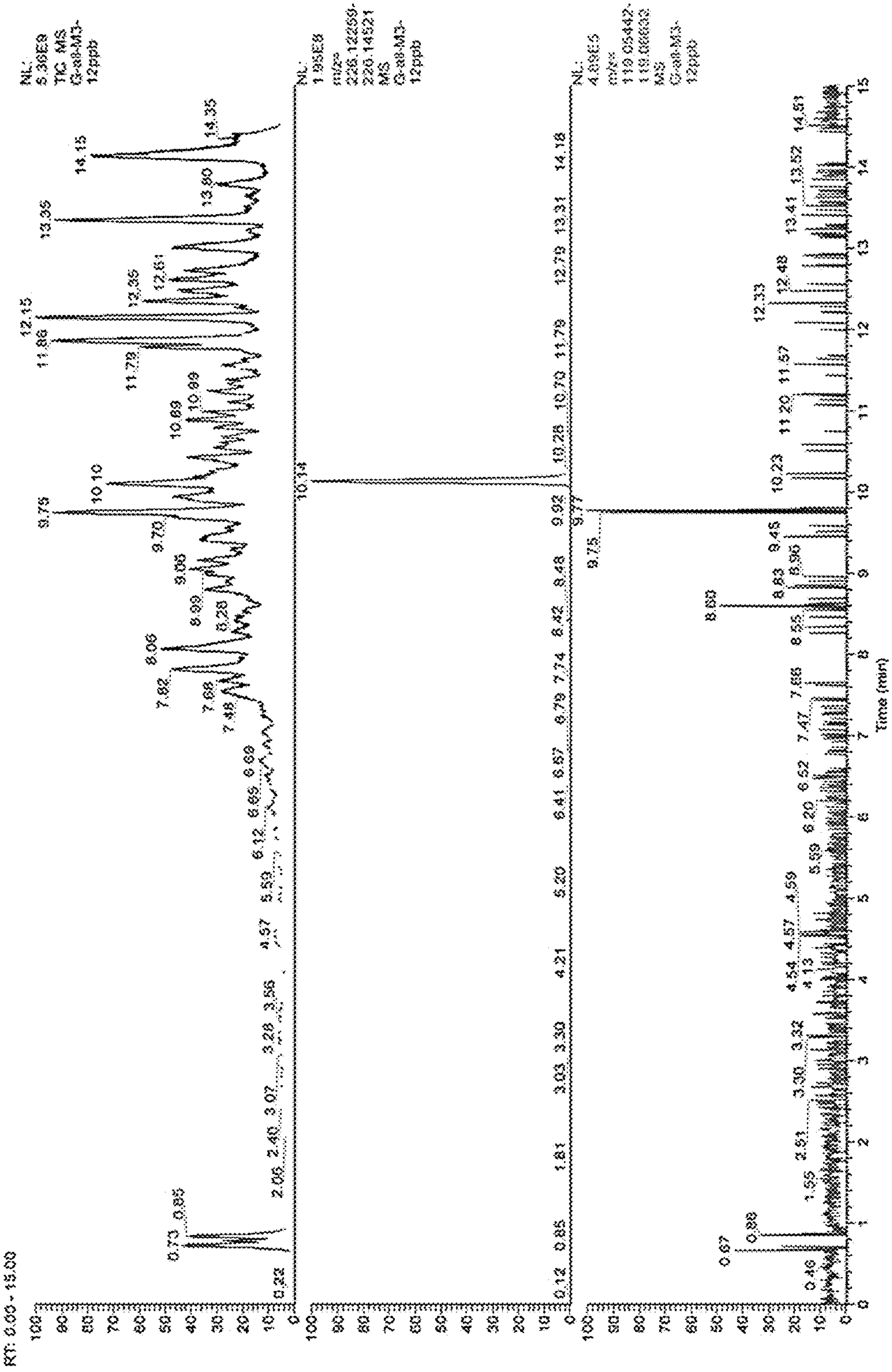
FIG. 25 is a chromatogram of cyprodinil standard in a full MS/ddMS$^2$ mode.
Figure 26:
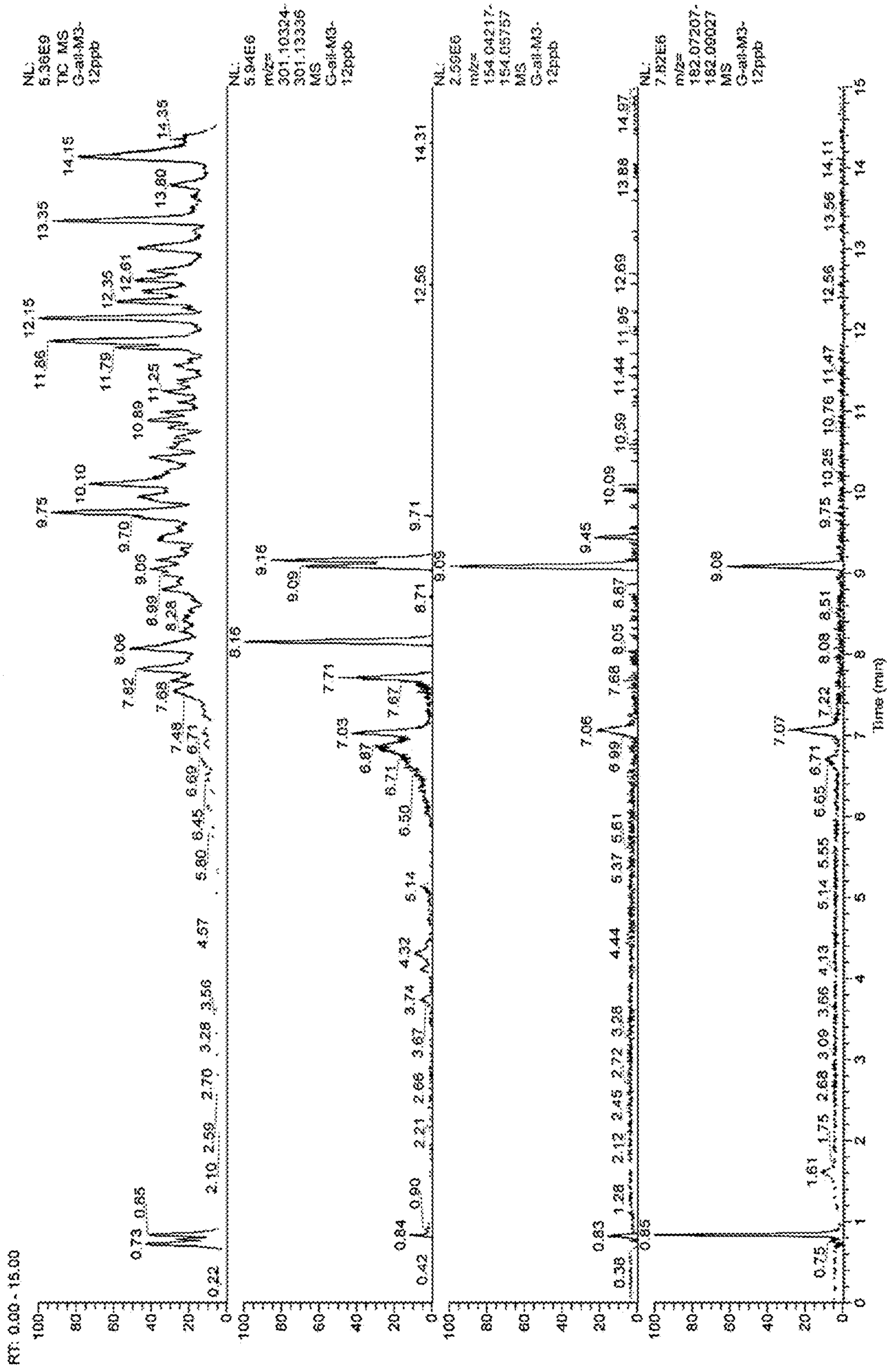
FIG. 26 is a chromatogram of desmedipham standard in a full MS/ddMS$^2$ mode.
Figure 27:
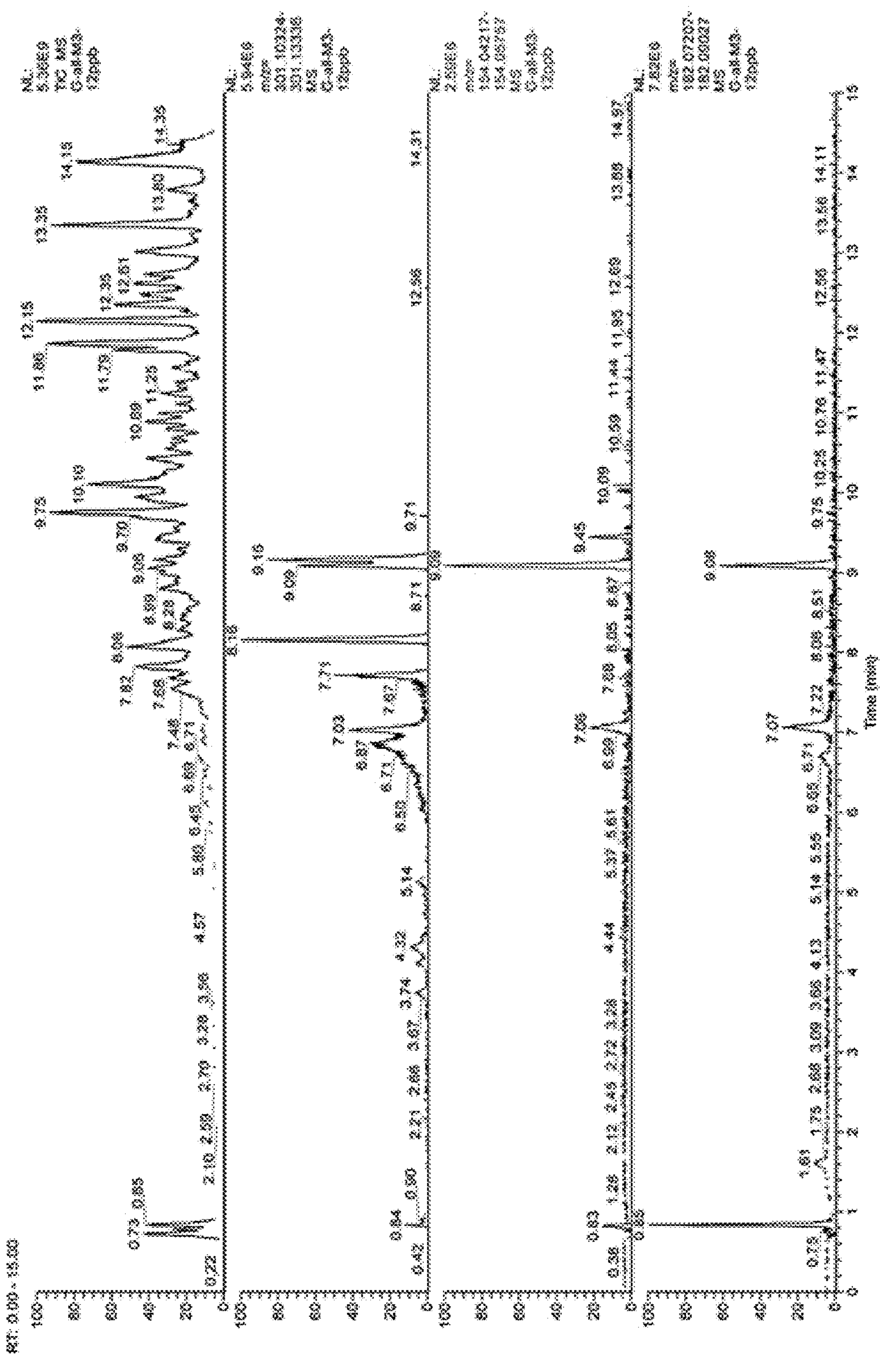
FIG. 27 is a chromatogram of dicrotophos standard in a full MS/ddMS$^2$ mode.
Figure 28:
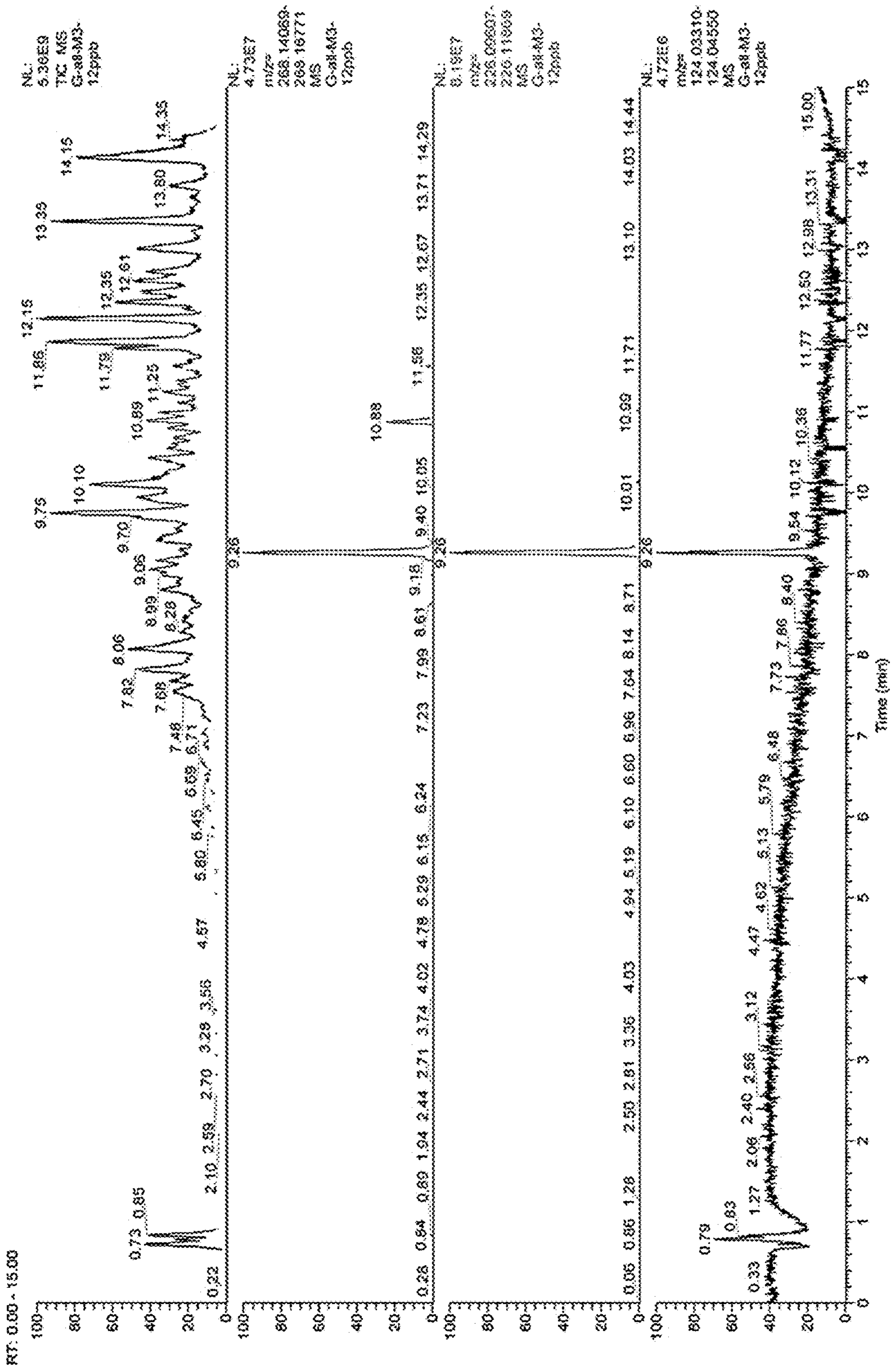
FIG. 28 is a chromatogram of diethofencarb standard in a full MS/ddMS$^2$ mode.
Figure 29:
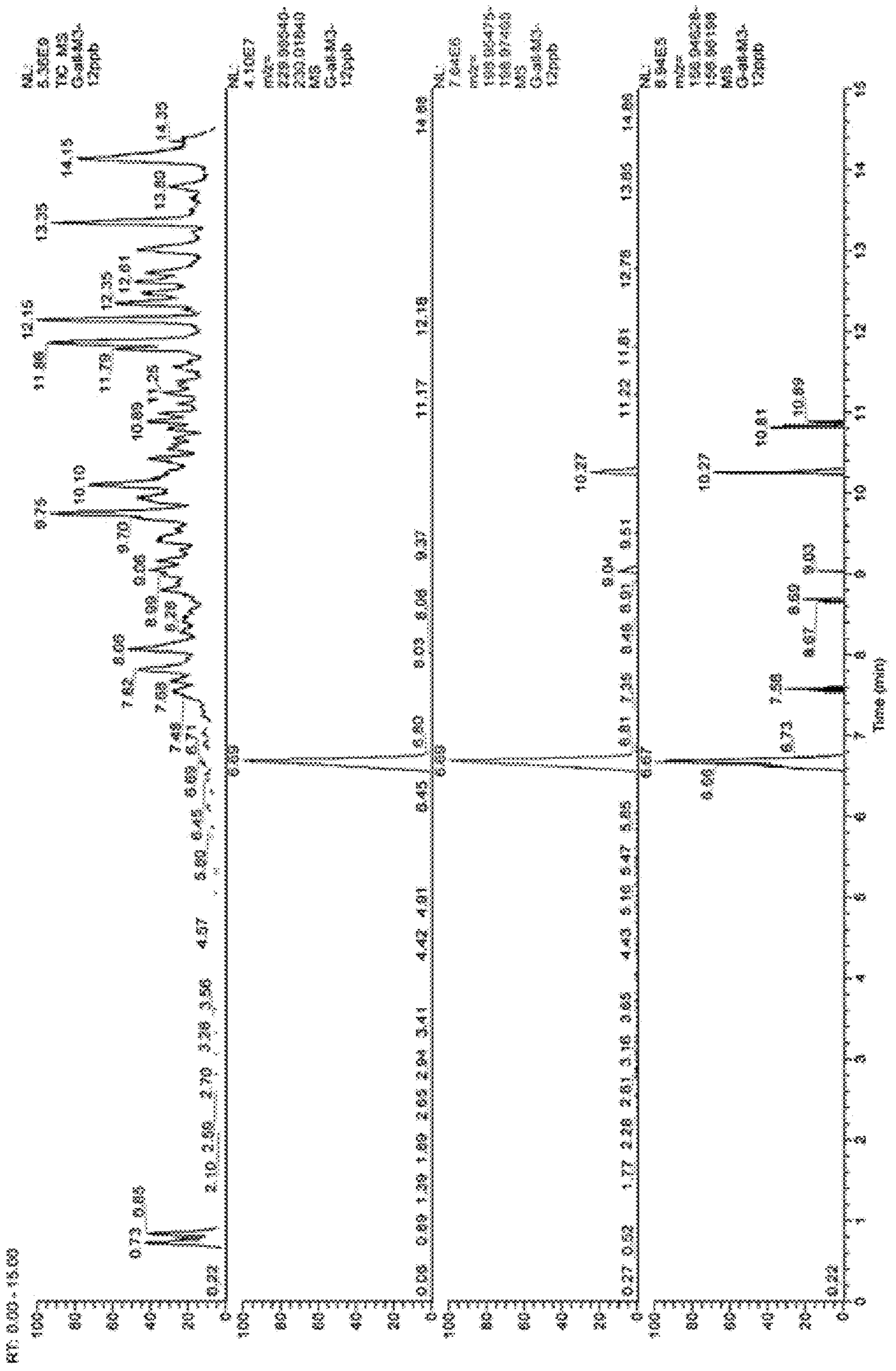
FIG. 29 is a chromatogram of dimethoate standard in a full MS/ddMS$^2$ mode.
Figure 30:
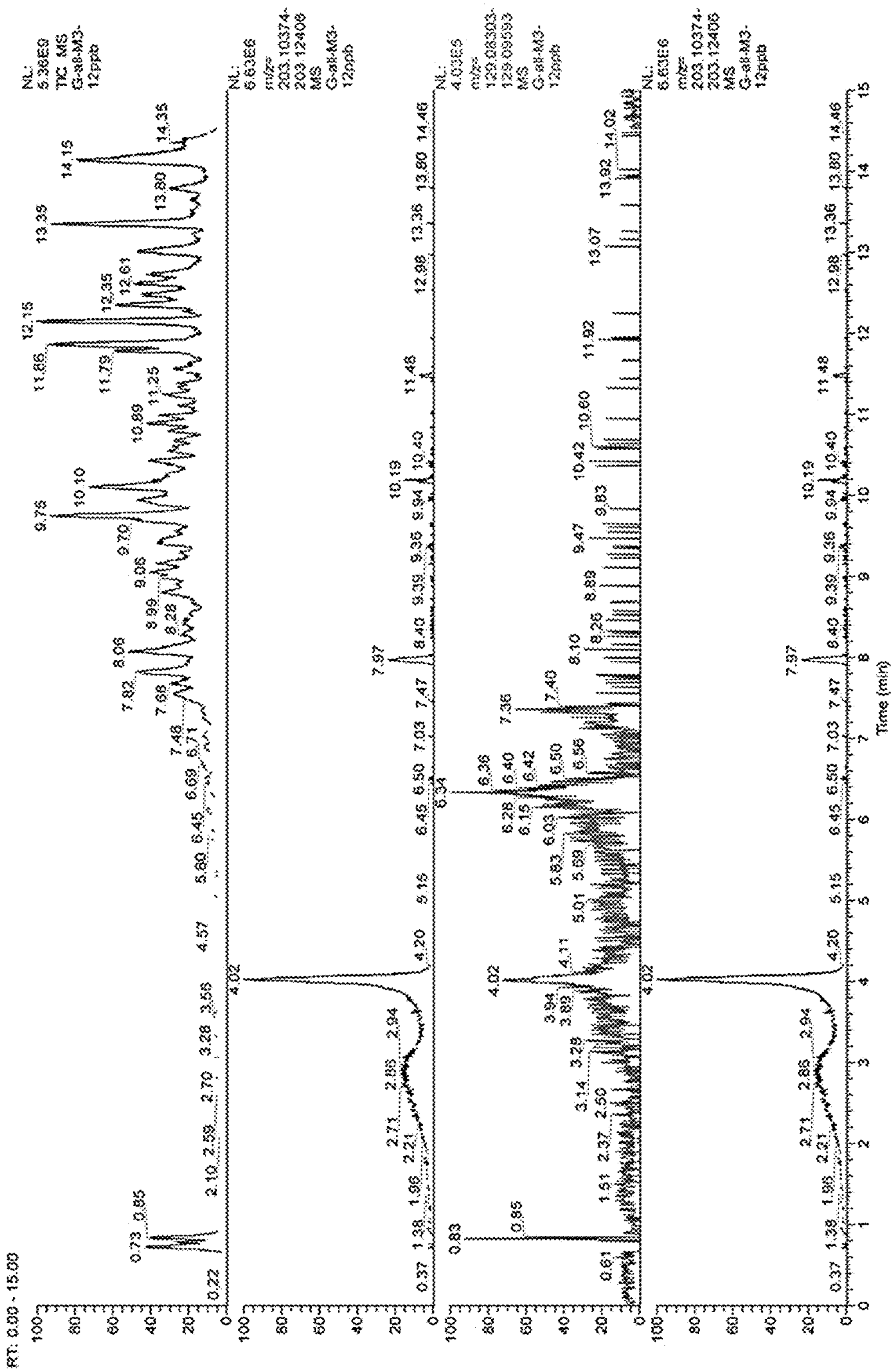
FIG. 30 is a chromatogram of dinotefuran standard in a full MS/ddMS$^2$ mode.

A database is constructed for simultaneously screening multiple pesticide residues.

1. Preparation and Preservation of Samples (1) Preparation of Samples

An edible part of a detecting object is chopped, then mixed evenly and sealed to use as a sample and followed by marking the sample to obtain a marked sample. The marked sample is placed at 0° C.-4° C. for cold storage.

(2) Pre-Processing Steps

The marked sample weighed to 5 grams (g) (accurated to 0.01 g) is put into a 50 mL plastic centrifuge tube, and acetonitrile of 10 mL, magnesium sulfate of 4 g, sodium chloride of 1 g, sodium citrate of 1 g, disodium hydrogen citrate of 0.5 g, and a ceramic homoproton are added into the 50 mL plastic centrifuge tube to obtain a first mixture, then the 50 mL plastic centrifuge tube is covered with a cover and shook vigorously for 1 minute (min), followed by centrifuging the first mixture at 4200 r/min for 5 min to obtain a first mixed solution. A supernatant of the first mixed solution of 6 mL is taken and added into a 15 mL plastic centrifuge tube containing 900 mg of magnesium sulfate and 150 mg of primary secondary amine (PSA) to obtain a second mixture. For the marked sample with a darker color, the magnesium sulfate of 885 mg, PSA of 150 mg, and graphitized carbon black (GCB) of 15 mg are added to the 15 mL plastic centrifuge tube, followed by vortex mixing for 1 min. The second mixture is centrifuged at 4200 r/min for 5 minutes to obtain a second mixed solution. A supernatant of the second mixed solution of 2 mL is accurately pipetted into a 10 mL test tube, and blown in a 40° C. water bath with nitrogen until almost dry. Acetonitrilxe and water (1:1) are added into the test tube to reconstitute, then filtered through a microporous membrane to obtain a filtered solution for detection.

2. Detection (1) A Condition of Liquid Chromatography a. A liquid chromatography column: an Accucore™ aQ C18 hydrophilic interaction liquid chromatography (HPLC) column, 150 millimeter (mm)×2.1 mm (i.d.), a particle size of 2.6 micrometer (μm), or equivalents;

b. A gradient elution procedure of the mobile phases is shown in Table 1;

c. The mobile phases: aqueous phase A (W) of ammonium formate of 5 millimol per liter (mM) and a 0.1% formic acid aqueous solution, and organic phase B (M) of ammonium formate of 5 mM and a 0.1% formic acid methanol solution;

d. A flow velocity: 0.4 mL/min;

e. A sample volume: 0.5 μL;

f. A column temperature: 25° C.

TABLE 1

The gradient elution procedure of the mobile phases

| time/min | aqueous phase % | organic phase % |
|---|---|---|
| 0 | 100 | 0 |
| 4 | 80 | 20 |
| 5.5 | 60 | 40 |
| 9.5 | 0 | 100 |
| 11.9 | 0 | 100 |
| 15 | 100 | 0 |

(2) A Condition of Mass Spectrometry

An ion source: an electrospray ion source with heated electrospray ionization (HESI-II) probe; a temperature of the ion source: 325° C.; a temperature of a heater: 350° C.; a sheath gas flow rate: 40 atmospheres relative to vacuum (arb); an aux gas flow rate: 10 arb; a scanning range of the mass spectrometry: 100-900 mass-to-charge ratios (MIZ) in a positive ion mode or 100-700 M/JZ in a negative ion mode; a resolution of the mass spectrometry: 70000 in full mass spectrometry scanning, or 17500 in tandem mass spectrometry (MS/MS); names of the pesticides, molecular formulas of the pesticides, accurate masses of the pesticides and accurate masses of characteristic ion fragments are shown in Table 2.

TABLE 2

Names of the pesticides, molecular formulas of the pesticides, accurate masses of the pesticides and accurate masses of characteristic ion fragments

| Name | Molecular formulas | Retention times | Scan mode | Parent ion | Characteristic ion fragments 1 | 2 | 3 | 4 | 5 |
|---|---|---|---|---|---|---|---|---|---|
| Acephate | $C_4H_{10}NO_3PS$ | 2.76 | Positive | 184.0192 | 142.99264 | 112.99968 | | | |
| Acetamiprid | $C_{10}H_{11}ClN_4$ | 6.71 | Positive | 223.0745 | 126.0105 | 98.9997 | 90.03383 | 72.98408 | 56.04948 |
| Aminocarb | $C_{11}H_{16}N_2O_2$ | 3.57 | Positive | 209.1285 | 152.10699 | 137.08352 | | | |
| Azamethiphos | $C_9H_{10}ClN_2O_5PS$ | 7.86 | Positive | 324.9809 | 182.99558 | 127.98977 | 139.00575 | | |
| Benalaxyl | $C_{20}H_{23}NO_3$ | 10.19 | Positive | 326.1751 | 148.11208 | 208.13321 | 91.05423 | 121.0886 | 266.15394 |
| Bendiocarb | $C_{11}H_{13}NO_4$ | 8.07 | Positive | 224.0917 | 109.02841 | 167.07027 | 127.03897 | 123.044 | 165.091 |
| Benfuracarb | $C_{20}H_{30}N_2O_5S$ | 10.65 | Positive | 411.1948 | 158.11756 | 195.04723 | 252.06905 | 148.04268 | 90.0372 |
| Bensulide | $C_{14}H_{24}NO_4PS_3$ | 10.02 | Positive | 398.0678 | 218.0304 | 141.00048 | 200.01989 | 61.01065 | 158.02703 |
| Benzoximate | $C_{18}H_{18}ClNO_5$ | 10.35 | Positive | 364.0946 | 105.03349 | 199.01565 | 95.04914 | 183.99217 | 140.97378 |
| Bifenazate | $C_{17}H_{20}N_2O_3$ | 9.68 | Positive | 301.1547 | 170.0965 | 198.09134 | 148.07569 | 120.08078 | 91.05423 |
| Bupirimate | $C_{13}H_{24}N_4O_3S$ | 9.75 | Positive | 317.1642 | 108.01138 | 166.09749 | 272.10634 | 150.10257 | 208.14444 |
| Butafenacil | $C_{20}H_{18}ClF_3N_2O_6$ | 9.7 | Positive | 475.0878 | 179.98468 | 331.00918 | 123.99485 | 349.01974 | |
| Butoxycarboxim | $C_7H_{14}N_2O_4S$ | 6.71 | Positive | 223.0747 | 167.03726 | 181.05291 | 90.03383 | 151.09917 | |
| Buturon | $C_{12}H_{13}ClN_2O$ | 8.9 | Positive | 237.0789 | 84.08078 | 126.0105 | 222.05544 | 128.02611 | 167.03705 |
| Carpropamid | $C_{15}H_{18}ClNO$ | 10.29 | Positive | 334.0527 | 139.0309 | 196.02905 | 160.05237 | 103.05423 | |
| Carbaryl | $C_{12}H_{11}NO_2$ | 8.36 | Positive | 202.0863 | 145.06479 | 117.06988 | 155.06061 | 127.05423 | 115.05423 |
| Carbendazim | $C_9H_9N_3O_2$ | 5.32 | Positive | 192.0768 | 160.05054 | 132.05562 | 105.04472 | 92.04948 | |
| Carbetamide | $C_{12}H_{16}N_2O_3$ | 7.78 | Positive | 237.1234 | 118.08626 | 120.04439 | 192.06552 | 100.07569 | 72.08078 |
| Carbofuran | $C_{12}H_{15}NO_3$ | 8.05 | Positive | 222.1125 | 123.04406 | 165.09101 | 137.05971 | 147.08044 | |
| Carboxin | $C_{12}H_{13}NO_2S$ | 8.33 | Positive | 236.074 | 143.01613 | 93.0573 | | | |
| Clethodim | $C_{17}H_{26}ClNO_3S$ | 10.62 | Positive | 360.1395 | 164.0706 | 268.13657 | 206.11755 | 136.07569 | 240.1053 |
| Clothianidin | $C_6H_8ClN_5O_2S$ | 6.29 | Positive | 250.016 | 131.96692 | 113.0168 | 169.05441 | 110.07127 | |
| Cyazofamid | $C_{13}H_{13}ClN_4O_2S$ | 9.95 | Positive | 325.0521 | 108.01138 | 216.0323 | 217.04013 | | |
| Cycloxydim | $C_{17}H_{27}NO_3S$ | 10.67 | Positive | 326.1784 | 180.10191 | 101.04195 | 155.05251 | 252.14166 | 280.13658 |
| Cyprodinil | $C_{14}H_{15}N_3$ | 10.07 | Positive | 226.1339 | 93.0573 | 91.05423 | 108.08708 | 118.05255 | 119.06037 |
| Desmedipham | $C_{16}H_{16}N_2O_4$ | 9.02 | Positive | 301.1183 | 136.0393 | 154.04987 | 182.08117 | 108.04439 | |
| Dicrotophos | $C_8H_{16}NO_5P$ | 6.02 | Positive | 238.0839 | 112.07569 | 127.01547 | 72.04439 | 193.02604 | |
| Diethofencarb | $C_{14}H_{21}NO_4$ | 9.19 | Positive | 268.1543 | 180.10191 | 152.0706 | 226.10738 | 124.0393 | 198.07608 |
| Dimethoate | $C_5H_{12}NO_3PS_2$ | 6.62 | Positive | 230.0069 | 198.9647 | 170.98978 | 88.02155 | 142.99286 | 156.95413 |
| Dinotefuran | $C_7H_{14}N_4O_3$ | 3.92 | Positive | 203.1139 | 129.08948 | 114.10231 | 113.09456 | 157.12086 | |
| Dioxacarb | $C_{11}H_{13}NO_4$ | 6.57 | Positive | 224.0917 | 123.04406 | 95.04914 | 167.07027 | 162.05495 | |
| Ethiofencarb | $C_{11}H_{15}NO_2S$ | 8.48 | Positive | 226.0896 | 107.04914 | 164.07059 | 95.04914 | 79.05423 | |
| Ethirimol | $C_{11}H_{19}N_3O$ | 7.32 | Positive | 210.1601 | 140.10699 | 98.06004 | 182.12879 | 193.13354 | 70.06513 |
| Ethofumesate | $C_{13}H_{18}O_5S$ | 9.6 | Positive | 287.0948 | 121.06479 | 259.06347 | 241.05291 | 162.06753 | 161.05971 |
| Fenazaquin | $C_{20}H_{22}N_2O$ | 11.5 | Positive | 307.1805 | 161.13248 | 147.05529 | 146.109 | 105.06988 | 131.08553 |
| Fenhexamid | $C_{14}H_{17}Cl_2NO_2$ | 9.71 | Positive | 302.0709 | 170.09643 | 198.09134 | 153.06988 | 184.07569 | 97.10118 |
| Fenobucarb | $C_{12}H_{17}NO_2$ | 9.24 | Positive | 208.1332 | 95.04914 | 152.0706 | 151.11174 | 57.06988 | |
| Fenoxycarb | $C_{17}H_{19}NO_4$ | 10.03 | Positive | 302.1387 | 88.0393 | 116.0706 | 256.09682 | | |
| Fenpropidin | $C_{19}H_{31}N$ | 9.1 | Positive | 274.2529 | 147.11683 | 86.09643 | 117.06988 | 132.09335 | 119.08553 |
| Flufenacet | $C_{14}H_{13}F_4N_3O_2S$ | 9.82 | Positive | 364.0737 | 152.05062 | 194.09757 | 124.0557 | | |
| Fuberidazole | $C_{11}H_8N_2O$ | 6.41 | Positive | 185.0709 | 157.07602 | 156.0682 | 92.04948 | 118.05255 | |
| Furalaxyl | $C_{17}H_{19}NO_4$ | 9.2 | Positive | 302.1387 | 242.11756 | 95.01276 | 270.11247 | | |
| Furathiocarb | $C_{18}H_{26}N_2O_5S$ | 10.72 | Positive | 383.1635 | 195.0474268 | 252.06889 | 164.08318 | | |
| Hexythiazox | $C_{17}H_{21}ClN_2O_2S$ | 11 | Positive | 353.1085 | 228.02444 | 168.05745 | 194.03672 | 271.03025 | 151.0309 |
| Hydramethylnon | $C_{25}H_{24}F_6N_4$ | 10.49 | Positive | 495.1978 | 323.14781 | 368.08739 | 171.04161 | 238.05866 | 128.11822 |

TABLE 2-continued

| Names of the pesticides, molecular formulas of the pesticides, accurate masses of the pesticides and accurate masses of characteristic ion fragments | | | | | | | | | |
|---|---|---|---|---|---|---|---|---|---|
| | Molecular | Retention | Scan | Parent | Characteristic ion fragments | | | | |
| Name | formulas | times | mode | ion | 1 | 2 | 3 | 4 | 5 |
| Imidacloprid | $C_9H_{10}ClN_5O_2$ | 6.23 | Positive | 256.0596 | 209.05885 | 175.09793 | 84.05562 | 210.06668 | |
| Indoxacarb | $C_{22}H_{17}ClF_3N_3O_7$ | 10.47 | Positive | 528.078 | 218.04234 | 203.01886 | 190.00542 | 168.02116 | 249.0426 |
| Isoprocarb | $C_{11}H_{15}NO_2$ | 8.72 | Positive | 194.1176 | 95.04914 | 137.09609 | 152.0706 | | |
| Mefenacet | $C_{16}H_{14}N_2O_2S$ | 9.64 | Positive | 299.0849 | 148.07569 | 120.08078 | 192.01138 | 91.05423 | 136.02155 |
| Mepanipyrim | $C_{14}H_{13}N_3$ | 9.84 | Positive | 224.1182 | 106.06513 | 131.06037 | 79.05423 | 105.04472 | 104.04948 |
| Mepronil | $C_{17}H_{19}NO_2$ | 9.57 | Positive | 270.1489 | 119.04914 | 228.10191 | 136.0393 | 91.05423 | 93.06988 |
| Metalaxyl | $C_{15}H_{21}NO_4$ | 8.78 | Positive | 280.1543 | 220.13321 | 192.13829 | 160.11208 | 248.12812 | 148.11208 |
| Methamidophos | $C_2H_8NO_2PS$ | 2 | Positive | 142.0086 | 124.98206 | 109.98229 | 94.00524 | | |
| Methomyl | $C_5H_{10}N_2O_2S$ | 4.83 | Positive | 163.0536 | 106.03211 | 88.02155 | | | |
| Methoxyfenozide | $C_{22}H_{28}N_2O_3$ | 9.59 | Positive | 369.2173 | 149.05971 | 133.06479 | 91.05423 | 109.06479 | 105.06988 |
| Metolcarb | $C_9H_{11}NO_2$ | 7.71 | Positive | 166.0863 | 109.06479 | 94.04101 | 91.05423 | 81.06988 | |
| Metribuzin | $C_8H_{14}N_4OS$ | 7.97 | Positive | 215.0961 | 187.10119 | 131.03859 | 84.08078 | 89.0168 | 74.0059 |
| Napropamide | $C_{17}H_{21}NO_2$ | 9.84 | Positive | 272.1645 | 129.11483 | 171.08044 | 199.07536 | 114.09134 | 74.09643 |
| Nitenpyram | $C_{11}H_{15}ClN_4O_2$ | 4.65 | Positive | 271.0956 | 224.0949 | 196.0636 | 126.0105 | 99.09167 | 210.07925 |
| Nuarimol | $C_{17}H_{12}ClFN_2O$ | 9.29 | Positive | 315.0695 | 81.04476 | 252.08891 | 243.0372 | 138.99452 | 123.02407 |
| Omethoate (Dimethoateoxon) | $C_5H_{12}NO_4PS$ | 3.39 | Positive | 214.0297 | 142.99263 | 182.98754 | 127.01547 | 154.99263 | 196.01918 |
| Oxamyl | $C_7H_{13}N_3O_3S$ | 4.52 | Positive | 220.075 | 72.04439 | 90.05495 | | | |
| Pencycuron | $C_{19}H_{21}ClN_2O$ | 10.46 | Positive | 329.1415 | 125.01525 | 261.07892 | 210.1044 | | |
| Pirimicarb | $C_{11}H_{18}N_4O_2$ | 7.29 | Positive | 239.1503 | 72.04439 | 182.12895 | 109.07602 | 137.07094 | |
| Propamocarb | $C_9H_{20}N_2O_2$ | 3.65 | Positive | 189.1598 | 102.05495 | 144.10191 | | | |
| Propargite | $C_{19}H_{26}O_4S$ | 11.05 | Positive | 351.1625 | 175.11174 | 231.17434 | 107.04914 | 81.06988 | 163.11174 |
| Propoxur | $C_{11}H_{15}NO_3$ | 8 | Positive | 210.1125 | 111.04406 | 168.06552 | 153.09101 | 93.03349 | |
| Prosulfocarb | $C_{14}H_{21}NOS$ | 10.67 | Positive | 252.1417 | 91.05423 | 128.10699 | 86.06004 | 65.03858 | |
| Pyrimethanil | $C_{12}H_{13}N_3$ | 9.16 | Positive | 200.1182 | 107.06037 | 82.06513 | 183.09167 | 168.0682 | 183.09167 |
| Quinoxyfen | $C_{15}H_8CLFNO$ | 11.1 | Positive | 308.004 | 162.01064 | 196.97951 | 213.98221 | 272.0273 | 75.02293 |
| Rotenone | $C_{23}H_{22}O_6$ | 9.92 | Positive | 395.1489 | 213.09101 | 192.0781 | 203.07027 | 179.07027 | 191.07027 |
| Spirodiclofen | $C_{21}H_{24}C_{12}O_4$ | 11.21 | Positive | 411.1124 | 71.08553 | 313.03928 | 295.02871 | 212.95046 | 184.95555 |
| Tebufenozide | $C_{22}H_{28}N_2O_2$ | 10.03 | Positive | 353.2224 | 133.06479 | 105.06988 | 72.08078 | 103.05423 | 95.04919 |
| Tebutam | $C_{15}H_{23}NO$ | 9.89 | Positive | 234.1852 | 91.05423 | 192.13829 | 142.12264 | 84.08078 | |
| Temephos | $C_{16}H_{20}O_6P_2S_3$ | 10.83 | Positive | 466.997 | 142.99275 | 341.00656 | 404.978 | 248.98035 | 437.0042 |
| Thiabendazole | $C_{10}H_7N_3S$ | 6.13 | Positive | 202.0433 | 175.03245 | 131.06037 | 92.04948 | | |
| Thiacloprid | $C_{10}H_9ClN_4S$ | 7.18 | Positive | 253.0309 | 126.0105 | 98.9996 | 90.03383 | | |
| Thiamethoxam | $C_8H_{10}ClN_5O_3S$ | 5.33 | Positive | 292.0266 | 131.96692 | 181.05447 | 211.06481 | 152.02795 | 122.07143 |
| Thiobencarb | $C_{12}H_{16}ClNOS$ | 10.39 | Positive | 258.0714 | 125.01525 | 100.07569 | | | |
| Thiodicarb | $C_{10}H_{18}N_4O_4S_3$ | 8.43 | Positive | 355.0563 | 88.0215465 | 107.99362 | 78.96707 | | |
| Thiophanate-methyl | $C_{12}H_{14}N_4O_4S_2$ | 8 | Positive | 343.0529 | 151.03245 | 311.02671 | 268.02089 | 194.03826 | 235.99468 |
| Trichlorfon | $C_4H_8C_{13}O_4P$ | 6.42 | Positive | 256.9299 | 127.01552 | 220.95318 | 78.99434 | | |
| Vamidothion | $C_8H_{18}NO_4PS_2$ | 6.6 | Positive | 288.0488 | 118.03211 | 146.06341 | 86.06004 | 119.03657 | 104.07061 |
| Ametryn | $C_9H_{17}N_5S$ | 8.84 | Positive | 228.1277 | 186.08079 | 96.05562 | 116.02769 | 71.06037 | 138.07742 |
| Atrazine | $C_8H_{14}ClN_5$ | 8.82 | Positive | 216.101 | 174.0541 | 96.05562 | 104.001 | 132.0323 | 146.0228 |
| Azoxystrobin | $C_{22}H_{17}N_3O_5$ | 9.28 | Positive | 404.1241 | 344.10397 | 329.07949 | 372.09788 | 328.07167 | 300.07675 |
| Benodanil | $C_{13}H_{10}INO$ | 8.84 | Positive | 323.988 | 230.93013 | 94.04132 | 76.03075 | 104.02567 | |
| Benoxacor | $C_{11}H_{11}Cl_2O_2$ | 9.28 | Positive | 260.024 | 149.08352 | 120.04439 | 134.06004 | 150.09134 | 160.07569 |
| Bitertanol | $C_{20}H_{23}N_3O_2$ | 10.41 | Positive | 338.1863 | 70.03997 | 99.08044 | 269.15361 | 251.14304 | 183.08044 |
| Boscalid | $C_{18}H_{12}Cl_2N_2O$ | 9.53 | Positive | 343.0399 | 307.06327 | 271.08659 | 139.98977 | 96.04439 | |
| Buprofezin | $C_{16}H_{23}N_3OS$ | 10.84 | Positive | 306.1635 | 201.10561 | 116.05285 | 106.06513 | 145.04301 | 86.06004 |

TABLE 2-continued

Names of the pesticides, molecular formulas of the pesticides, accurate masses of the pesticides and accurate masses of characteristic ion fragments

| | Molecular | Retention | Scan | Parent | Characteristic ion fragments | | | | |
|---|---|---|---|---|---|---|---|---|---|
| Name | formulas | times | mode | ion | 1 | 2 | 3 | 4 | 5 |
| Butylate | $C_{11}H_{23}NOS$ | 10.81 | Positive | 218.1573 | 156.13829 | 162.09471 | 100.07569 | 125.09609 | |
| Chlorfluazuron | $C_{20}H_9Cl_3F_5N_3O_3$ | 11.25 | Positive | 539.9702 | 382.93632 | 141.01465 | 186.95862 | 158.0412 | |
| Cumyluron | $C_{17}H_{19}ClN_2O$ | 9.79 | Positive | 303.1259 | 185.04762 | 119.08553 | 125.01525 | 91.05423 | 73.03964 |
| Cyanazine | $C_9H_{13}ClN_6$ | 7.93 | Positive | 241.0963 | 214.0854 | 96.05562 | 104.001 | 132.0323 | 174.0541 |
| Cycluron | $C_{11}H_{22}N_2O$ | 9.03 | Positive | 199.1805 | 72.04439 | 89.07094 | 69.06988 | 111.11683 | |
| Cyproconazole | $C_{15}H_{18}ClN_3O$ | 10.09 | Positive | 292.1211 | 70.03997 | 125.01525 | | | |
| Cyromazine | $C_6H_{10}N_6$ | 2.54 | Positive | 167.104 | 85.05087 | 125.08217 | 108.05562 | 83.06037 | 60.05562 |
| Diclobutrazol | $C_{15}H_{19}C_{12}N_3O$ | 10.2 | Positive | 328.0978 | 70.03997 | 158.97628 | | | |
| Diflufenican | $C_{19}H_{11}F_5N_2O_2$ | 10.69 | Positive | 395.0813 | 266.04234 | 238.04742 | 169.05222 | 145.02596 | 96.04439 |
| Dimepiperate | $C_{15}H_{21}NOS$ | 10.66 | Positive | 264.1417 | 146.06341 | 119.08553 | 91.05423 | 112.07569 | 69.06988 |
| Dimethametryn | $C_{11}H_{21}N_5S$ | 9.89 | Positive | 256.159 | 186.08079 | 96.05562 | 71.06037 | 116.02769 | 68.02432 |
| Dimethenamid | $C_{12}H_{18}ClNO_2S$ | 9.47 | Positive | 276.082 | 168.08415 | 244.05574 | 126.0372 | 111.0263 | 152.05285 |
| Dimethomorph | $C_{21}H_{22}ClNO_4$ | 9.58 | Positive | 388.131 | 301.0626 | 165.05462 | 138.99452 | 273.06768 | 70.02874 |
| Diniconazole | $C_{15}H_{17}Cl_2N_3O$ | 10.58 | Positive | 326.0821 | 70.03997 | 158.97628 | 172.95555 | | |
| Diphenamid | $C_{16}H_{17}NO$ | 9.09 | Positive | 240.1383 | 134.09643 | 167.08553 | 165.06988 | 152.06205 | 91.05423 |
| Dipropetryn | $C_{11}H_{21}N_5S$ | 9.89 | Positive | 256.159 | 214.11209 | 144.03384 | 172.06514 | 186.08079 | 228.12774 |
| Diuron | $C_9H_{10}Cl_2N_2O$ | 9.11 | Positive | 233.0243 | 72.04439 | 159.97153 | | | |
| Dodemorph | $C_{18}H_{35}NO$ | 9.1 | Positive | 282.2791 | 116.10699 | 98.09643 | 97.10118 | 83.08553 | |
| Epoxiconazole | $C_{17}H_{13}ClFN_3O$ | 9.94 | Positive | 330.0804 | 121.0448 | 123.02407 | 91.05423 | 70.03997 | 141.01017 |
| Ethiprole | $C_{13}H_9C_{12}F_3N_4OS$ | 9.46 | Positive | 396.9899 | 254.96981 | 350.94803 | 212.94802 | 227.95892 | |
| Etobenzanid | $C_{16}H_{15}CLNO_3$ | 10.39 | Positive | 340.0502 | 179.07027 | 149.05986 | 121.02841 | 282.00831 | |
| Fenbuconazole | $C_{19}H_{17}ClN_4$ | 10.01 | Positive | 337.1215 | 70.03997 | 125.01525 | 91.05423 | | |
| Fenpropathrin | $C_{22}H_{23}NO_3$ | 11.2 | Positive | 350.1751 | 125.09609 | 181.06479 | 97.10118 | | |
| Fenpropimorph | $C_{20}H_{33}NO$ | 9.32 | Positive | 304.2635 | 147.11683 | 117.06988 | 132.09335 | 119.08553 | 105.06988 |
| Fenpyroximate | $C_{24}H_{27}N_3O_4$ | 11.23 | Positive | 422.2074 | 138.06619 | 366.14483 | 231.10023 | 135.04406 | 214.09749 |
| Fenuron | $C_9H_{12}N_2O$ | 6.52 | Positive | 165.1022 | 72.04439 | 120.04439 | 92.04948 | | |
| Flufenoxuron | $C_{21}H_{11}ClF_6N_2O_3$ | 11.13 | Positive | 489.0435 | 158.0412 | 141.01465 | 306.03033 | | |
| Fluometuron | $C_{10}H_{11}F_3N_2O$ | 8.69 | Positive | 233.0896 | 72.04439 | 160.03686 | 168.02555 | | |
| Flurtamone | $C_{18}H_{14}F_3NO_2$ | 9.45 | Positive | 334.1049 | 247.07291 | 105.03349 | 178.07774 | 227.06665 | |
| Flusilazole | $C_{16}H_{15}F_2N_3Si$ | 10.08 | Positive | 316.1076 | 187.05819 | 165.06969 | | | |
| Flutolanil | $C_{17}H_{16}F_3NO_2$ | 9.62 | Positive | 324.1206 | 242.0611 | 262.06741 | 173.02088 | 282.07364 | |
| Flutriafol | $C_{16}H_{13}F_2N_3O$ | 8.84 | Positive | 302.1099 | 70.03997 | 123.02407 | 233.07725 | 109.0448 | |
| Forchlorfenuron | $C_{12}H_{10}ClN_3O$ | 9.07 | Positive | 248.0585 | 129.0214 | 155.00067 | 137.03473 | | |
| Imazalil | $C_{14}H_{14}Cl_2N_2O$ | 8.74 | Positive | 297.0556 | 158.97628 | 255.00864 | 200.98685 | 172.99193 | 81.04472 |
| Imibenconazole | $C_{17}H_{13}Cl_3N_4S$ | 10.93 | Positive | 410.9999 | 125.01525 | 341.96723 | 171.00307 | 295.97951 | 251.01527 |
| Isoproturon | $C_{12}H_{18}N_2O$ | 8.94 | Positive | 207.1492 | 72.04439 | 165.10224 | 134.09643 | | 125.00268 |
| Linuron | $C_9H_{10}Cl_2N_2O_2$ | 9.53 | Positive | 249.0192 | 159.97153 | 182.02414 | 160.97936 | 132.96063 | 125.00268 |
| Metconazole | $C_{17}H_{22}ClN_3O$ | 10.43 | Positive | 320.1524 | 70.03997 | 125.01525 | | | |
| Methabenzthiazuron | $C_{10}H_{11}N_3OS$ | 8.97 | Positive | 222.0696 | 165.0481 | 150.02462 | 124.02155 | 109.01065 | 92.04948 |
| Methoprotryne | $C_{11}H_{21}N_5OS$ | 8.88 | Positive | 272.154 | 198.08079 | 240.12774 | 230.10701 | 212.09644 | 170.04949 |
| Metobromuron | $C_9H_{11}BrN_2O_2$ | 8.88 | Positive | 259.0077 | 169.95999 | 148.06311 | 170.96781 | 91.04165 | 119.06037 |
| Metoxuron | $C_{10}H_{13}ClN_2O_2$ | 7.63 | Positive | 229.0738 | 72.04439 | 156.02107 | | | |
| Monolinuron | $C_9H_{11}ClN_2O_2$ | 8.64 | Positive | 215.0582 | 126.0105 | 148.06311 | 127.01833 | 98.9996 | |
| Myclobutanil | $C_{15}H_{17}ClN_4$ | 9.72 | Positive | 289.1215 | 70.03997 | 125.01525 | 151.0309 | 220.08875 | 164.02615 |
| Neburon | $C_{12}H_{16}Cl_2N_2O$ | 10.22 | Positive | 275.0712 | 88.11208 | 114.09134 | 57.06988 | 58.02874 | 187.96645 |
| Paclobutrazol | $C_{15}H_{20}ClN_3O$ | 9.6 | Positive | 294.1368 | 70.03997 | 125.01525 | 87.08044 | | |
| Penconazole | $C_{13}H_{15}Cl_2N_3$ | 10.25 | Positive | 284.0716 | 70.03997 | 158.97628 | 172.99193 | | |

TABLE 2-continued

Names of the pesticides, molecular formulas of the pesticides, accurate masses of the pesticides and accurate masses of characteristic ion fragments

| Name | Molecular formulas | Retention times | Scan mode | Parent ion | Characteristic ion fragments 1 | 2 | 3 | 4 | 5 |
|---|---|---|---|---|---|---|---|---|---|
| Phenmedipham | $C_{16}H_{16}N_2O_4$ | 9.2 | Positive | 301.1183 | 136.0393 | 168.06552 | 108.04439 | 111.04406 | |
| Picoxystrobin | $C_{18}H_{16}F_3NO_4$ | 10.09 | Positive | 368.1104 | 145.06479 | 115.05423 | 130.04132 | 91.05423 | 117.06988 |
| Prochloraz | $C_{15}H_{16}Cl_3N_3O_2$ | 10.36 | Positive | 376.0381 | 308.00064 | 265.95369 | 222.94787 | 70.02874 | 70.06513 |
| Prometon | $C_{10}H_{19}N_5O$ | 8.41 | Positive | 226.1662 | 142.07234 | 184.11929 | 100.05054 | 68.02432 | |
| Prometryn | $C_{10}H_{19}N_5S$ | 9.43 | Positive | 242.1434 | 158.04949 | 200.09644 | 116.02769 | 68.02432 | 110.04612 |
| Propazine | $C_9H_{16}ClN_5$ | 9.38 | Positive | 230.1167 | 146.0228 | 188.06975 | 104.001 | 110.04612 | |
| Propiconazole | $C_{15}H_{17}Cl_2N_3O_2$ | 10.3 | Positive | 342.0771 | 158.97628 | 204.98176 | 186.9712 | | |
| Pymetrozine | $C_{10}H_{11}N_5O$ | 3.72 | Positive | 218.1036 | 105.04472 | 79.04127 | 78.03344 | | |
| Pyraclostrobin | $C_{19}H_{18}ClN_3O_4$ | 10.41 | Positive | 388.1059 | 163.06278 | 164.0706 | 194.08117 | 296.05852 | 149.04713 |
| Pyriproxyfen | $C_{20}H_{19}NO_3$ | 11.03 | Positive | 322.1438 | 96.04439 | 227.10666 | 185.05971 | 134.07262 | 136.07569 |
| Sebuthylazine | $C_9H_{16}ClN_5$ | 9.51 | Positive | 230.1167 | 174.0541 | 96.05562 | 132.0323 | 104.001 | 68.02432 |
| Secbumeton | $C_{10}H_{19}N_5O$ | 8.41 | Positive | 226.1662 | 170.10364 | 100.05054 | 142.07234 | 128.08184 | 96.05562 |
| Simeconazole | $C_{14}H_{20}FN_3OSi$ | 9.92 | Positive | 294.1432 | 70.03997 | 135.06045 | 73.0468 | 209.07925 | |
| Simetryn | $C_8H_{15}N_5S$ | 8.14 | Positive | 214.1121 | 124.0871 | 96.05562 | 144.05899 | 116.02769 | 166.10872 |
| Tebuconazole | $C_{16}H_{22}ClN_3O$ | 10.26 | Positive | 308.1524 | 70.03397 | 125.01525 | 151.0309 | | |
| Tebuthiuron | $C_9H_{16}N_4OS$ | 8.24 | Positive | 229.1118 | 116.02769 | 172.09029 | 157.06682 | 74.0059 | 62.0059 |
| Terbuthylazine | $C_9H_{16}ClN_5$ | 9.38 | Positive | 230.1167 | 174.0541 | 96.05562 | 132.0323 | 146.0228 | 104.001 |
| Terbumeton | $C_{10}H_{19}N_5O$ | 8.41 | Positive | 226.1662 | 170.10364 | 142.07234 | 100.05054 | | |
| Terbutryn | $C_{10}H_{19}N_5S$ | 9.53 | Positive | 242.1434 | 186.08079 | 68.02432 | 71.06037 | 96.05562 | 116.02769 |
| Tetraconazole | $C_{13}H_{11}C_{12}F_4N_3O$ | 9.92 | Positive | 372.0288 | 158.97628 | 70.03997 | 184.99193 | | |
| Thenylchlor | $C_{16}H_{18}ClNO_2S$ | 9.9 | Positive | 324.082 | 127.02121 | 97.01065 | 65.03858 | 58.995 | |
| Triadimefon | $C_{14}H_{16}ClN_3O_2$ | 9.68 | Positive | 294.1004 | 197.07277 | 141.01017 | 126.99452 | 129.01017 | |
| Triadimenol | $C_{14}H_{18}ClN_3O_2$ | 9.79 | Positive | 296.116 | 70.03997 | 99.08044 | 227.08333 | | |
| Tridemorph | $C_{19}H_{39}NO$ | 10.27 | Positive | 298.3104 | 98.09643 | 130.12264 | 116.10699 | 71.08553 | 57.06988 |
| Trifloxystrobin | $C_{20}H_{19}F_3N_2O_4$ | 10.59 | Positive | 409.137 | 186.05251 | 145.02596 | 116.04948 | 206.08117 | 146.06004 |
| Triticonazole | $C_{17}H_{20}ClN_3O$ | 9.87 | Positive | 318.1368 | 70.03997 | 191.0622 | 125.01525 | | |
| Acetochlor | $C_{14}H_{20}ClNO_2$ | 10 | Positive | 270.1255 | 238.09932 | 162.12773 | 148.11208 | 224.08367 | 59.04914 |
| Alachlor | $C_{14}H_{20}ClNO_2$ | 11.01 | Positive | 270.1255 | 238.09932 | 162.12773 | 90.0105 | 220.08875 | 76.97887 |
| Allidochlor | $C_8H_{12}ClNO$ | 7.66 | Positive | 174.068 | 98.09643 | 106.00542 | 81.06988 | 79.05423 | 105.06988 |
| Butachlor | $C_{17}H_{26}ClNO_2$ | 10.71 | Positive | 312.1725 | 252.11497 | 176.14338 | 147.10425 | 118.06513 | |
| Butralin | $C_{14}H_{21}N_3O_4$ | 11.29 | Positive | 296.1605 | 240.09788 | 222.08732 | 208.07167 | | |
| Chlordimeform | $C_{10}H_{13}ClN_2$ | 6.11 | Positive | 197.084 | 117.0573 | 125.01525 | 152.02615 | 89.03858 | |
| Dazomet | $C_5H_{10}N_2S_2$ | 4.49 | Positive | 163.0358 | 119.99362 | 90.0372 | 95.04919 | 135.04414 | 133.02849 |
| Dinitramine | $C_{11}H_{13}F_3N_4O_4$ | 10.54 | Positive | 323.0962 | 305.0856 | 247.04374 | 215.06648 | 261.05939 | |
| Diphenylamine | $C_{12}H_{11}N$ | 9.99 | Positive | 170.0964 | 93.05785 | | | | |
| Dithiopyr | $C_{15}H_{16}F_5NO_2S_2$ | 10.73 | Positive | 402.0615 | 354.05817 | 271.99922 | 296.03554 | 312.01122 | 360.01459 |
| Fenoxanil | $C_{15}H_{18}Cl_2N_2O_2$ | 10.1 | Positive | 329.0818 | 302.07091 | 86.09643 | 188.98685 | 141.11482 | |
| Florasulam | $C_{12}H_8F_3N_5O_3S$ | 7.49 | Positive | 360.0373 | 129.03846 | 191.99265 | 109.03278 | | |
| Flumetsulam | $C_{12}H_9F_2N_5O_2S$ | 6.66 | Positive | 326.0518 | 129.0384572 | 144.02555 | 191.992532 | | |
| Haloxyfop-methyl | $C_{16}H_{13}ClF_3NO_4$ | 10.56 | Positive | 376.0558 | 316.03467 | 272.00845 | 91.05423 | 288.08936 | 119.04914 |
| Hexazinone | $C_{12}H_{20}N_4O_2$ | 8.17 | Positive | 253.1659 | 171.08765 | 71.06037 | 85.07602 | | |
| Isopropalin | $C_{15}H_{23}N_3O_4$ | 11.38 | Positive | 310.1761 | 226.08223 | 268.12918 | 250.11862 | | |
| Isoprothiolane | $C_{12}H_{18}O_4S_2$ | 9.61 | Positive | 291.0719 | 188.96746 | 144.97763 | 231.01441 | 172.97255 | 84.97426 |
| Isoxaben | $C_{18}H_{24}N_2O_4$ | 9.55 | Positive | 333.809 | 165.05462 | 122.03636 | 150.03115 | 107.01276 | |
| Metazachlor | $C_{14}H_{16}ClN_3O$ | 8.87 | Positive | 278.1055 | 134.09643 | 210.06802 | 105.06988 | 79.05423 | |
| Metolachlor | $C_{15}H_{22}ClNO_2$ | 10 | Positive | 284.412 | 252.11497 | 176.14338 | 134.09643 | 73.06479 | |
| Metosulam | $C_{14}H_{13}Cl_2N_5O_4S$ | 8.33 | Positive | 418.0138 | 174.99501 | 140.02615 | 173.98718 | 189.9820958 | |

TABLE 2-continued

Names of the pesticides, molecular formulas of the pesticides, accurate masses of the pesticides and accurate masses of characteristic ion fragments

| Name | Molecular formulas | Retention times | Scan mode | Parent ion | Characteristic ion fragments 1 | 2 | 3 | 4 | 5 |
|---|---|---|---|---|---|---|---|---|---|
| Metamitron | $C_{10}H_{10}N_4O$ | 6.6 | Positive | 203.0927 | 104.04948 | 175.09782 | 79.05423 | | |
| Norflurazon | $C_{12}H_9ClF_3N_3O$ | 9.01 | Positive | 304.0459 | 284.03967 | 160.03686 | 87.99483 | 264.03344 | 140.03063 |
| Ofurace | $C_{14}H_{16}ClNO_3$ | 8.2 | Positive | 282.0891 | 254.09423 | 236.08367 | 160.11208 | 224.08367 | 178.12264 |
| Picolinafen | $C_{19}H_{12}F_4N_2O_2$ | 10.99 | Positive | 377.0908 | 238.04742 | 256.05807 | 359.0802 | 145.02596 | |
| Pretilachlor | $C_{17}H_{26}ClNO_2$ | 10.71 | Positive | 312.1725 | 252.11497 | 176.14338 | | | |
| Propachlor | $C_{11}H_{14}ClNO$ | 8.93 | Positive | 212.0837 | 170.03672 | 94.06513 | 106.06513 | 152.02615 | |
| Propanil | $C_9H_9Cl_2NO$ | 9.58 | Positive | 218.0134 | 161.98718 | 127.01833 | | | |
| Propisochlor | $C_{15}H_{22}ClNO_2$ | 10 | Positive | 284.1412 | 212.08367 | 176.14338 | 252.11497 | 224.12005 | 73.06479 |
| Pyrazoxyfen | $C_{20}H_{16}Cl_2N_2O_3$ | 10.26 | Positive | 403.0611 | 91.05423 | 105.03349 | 119.04914 | 157.06091 | 285.01921 |
| Pyrifenox | $C_{14}H_{12}Cl_2N_2O$ | 9.7 | Positive | 295.0399 | 93.0573 | 263.01373 | 67.04165 | | |
| Pyroquilon | $C_{11}H_{11}NO$ | 8.13 | Positive | 174.0913 | 132.08078 | 117.0573 | 105.06988 | 120.08078 | 130.06513 |
| Tepraloxydim | $C_{17}H_{24}ClNO_4$ | 9.8 | Positive | 342.1467 | 250.14377 | 166.08626 | 98.06004 | 222.14886 | |
| Thiazopyr | $C_{16}H_{17}F_5N_2O_2S$ | 10.22 | Positive | 397.1004 | 377.09414 | 335.04719 | 61.01065 | 303.02093 | 317.09065 |
| Tralkoxydim | $C_{20}H_{27}NO_3$ | 11.07 | Positive | 330.2064 | 138.05495 | 284.16451 | 140.0706 | 164.0706 | 267.16177 |
| Allethrin | $C_{19}H_{26}O_3$ | 10.93 | Positive | 303.1955 | 123.11683 | 135.08044 | 107.08553 | 93.06988 | 169.12231 |
| Anilofos | $C_{13}H_{19}ClNO_3PS_2$ | 10.28 | Positive | 368.0305 | 170.96978 | 198.9647 | 124.98206 | | |
| Aspon | $C_{12}H_{28}O_5P_2S_2$ | 11.23 | Positive | 379.0926 | 210.90481 | 114.96156 | 252.95176 | 294.99871 | 138.99771 |
| Bromfenvinphos-ethyl | $C_{12}H_{14}BrCl_2O_4P$ | 10.37 | Positive | 402.9263 | 98.98417 | 169.96846 | 155.04695 | 127.01565 | 248.88679 |
| Cadusafos | $C_{10}H_{23}O_2PS_2$ | 10.57 | Positive | 271.095 | 158.96978 | 130.93848 | 215.03238 | | |
| Chlorpyrifos | $C_9H_{11}Cl_3NO_3PS$ | 11.12 | Positive | 349.9336 | 197.92747 | 114.96142 | 293.87096 | 321.90226 | 171.02393 |
| Coumaphos | $C_{14}H_{16}ClO_5PS$ | 10.39 | Positive | 363.0217 | 226.99263 | 306.95913 | 334.99043 | 288.94857 | 211.01565 |
| Crufomate | $C_{12}H_{19}ClNO_3P$ | 10.06 | Positive | 292.0864 | 126.03146 | 236.02378 | 260.06017 | 57.06988 | |
| Cycloate | $C_{11}H_{21}NOS$ | 10.64 | Positive | 216.1417 | 83.08553 | 154.12264 | 134.06341 | 72.04439 | 63.0263 |
| Cyphenothrin | $C_{24}H_{25}NO_3$ | 11.3 | Positive | 376.1907 | 151.11174 | 123.11683 | 181.06479 | 208.07569 | 81.06988 |
| DEF(Tribufos) | $C_{12}H_{27}OPS_3$ | 11.4 | Positive | 315.1034 | 168.99052 | 112.92792 | 259.04084 | 225.05312 | |
| Demeton S-methyl | $C_6H_{15}O_3PS_2$ | 8.26 | Positive | 231.0273 | 89.04195 | 61.01065 | 101.02332 | 114.96133 | 142.99263 |
| Demeton S-sulfone | $C_6H_{15}O_5PS_2$ | 7.15 | Positive | 263.0171 | 98.98417 | 234.98583 | 140.97698 | 95.01613 | 127.01547 |
| Dichlorvos | $C_4H_7Cl_2O_4P$ | 8.13 | Positive | 220.9532 | 127.0155 | 144.98173 | 112.99982 | 78.99409 | |
| Ditalimfos | $C_{12}H_{14}NO_4PS$ | 9.95 | Positive | 300.0454 | 148.0393 | 243.98279 | 272.01409 | 130.02888 | 114.96144 |
| EPTC(eptam) | $C_9H_{19}NOS$ | 10.19 | Positive | 190.126 | 128.10699 | 86.06004 | 162.13118 | | |
| Ethion | $C_9H_{22}O_4P_2S_4$ | 11 | Positive | 384.9949 | 142.93848 | 170.96978 | 114.96151 | 199.00108 | |
| Etrimfos | $C_{10}H_{17}N_2O_4PS$ | 10.3 | Positive | 293.0719 | 265.04064 | 142.99263 | 233.01443 | | |
| Famphur | $C_{10}H_{16}NO_5PS_2$ | 8.84 | Positive | 326.028 | 217.00832 | 280.97018 | 142.99263 | 93.00999 | |
| Fenamiphossulfone | $C_{13}H_{22}NO_5PS$ | 8.34 | Positive | 336.1029 | 118.04732 | 266.02466 | 108.05706 | 308.07161 | 139.02121 |
| Fenamiphossulfoxide | $C_{13}H_{22}NO_4PS$ | 8.21 | Positive | 320.108 | 171.0474268 | 250.0297416 | 292.07669 | 154.04469 | |
| Fensulfothion | $C_{11}H_{17}O_4PS_2$ | 8.93 | Positive | 309.0379 | 114.96133 | 171.02393 | 142.99263 | 247.02221 | |
| Fenthion | $C_{10}H_{15}O_3PS_2$ | 9.53 | Positive | 279.0273 | 231.02405 | 149.02347 | 216.00055 | 153.03702 | |
| Fenthionsulfone | $C_{10}H_{15}O_5PS_2$ | 8.59 | Positive | 311.0171 | 142.99269 | 127.01549 | 78.99438 | 200.00557 | |
| Fenthionsulfoxide | $C_{10}H_{15}O_4PS_2$ | 8.4 | Positive | 295.0222 | 127.01564 | 279.99902 | 278.01947 | 142.99263 | 200.00554 |
| Heptenophos | $C_9H_{12}ClO_4P$ | 9.04 | Positive | 251.0234 | 127.01547 | 125.01525 | 89.03858 | | |
| Iprobenfos | $C_{13}H_{21}O_3PS$ | 10.13 | Positive | 289.1022 | 91.05423 | 205.00828 | 65.03858 | | |
| Isazophos | $C_9H_{17}ClN_3O_3PS$ | 9.77 | Positive | 314.049 | 162.06619 | 114.9615 | 119.06069 | 178.04334 | |
| Isocarbamid | $C_8H_{15}N_3O_2$ | 7.12 | Positive | 186.1237 | 87.05529 | 130.0611 | | | |
| Malathion | $C_{10}H_{19}O_6PS_2$ | 9.65 | Positive | 331.0433 | 99.00764 | 127.03898 | 142.99266 | | |
| Molinate | $C_9H_{17}NOS$ | 9.76 | Positive | 188.1104 | 126.09134 | 83.08553 | 98.09643 | | |
| Pebulate | $C_{10}H_{21}NOS$ | 10.57 | Positive | 204.1417 | 162.09471 | 128.10699 | 72.04439 | 57.06988 | 106.03211 |
| Phenthoate | $C_{12}H_{17}O_4PS_2$ | 10.19 | Positive | 321.0379 | 135.04406 | 107.04914 | 163.07536 | 91.05423 | 79.05423 |

TABLE 2-continued

Names of the pesticides, molecular formulas of the pesticides, accurate masses of the pesticides and accurate masses of characteristic ion fragments

| Name | Molecular formulas | Retention times | Scan mode | Parent ion | Characteristic ion fragments 1 | 2 | 3 | 4 | 5 |
|---|---|---|---|---|---|---|---|---|---|
| Phorate | $C_7H_{17}O_2PS_3$ | 10.54 | Positive | 261.0201 | 75.0263 | 114.9614 | 142.93848 | | |
| Phosalone | $C_{12}H_{15}ClNO_4PS_2$ | 10.51 | Positive | 367.9941 | 182.00033 | 139.00595 | 138.0105 | 114.94149 | 130.04018 |
| Phosphamidon | $C_{10}H_{19}ClNO_5P$ | 7.7 | Positive | 300.0762 | 127.01547 | 174.06802 | 100.07569 | 226.98706 | |
| Phoxim | $C_{12}H_{15}N_2O_3PS$ | 10.47 | Positive | 299.0614 | 129.04472 | 95.04914 | 105.04472 | 215.98807 | 114.96127 |
| Piperophos | $C_{14}H_{28}NO_3PS_2$ | 10.6 | Positive | 354.1321 | 255.0273 | 170.9334 | 142.93848 | 212.98035 | |
| Pirimiphos-methyl | $C_{11}H_{20}N_3O_3PS$ | 10.43 | Positive | 306.1036 | 108.05562 | 164.11822 | 142.99263 | 136.08692 | 67.02907 |
| Profenophos | $C_{11}H_{15}BrClO_3PS$ | 10.8 | Positive | 372.9424 | 302.86417 | 114.9615 | 344.91112 | 143.9795 | 128.00234 |
| Propetamphos | $C_{10}H_{20}NO_4PS$ | 9.75 | Positive | 282.0923 | 138.0137 | 156.02426 | 194.98754 | 222.03483 | |
| Pyraclofos | $C_{14}H_{18}ClN_2O_3PS$ | 10.44 | Positive | 361.0537 | 256.98773 | 138.01042 | 140.02646 | | |
| Pyrazophos | $C_{14}H_{20}N_3O_5PS$ | 10.47 | Positive | 374.0934 | 228.08737 | 238.0645 | 346.0621 | 194.05602 | |
| Pyridaphenthion | $C_{14}H_{17}N_2O_4PS$ | 9.72 | Positive | 341.0719 | 189.06585 | 313.04064 | 92.04948 | 285.00934 | 114.96127 |
| Quinalphos | $C_{12}H_{15}N_2O_3PS$ | 10.28 | Positive | 299.0614 | 147.0552 | 163.03245 | 114.96133 | 242.99878 | 271.03008 |
| Resmethrin | $C_{22}H_{26}O_3$ | 11.48 | Positive | 339.1955 | 171.08044 | 143.08553 | 91.05423 | 128.06206 | 293.18999 |
| Tebupirimphos | $C_{13}H_{23}N_2O_3PS$ | 10.93 | Positive | 319.124 | 153.10224 | 277.07703 | 231.03516 | 249.04573 | |
| Terbufos | $C_9H_{21}O_2PS_3$ | 10.92 | Positive | 289.0514 | 57.06988 | 103.0576 | 187.00108 | 158.96978 | 130.93848 |
| Terbufossulfone | $C_9H_{21}O_4PS_3$ | 9.35 | Positive | 321.0412 | 114.96133 | 171.02393 | 142.99263 | 128.97698 | |
| Tetrachlorvinphos | $C_{10}H_9C_{14}O_4P$ | 10.11 | Positive | 364.9065 | 127.01556 | 238.89834 | 203.92948 | | |
| Tolclofos-methyl | $C_9H_{11}Cl_2O_3PS$ | 10.59 | Positive | 300.9616 | 142.99263 | 286.94598 | 174.97119 | 127.01548 | 78.99434 |
| Triazophos | $C_{12}H_{16}N_3O_3PS$ | 9.79 | Positive | 314.0723 | 162.06619 | 119.06037 | 114.96133 | | |
| Trietazine | $C_9H_{16}ClN_5$ | 9.91 | Positive | 230.1167 | 99.09167 | 132.0323 | 202.0854 | 104.001 | 71.06037 |
| Vernolate | $C_{10}H_{21}NOS$ | 10.57 | Positive | 204.1417 | 128.10699 | 86.06004 | | | |
| Chloridazon | $C_{10}H_8ClN_3O$ | 6.8 | Positive | 222.0429 | 104.04948 | 92.04948 | 65.03858 | 128.98502 | 146.01157 |
| Flumiclorac-pentyl | $C_{21}H_{23}ClFNO_5$ | 10.83 | Positive | 424.1322 | 308.04843 | 326.05899 | 107.04914 | 135.04454 | 3540539 |
| Imazamethabenz-methyl | $C_{16}H_{20}N_2O_3$ | 8.11 | Positive | 289.1547 | 144.04439 | 86.09643 | 161.07094 | 229.13354 | 257.12845 |
| Acibenzolar S-methyl | $C_8H_6N_2OS_2$ | 9.7 | Positive | 210.9994 | 136.00897 | 167.96981 | | | |
| Butocarboxim | $C_7H_{14}N_2O_2S$ | 7.27 | Positive | 191.0849 | 75.0263 | 116.05285 | | | |
| Piperonylbutoxide | $C_{19}H_{30}O_5$ | 11.02 | Positive | 339.2166 | 177.09101 | 119.08553 | 149.05971 | 147.08044 | |
| Propham | $C_{10}H_{13}NO_2$ | 9.12 | Positive | 180.1019 | 120.04439 | 138.05495 | 92.05006 | | |
| Fludioxonil | $C_{12}H_6F_2N_2O_2$ | 9.4 | Positive | 249.047 | 180.03282 | 126.03477 | 169.0406 | 151.03003 | |
| Hexaflumuron | $C_{16}H_8Cl_2F_6N_2O_3$ | 10.7 | Positive | 460.9889 | 158.0412 | 141.01465 | | | |
| Novaluron | $C_{17}H_9ClF_8N_2O_4$ | 10.7 | Positive | 493.0196 | 158.0412 | 141.01456 | 310.0064 | | |
| Cyclanilide | $C_{11}H_9Cl_2NO_3$ | 9.87 | Positive | 274.0032 | 113.02381 | | | | |
| Nitralin | $C_{13}H_{19}N_3O_6S$ | 9.95 | Positive | 346.1067 | 141.11482 | | | | |
| Terbacil | $C_9H_{13}ClN_2O_2$ | 8.39 | Positive | 217.0738 | 161.01123 | 143.98468 | 163.0082816 | 145.9817325 | |
| Chlorthiophos | $C_{11}H_{15}Cl_2O_3PS_2$ | 11.64 | Positive | 360.965 | 304.9024 | 332.9337 | 224.93607 | 191.95615 | |
| Cypermethrin | $C_{22}H_{19}Cl_2NO_3$ | 11.94 | Positive | 416.0815 | 191.0025 | 127.0309 | 91.05423 | 163.00758 | 181.06479 |
| Demeton-S (Disulfotonoxon) | $C_8H_{19}O_3PS_2$ | 9 | Positive | 259.0586 | 89.04195 | 61.01065 | | | |
| Phoratesulfoxide | $C_7H_{17}O_4PS_2$ | 6.57 | Positive | 261.0379 | 128.97698 | 171.02393 | 243.0273 | | |
| Thiometon | $C_6H_{15}O_2PS_3$ | 8.43 | Positive | 247.0045 | 61.01065 | 89.04195 | | | |
| Imazaquin | $C_{17}H_{17}N_3O_3$ | 7.55 | Positive | 312.1343 | 199.0502 | 86.09643 | 267.1128 | 252.07675 | 69.06988 |
| Chlorpyrifos-methyl | $C_7H_7Cl_3NO_3PS$ | 10.7 | Positive | 321.9023 | 142.99263 | 289.87605 | 78.99441 | 127.01556 | |
| Benzoylprop-ethyl | $C_{20}H_{22}ClNO_5$ | 10.19 | Positive | 392.1259 | 105.03349 | 95.04915 | 77.03858 | | |
| Thifensulfuron methyl | $C_{12}H_{13}N_5O_6S_2$ | 8.17 | Positive | 388.038001 | 167.05635 | 141.07709 | 222.97294 | | |
| Chlorotoluron | $C_{10}H_{13}ClN_2O$ | 8.88 | Positive | 213.0789173 | 72.04439 | 140.02615 | 168.02107 | 125.01525 | 94.0652 |
| Trimethacarb | $C_{11}H_{15}NO_2$ | 9.04 | Positive | 194.1175553 | 137.09609 | 122.07262 | | | |
| Clomazone | $C_{12}H_{14}ClNO_2$ | 9.33 | Positive | 240.078583 | 125.01525 | 127.01233 | | | |

TABLE 2-continued

Names of the pesticides, molecular formulas of the pesticides, accurate masses of the pesticides and accurate masses of characteristic ion fragments

| Name | Molecular formulas | Retention times | Scan mode | Parent ion | Characteristic ion fragments 1 | 2 | 3 | 4 | 5 |
|---|---|---|---|---|---|---|---|---|---|
| Bromuconazole(cis-) | $C_{13}H_{12}BrCl_2N_3O$ | 9.85 | Positive | 375.9613566 | 158.97628 | 172.95555 | | | |
| Mecarbam | $C_{10}H_{20}NO_5PS_2$ | 9.98 | Positive | 330.0593271 | 142.93848 | 226.996 | 199.00108 | 170.96978 | |
| Propaquizafop | $C_{22}H_{22}ClN_3O_5$ | 10.95 | Positive | 444.132075 | 100.07569 | 299.05818 | 371.07919 | 255.03197 | 70.06527 |
| Aldicarb-NH4 | $C_7H_{14}N_2O_2S$ | 7.5 | Positive | 208.11142 | 89.04195 | 116.05285 | 70.06513 | | |
| Aldoxycarb(Aldicarb Sulfone)-NH4 | $C_7H_{14}N_2O_4S$ | 4.67 | Positive | 240.10125 | 86.06004 | 148.04268 | 76.03941 | 166.05324 | 223.0747 |
| Atraton | $C_9H_{17}N_5O$ | 7.71 | Positive | 212.15059 | 170.10364 | 100.05054 | 114.06619 | 142.07234 | 128.08184 |
| Atrazine-Desethyl | $C_6H_{10}ClN_5$ | 7 | Positive | 188.06975 | 146.0228 | 104.001 | 110.04612 | | |
| Azinphos-Ethyl | $C_{12}H_{16}N_3O_3PS_2$ | 9.8 | Positive | 346.04435 | 137.00556 | 132.04439 | 232.94867 | 95.04945 | 114.96133 |
| Aziprotryne | $C_7H_{11}N_7S$ | 9.59 | Positive | 226.08694 | 156.03384 | 125.08217 | 114.01204 | 89.0168 | 198.08079 |
| Benzofenap | $C_{22}H_{20}Cl_2N_2O_3$ | 10.58 | Positive | 431.09237 | 105.06988 | 157.06077 | 119.04914 | 133.06479 | |
| Bioallethrin | $C_{19}H_{26}O_3$ | 10.75 | Positive | 303.19547 | 135.08044 | 169.12231 | 151.11174 | 123.11683 | 107.08553 |
| Bioresmethrin | $C_{22}H_{26}O_3$ | 11.31 | Positive | 339.19547 | 171.08044 | 143.08553 | 128.06205 | 105.03349 | 225.12739 |
| Bolstar | $C_{12}H_{19}O_2PS_3$ | 10.88 | Positive | 323.03576 | 139.02121 | 154.9715 | 218.96978 | 200.95922 | 171.97424 |
| Bromacil | $C_9H_{13}BrN_2O_2$ | 8.11 | Positive | 261.02332 | 204.96072 | 187.93417 | 161.9549 | 143.94434 | 98.04746 |
| Brompyrazon | $C_{10}H_8BrN_3O$ | 6.91 | Positive | 265.99235 | 92.04948 | 104.04948 | 131.94434 | 172.9345 | |
| Chlorimuron Ethyl | $C_{15}H_{15}ClN_4O_6S$ | 9.5 | Positive | 415.04736 | 186.00599 | 213.02092 | 121.02841 | 83.02448 | |
| Chlormequat Chloride | $C_5H_{12}ClN$ | 0.8 | Positive | 122.0731 | 86.09643 | 94.0418 | 106.0418 | | |
| Chlorphoxim | $C_{12}H_{14}ClN_2O_3PS$ | 10.27 | Positive | 333.0224 | 114.96133 | 163.00527 | 111.04406 | 139.00558 | 86.9996 |
| Chlorsulfuron | $C_{12}H_{12}ClN_5O_4S$ | 8.38 | Positive | 358.03713 | 141.07709 | 167.05635 | 100.05054 | 129.01017 | |
| Cinidon-Ethyl | $C_{19}H_{17}Cl_2NO_4$ | 10.66 | Positive | 394.06074 | 348.01888 | 366.02944 | 107.04914 | 135.04406 | 239.96087 |
| Cinosulfuron | $C_{15}H_{19}N_5O_7S$ | 7.85 | Positive | 414.1078 | 183.05127 | 157.072 | 121.02841 | 215.03657 | |
| Coumatetralyl | $C_{19}H_{16}O_3$ | 9.79 | Positive | 293.11722 | 175.03897 | 131.08553 | 107.04914 | 163.03897 | 215.07027 |
| Crimidine | $C_7H_{10}ClN_3$ | 6.98 | Positive | 172.0636 | 136.08692 | 109.07602 | 95.06037 | 119.06037 | |
| Cyclosulfamuron | $C_{17}H_{19}N_5O_6S$ | 9.75 | Positive | 422.11288 | 261.02813 | 139.03763 | 279.03869 | 236.03288 | 199.08257 |
| Cythioate | $C_8H_{12}NO_5PS_2$ | 7.66 | Positive | 297.99673 | 142.99263 | 217.00828 | 283.98108 | 124.02155 | 108.04439 |
| Deet(Diethyltoluamide) | $C_{12}H_{17}NO$ | 8.82 | Positive | 192.13829 | 119.04914 | 109.06479 | 100.07569 | 164.10699 | |
| Desmetryne | $C_8H_{15}N_5S$ | 8.16 | Positive | 214.11209 | 172.06514 | 82.03997 | 124.06117 | 116.02769 | 99.06652 |
| Dialifos | $C_{14}H_{17}ClNO_4PS_2$ | 10.4 | Positive | 394.00979 | 208.01598 | 181.00504 | 158.96978 | 130.93848 | 114.96133 |
| Diallate(Total) | $C_{10}H_{17}Cl_2NOS$ | 10.55 | Positive | 270.04807 | 108.96063 | 128.10699 | 86.06004 | 228.00112 | 142.94835 |
| Dichlofenthion | $C_{10}H_{13}C_{12}O_3PS$ | 9.28 | Positive | 314.97728 | 258.91468 | 286.94598 | 114.96136 | 222.93801 | 162.9712 |
| Dichlofluanid | $C_9H_{11}Ch_2FN_2O_2S_2$ | 9.8 | Positive | 332.96958 | 223.94983 | 123.01379 | 188.98053 | 153.0043 | |
| Dichlorobenzamide | $C_6H_3CONH_2Cl_2$ | 5.2 | Positive | 189.9821 | 172.95555 | 108.98395 | 146.97628 | 120.96063 | 128.00234 |
| Dicyclohexyl Phthalate | $C_{20}H_{26}O_4$ | 11.1 | Positive | 331.19039 | 167.03389 | 149.02332 | 249.11214 | 121.02841 | |
| Dimefox | $C_4H_{12}FN_2OP$ | 6.06 | Positive | 155.0744 | 110.01656 | 135.06818 | 92.02598 | | |
| Dimethirimol | $C_{11}H_{19}N_3O$ | 7.19 | Positive | 210.16009 | 140.10699 | 98.06004 | 150.10257 | 165.10224 | 122.09643 |
| Dimethyl Phthalate | $C_{10}H_{10}O_4$ | 7.9 | Positive | 195.06519 | 163.03897 | 135.04406 | 105.03349 | | |
| Dioxabenzofos | $C_8H_9O_3PS$ | 8.93 | Positive | 217.00828 | 107.04914 | 123.0263 | 137.04195 | 154.9715 | 186.99771 |
| Disulfoton Sulfone | $C_8H_{19}O_4PS_3$ | 8.78 | Positive | 307.02558 | 114.96133 | 171.02393 | 260.98372 | 142.99263 | 232.95242 |
| Dmst | $C_9H_{14}N_2O_2S$ | 8.32 | Positive | 215.08487 | 106.06513 | 136.0995 | 151.12298 | | |
| Dodine | $C_{13}H_{29}N_3$ | 10.43 | Positive | 228.24342 | 186.22163 | 85.10118 | 57.07061 | 71.0861 | |
| Emamectin B1A Benzoate | $C_{49}H_{75}NO_{13}$ | 10.77 | Positive | 886.53112 | 158.11756 | 82.06513 | 126.09134 | 302.1962 | |
| Emamectin B1B Benzoate | $C_{48}H_{73}NO_{13}$ | 10.6 | Positive | 872.51547 | 158.11756 | 82.06513 | 126.09134 | 302.1962 | |
| Etaconazole | $C_{14}H_{15}Cl_2N_3O_2$ | 9.8 | Positive | 328.06141 | 158.97628 | 204.98176 | 186.9712 | 245.01306 | 259.02871 |
| Ethiofencarb Sulfoxide | $C_{11}H_{15}NO_3S$ | 6.33 | Positive | 242.08454 | 107.0491414 | 185.0630769 | 164.0706 | 95.04914 | |
| Ethoprophos (Ethoprop) | $C_8H_{19}O_2PS_2$ | 9.84 | Positive | 243.06368 | 172.98543 | 130.93848 | 215.03238 | 201.01673 | 138.99771 |
| Ethoxysulfuron | $C_{15}H_{18}N_4O_7S$ | 9.56 | Positive | 399.0969 | 279.03938 | 236.03288 | 182.05602 | 139.03763 | 109.02841 |

TABLE 2-continued

| Names of the pesticides, molecular formulas of the pesticides, accurate masses of the pesticides and accurate masses of characteristic ion fragments | | | | | | | | | |
|---|---|---|---|---|---|---|---|---|---|
| | Molecular | Retention | Scan | Parent | Characteristic ion fragments | | | | |
| Name | formulas | times | mode | ion | 1 | 2 | 3 | 4 | 5 |
| Ethylene Thiourea | $C_3H_6N_2S$ | 1.62 | Positive | 103.03245 | 86.0059 | 57.07052 | | | |
| Fenfuram | $C_{12}H_{11}NO_2$ | 8.51 | Positive | 202.08626 | 109.02841 | 120.04439 | 184.07569 | 92.04948 | |
| Fentrazamide | $C_{16}H_{20}ClN_5O_2$ | 10.15 | Positive | 350.13783 | 197.12845 | 154.12264 | 115.0502 | | |
| Flamprop-Isopropyl | $C_{19}H_{19}ClFNO_3$ | 10.19 | Positive | 364.11103 | 105.03349 | 172.03189 | 276.05811 | 304.05302 | |
| Flamprop-Methyl | $C_{17}H_{15}ClFNO_3$ | 9.62 | Positive | 336.07973 | 105.03349 | 95.04963 | 276.0586 | 304.05351 | |
| Fluazifop-Butyl | $C_{19}H_{20}F_3NO_4$ | 10.62 | Positive | 384.14172 | 282.0725 | 328.07798 | 238.04628 | 164.03177 | 119.04914 |
| Fluazuron | $C_{20}H_{10}C_{12}F_5N_3O_3$ | 10.82 | Positive | 506.00921 | 158.0412 | 348.97415 | 141.01445 | 123.99485 | |
| Flubenzimine | $C_{17}H_{10}F_6N_4S$ | 10.61 | Positive | 417.06031 | 187.04776 | 167.04153 | 136.02135 | 95.04963 | |
| Fluorochloridon | $C_{12}H_{10}Cl_2F_3NO$ | 9.6 | Positive | 312.01643 | 292.0102 | 212.06816 | 240.06307 | 172.03686 | |
| Fluridone | $C_{19}H_{14}F_3NO$ | 9.12 | Positive | 330.11003 | 310.1038 | 290.09757 | 242.09643 | 115.05423 | |
| Fluthiacet-Methyl | $C_{15}H_{15}ClFN_3O_3S_2$ | 10.13 | Positive | 404.03002 | 344.00889 | 273.99721 | 214.98393 | 309.03849 | |
| Fonofos | $C_{10}H_{15}OPS_2$ | 9.31 | Positive | 247.03747 | 137.01845 | 108.98715 | 200.9956 | 80.95585 | 126.9977 |
| Furmecyclox | $C_{14}H_{21}NO_3$ | 10.13 | Positive | 252.15942 | 170.08117 | 110.06004 | 138.05496 | 97.06479 | |
| Guthion(Azinphos-Methyl) | $C_{10}H_{12}N_3O_3PS_2$ | 9.1 | Positive | 318.01305 | 142.99278 | 132.04439 | 260.9806 | 104.04948 | |
| Haloxyfop-2-Etotyl | $C_{19}H_{19}ClF_3NO_5$ | 10.57 | Positive | 434.09766 | 316.03418 | 272.00797 | 298.02362 | 388.0558 | |
| Imazapic | $C_{14}H_{17}N_3O_3$ | 7.05 | Positive | 276.13427 | 163.0502 | 216.07675 | 231.1128 | 188.08184 | |
| Imazethapyr | $C_{15}H_{19}N_3O_3$ | 7.73 | Positive | 290.14992 | 177.06585 | 245.12845 | 230.0924 | 159.05529 | |
| Isofenphos | $C_{15}H_{24}NO_4PS$ | 10.29 | Positive | 346.12364 | 121.02841 | 216.97189 | 245.00319 | 137.00587 | |
| Isomethiozin | $C_{12}H_{20}N_4OS$ | 10.26 | Positive | 269.14306 | 200.08521 | 172.09029 | 116.02769 | 130.04334 | |
| Isouron | $C_{10}H_{17}N_3O_2$ | 8.24 | Positive | 212.13935 | 167.0815 | 128.08184 | 140.04545 | 111.0189 | |
| Kadethrin-NH4 | $C_{23}H_{24}O_4S$ | 10.54 | Positive | 414.17336 | 171.08044 | 143.08553 | 128.06205 | 283.07873 | |
| Kresoxim-Methyl | $C_{18}H_{19}NO_4$ | 10.08 | Positive | 314.13868 | 222.09134 | 235.07536 | 116.04948 | 194.09643 | |
| Malaoxon | $C_{10}H_{19}O_7PS$ | 8.16 | Positive | 315.06619 | 99.00767 | 127.03897 | 142.99263 | 113.02332 | |
| Mefenpyr-Diethyl | $C_{16}H_{18}Cl_2N_2O_4$ | 10.2 | Positive | 373.07164 | 327.0297742 | 159.9715311 | 271.00356 | 132.96063 | |
| Mephosfolan | $C_8H_{16}NO_3PS_2$ | 7.96 | Positive | 270.0382 | 167.98788 | 139.95658 | 75.0263 | 242.0069 | |
| Metalaxyl-M | $C_{15}H_{21}NO_4$ | 8.77 | Positive | 280.15433 | 192.13829 | 160.11208 | 220.13321 | 248.12812 | |
| Methfuroxam | $C_{14}H_{15}NO_2$ | 9.08 | Positive | 230.11756 | 137.05971 | 111.08044 | 120.04439 | | |
| MethylParaoxon | $C_8H_{10}NO_6P$ | 7.73 | Positive | 248.03185 | 202.03895 | 127.01556 | 90.04646 | 234.02881 | |
| Monalide/dimethachlor | $C_{13}H_{18}ClNO$ | 9.98 | Positive | 240.11497 | 224.08367 | 148.11208 | 132.08078 | 105.06988 | |
| Monuron | $C_9H_{11}ClN_2O$ | 8.02 | Positive | 199.06327 | 72.04439 | 126.010502 | 154.005417 | 126.010502 | |
| Naptalam | $C_{18}H_{13}NO_3$ | 8.18 | Positive | 292.09682 | 149.02332 | 144.08078 | 121.02841 | 256.07559 | |
| Nicotine | $C_{10}H_{14}N_2$ | 2.18 | Positive | 163.12298 | 132.08078 | 130.06513 | 117.0573008 | 106.06513 | |
| Oxycarboxin | $C_{12}H_{13}NO_4S$ | 7.04 | Positive | 268.06381 | 175.00596 | 164.98543 | 193.01674 | 104.96409 | |
| Oxydemeton Methyl | $C_6H_{15}O_4PS_2$ | 5.33 | Positive | 247.02221 | 169.00828 | 127.0154717 | 142.99263 | 105.03686 | |
| Phorate-Sulfone | $C_7H_{17}O_4PS_3$ | 8.76 | Positive | 293.00993 | 171.02397 | 142.93848 | 114.96133 | | |
| Phosfolan | $C_7H_{14}NO_3PS_2$ | 7.45 | Positive | 256.02255 | 139.95627 | 167.98757 | 196.01918 | 227.99125 | |
| Pirimiphos-Ethyl | $C_{13}H_{24}N_3O_3PS$ | 10.73 | Positive | 334.13488 | 198.10594 | 182.12879 | 170.07481 | 114.96146 | |
| Pronamide | $C_{12}H_{11}Cl_2NO$ | 9.6 | Positive | 256.02905 | 189.9820958 | 172.9555467 | 146.97628 | | |
| Propylene Thiourea | $C_4H_8N_2S$ | 0.8 | Positive | 117.0481 | 100.02155 | 59.99025 | 71.99025 | | |
| Pyrazosulfuron-Ethyl | $C_{14}H_{18}N_6O_7S$ | 9.76 | Positive | 415.10304 | 182.05602 | 139.0502 | 157.06077 | 213.9917 | |
| Pyrethrini 1 | $C_{21}H_{28}O_3$ | 11.08 | Positive | 329.21112 | 161.09609 | 143.08553 | 105.06988 | 128.06205 | |
| Pyributicarb | $C_{18}H_{22}N_2O_2S$ | 10.84 | Positive | 331.14748 | 181.04301 | 126.05496 | 190.12264 | 151.11174 | |
| Pyriftalid | $C_{15}H_{14}N_2O_4S$ | 9.17 | Positive | 319.0747 | 139.0502 | 157.06077 | 179.01613 | 202.03211 | |
| Pyrimidifen | $C_{20}H_{28}ClN_3O_2$ | 10.77 | Positive | 378.19428 | 184.06311 | 150.10257 | 169.03964 | 130.02923 | |
| Pyrithiobac-Sodium | $C_{13}H_{11}ClN_2O_4S$ | 8.94 | Positive | 327.02008 | 309.00952 | 139.0502 | 203.9842 | 267.98297 | |
| Quinoclamine | $C_{10}H_6ClNO_2$ | 8.03 | Positive | 208.01598 | 172.0393 | 105.03349 | 137.01525 | 180.02107 | |
| Quizalofop-Ethyl | $C_{19}H_{17}ClN_2O_4$ | 10.69 | Positive | 373.09496 | 299.05769 | 271.06278 | 255.03148 | 181.01583 | |

TABLE 2-continued

| Names of the pesticides, molecular formulas of the pesticides, accurate masses of the pesticides and accurate masses of characteristic ion fragments | | | | | | | | | |
|---|---|---|---|---|---|---|---|---|---|
| | Molecular | Retention | Scan | Parent | Characteristic ion fragments | | | | |
| Name | formulas | times | mode | ion | 1 | 2 | 3 | 4 | 5 |
| Rabenzazole | $C_{12}H_{12}N_4$ | 8.86 | Positive | 213.11347 | 172.08692 | 186.10257 | 132.0682 | 145.07602 | |
| Simeton | $C_8H_{15}N_5O$ | 6.91 | Positive | 198.13494 | 124.08692 | 114.06619 | 100.05054 | 170.10364 | |
| Spinosad A | $C_{41}H_{65}NO_{10}$ | 10.21 | Positive | 732.46812 | 142.12264 | 98.09643 | 97.06479 | | |
| Spinosad D | $C_{42}H_{67}NO_{10}$ | 10.41 | Positive | 746.48377 | 142.12264 | 98.09643 | | | |
| Succinic Acid Di-N-Butyl Ester | $C_{12}H_{22}O_4$ | 10.12 | Positive | 231.15909 | 101.02332 | 115.03897 | 157.08592 | | |
| Sulfotepp | $C_8H_{20}O_5P_2S_2$ | 10.11 | Positive | 323.03001 | 114.96133 | 142.99263 | 171.02393 | 266.96741 | |
| Tau-Fluvalinate | $C_{26}H_{22}ClF_3N_2O_3$ | 11.31 | Positive | 503.13438 | 181.06479 | 208.07569 | 250.06 | | |
| Tepp | $C_8H_{20}O_7P_2$ | 7.82 | Positive | 291.0757 | 178.9505 | 98.98417 | 206.9818 | 235.0131 | |
| Terbucarb | $C_{17}H_{27}NO_2$ | 10.52 | Positive | 278.21146 | 109.06479 | 166.08626 | 222.14886 | | |
| Thiofanox-Sulfoxide | $C_9H_{18}N_2O_3S$ | 6.24 | Positive | 235.11109 | 104.01646 | 178.08963 | 115.09917 | 160.07906 | |
| Thionazin | $C_8H_{13}N_2O_3PS$ | 8.87 | Positive | 249.04573 | 113.0168 | 97.03964 | 192.98282 | 221.01443 | |
| Thiophanate | $C_{14}H_{18}N_4O_4S_2$ | 8.85 | Positive | 371.08422 | 151.03245 | 282.03654 | 134.07127 | | |
| Triallate | $C_{10}H_{16}ClNOS$ | 11 | Positive | 304.00909 | 142.92166 | 261.96214 | 128.10699 | | |
| Triazoxide | $C_{10}H_6ClN_5O$ | 8.87 | Positive | 248.03336 | 123.9948534 | 149.99793 | 98.9996 | 221.02246 | |
| Tributyl Phosphate | $C_{12}H_{27}O_4P$ | 10.56 | Positive | 267.17197 | 98.98417 | 155.04677 | 211.10937 | | |
| Triisobutyl Phosphate | $C_{12}H_{27}O_4P$ | 10.45 | Positive | 267.17197 | 98.98417 | 155.04677 | 211.10937 | | |
| Uniconazole | $C_{15}H_{18}ClN_3O$ | 9.94 | Positive | 292.12112 | 70.04078 | 125.01525 | | | |
| Vamidothion-Sulfone | $C_8H_{18}NO_6PS_2$ | 5.59 | Positive | 320.03859 | 178.05324 | 169.00828 | 142.99263 | 86.06004 | |
| Vegadex(Thioallate) | $C_8H_{14}ClNS_2$ | 10.08 | Positive | 224.0329 | 116.05285 | 188.05622 | 150.94375 | | |

3. Qualitative Detection Method

Under the detection conditions, the accurate mass database including name of the compounds, the molecular formula, the accurate mass, the retention time and the characteristic ion fragments is established for the determined compounds of the pesticides. Then the qualitative screening method of the compounds is carried out by using TractFinder 2.5 software. The screening parameters are shown in Table 3, and the samples that meet the set range are positive samples.

TABLE 3

| Screening parameter settings of TractFinder | |
|---|---|
| Use matrix Blank | 10 |
| Mass Tolerance | 10 ppm |
| Smoothing Point | 7 |
| Chromatogram View Width | 2.00 minutes |
| Peaks | Threshold Override: 10,000<br>S/N Ratio Threshold 50.0 |
| Retention time* (Identify) | Window override (see): 120 |
| Fragment Ions (Confirm) | Min. # of Fragments: Intensity Threshold: 1,000<br>Mass Tolerance: 10 ppm |

4. Lowest Limit for Detection

Lowest limit of the qualitative detection: the lowest limit of the qualitative detection of the method for the above 390 pesticides is 10 μg/kg.

What is claimed is:

1. A method for screening pesticide residues in medicine food homology (MFH) agricultural products comprising:

step 1, constructing a liquid chromatography-mass spectrometry database of pesticides, preparing solutions for the pesticides and using liquid chromatography and mass spectrometry to detect the solutions to obtain liquid chromatography-mass spectrograms of the solutions, wherein a detection condition of the liquid chromatography comprises:

a liquid chromatography column: a hydrophilic interaction liquid chromatography (HPLC) column, 150 millimeter (mm)×2.1 mm, a particle size of 2.6 micrometer (μm);

a mobile phase A: ammonium formate of 5 millimol per liter (mM) and a 0.1% formic acid aqueous solution;

a mobile phase B: ammonium formate of 5 mM and a 0.1% formic acid methanol solution, a column temperature: 25° C.;

a flow rate of the liquid chromatography: 0.35-0.45 milliliters per minute (mL/min);

wherein a condition of gradient elution is as follows: an initial proportion of the mobile phase A is 100%, the initial proportion of the mobile phase A gradually decreases to a first proportion of 80% within 4 minutes, the first proportion gradually decreases to a second proportion of 60% within 1.5 minutes, the second proportion gradually decreases to a third proportion of 0% within 4 minutes, following by remaining for 2.4 minutes, and then the third proportion gradually increases to the initial proportion of 100%;

wherein a detection condition of the mass spectrometry comprises:

an ion source: an electrospray ion source;

a temperature of the ion source: 325° C.;

a temperature of a heater: 350° C.;

a sheath gas flow rate: 40 atmospheres relative to vacuum (arb);

an aux gas flow rate: 10 arb;

step 2, processing a sample to obtain a processed sample, and detecting the processed sample to obtain a liquid chromatography-mass spectrogram of the processed sample;

step 3, comparing the liquid chromatography-mass spectrogram obtained from step 2 with the liquid chromatography-mass spectrograms in the liquid chromatography-mass spectrometry database obtained from step 1 individually based on parameters including a mass tolerance, a retention time, and fragment ions; and in response to a value of each of the parameters of the sample being within a predetermined range corresponding to each of the parameters, identifying the sample as a positive sample.

2. The method for screening the pesticide residues in the MFH agricultural products as claimed in claim 1, wherein the liquid chromatography-mass spectrometry database comprises: names of compounds, molecular formulas of the compounds, masses of the compounds, retention times of the compounds and masses of characteristic ion fragments.

3. The method for screening the pesticide residues in the MFH agricultural products as claimed in claim 2, wherein the pesticides in step 1 comprise at least one selected from the group consisting of acephate, acetamiprid, aminocarb, azamethiphos, benalaxyl, bendiocarb, benfuracarb, bensulide, benzoximate, bifenazate, bupirimate, butafenacil, butoxycarboxim, buturon, carpropamid, carbaryl, carbendazim, carbetamide, carbofuran, carboxin, clethodim, clothianidin, cyazofamid, cycloxydim, cyprodinil, desmedipham, dicrotophos, diethofencarb, dimethoate, dinotefuran, dioxycarb, ethiofencarb, ethirimol, ethofumesate, fenazaquin, fenhexamid, fenobucarb, fenoxycarb, fenpropidine, flufenacet, fuberidazole, furalaxyl, furathiocarb, hexythiazox, hydramethylnon, imidachloprid, indoxacarb, isoprocarb, mefenacet, mepanipyrim, mepronil, metalaxyl, methamidophos, methomyl, methoxyfenozide, m-tolyl methylcarbamate, metribuzin, napropamide, nitenpyram, nuarimol, omethoate, oxamyl, pencycuron, primicarb, propamocarb, propargite, propoxur, prosulfocarb, pyrimethanil, quinoxyfen, rotenone, spirodiclofen, tebufenozide, tebutam, temephos, thiabendazole, thiacloprid, thiamethoxam, thiobencarb, thiodicarb, thiophanate-methyl, trichlorfon, vamidothion, ametryn, atrazine, azoxystrobin, benodanil, benoxacor, bitertanol, boscalid, buprofezin, butylate, chlorfluazuron, cumyluron, cyanazine, cycluron, cyproconazole, cyromazine, diclobutrazole, diflufenican, dimepiperate, dimethametryn, dimethenamid, dimethomorph, diniconazole, diphenamid, dipropetryn, diuron, dodemorph, epoxiconazole, ethiprole, etobenzanid, fenbuconazole, fenpropathrin, fenpropimorph, fenpyroximate, fenuron, flufenoxuron, fluometuron, flurtamone, flusilazole, flutolanil, flutriafol, forchlorfenuron, imazalil, imibenconazole, isoproturon, linuron, metconazole, methabenzthiazuron, methoprotryne, metobromuron, metoxuron, monolinuron, myclobutanil, neburon, paclobutrazole, penconazole, phenmedipham, picoxystrobin, prochloraz, prometon, prometryne, propazine, propiconazole, pymetrozine, pyraclostrobin, pyriproxyfen, sebutylazine, secbumeton, simeconazole, simetryn, tebuconazole, tebuthiuron, terbuthylazine, terbumeton, terbutryne, tetraconazole, thenylchlor, triadimefon, triadimenol, tridemorph, trifloxystrobin, triticonazole, acetochlor, alachlor, allidochlor, butachlor, butralin, chlordimeform, dazomet, dinitramine, diphenylamine, dithiopyr, fenoxanil, florasulam, flumetsulam, haloxyfop-2-ethoxyethyl, hexazinone, isopropalin, isoprothiolane, isoxaben, metazachlor, metolachlor, metosulam, metamitron, norflurazon, ofurace, picolinafen, pretilachlor, propachlor, propanil, propisochlor, prosulfocarb, pyrifenox, pyroquinolone, tepraloxydim, thiazopyr, tralkoxydim, allethrin, anilofos, aspon, bromfenvinfos, cadusafos, chlorpyrifos, coumaphos, crufomate, cycloate, cyphenothrin, defoliant, demeton-S-methyl, demeton-S-methylsulphone, dichlorvos, ditalimfos, eradicane, ethion, etrimfos, famphur, fenamiphossulfone, fenamiphos metabolite, fensulfothion, fenthion, fenthionsulfone, fenthionsulfoxide, heptenephos, iprobenfos, isazofos, isocarbamid, malathion, molinate, pebulate, phenthoate, phorate, phosalone, phosphamidon, phoxim, piperophos, pirimiphos-methyl, profenofos, propetamphos, pyraclofos, pyrazophos, pyridaphenthion, quinalphos, resmethrin, tebupirimfos, terbufos, terbufos sulfone, tetrachlorvinphos, tolclofos-methyl, triazophos, trietazine, vernolate, chloridazon, flumiclorac-pentyl, imazamethabenz-methyl, benzothiadiazole, butocarboxim, piperonyl-butoxide, propham, fludioxonil, hexaflumuron, fluorourea, cyclanilide, nitralin, terbacil, chlorthiophos, cypermethrin, demeton, phorate sulfoxide, thiometon, imazaquin, chlorpyrifos-methyl, benzoylprop, thifensulfuron-methyl, chlortoluron, trimethacarb, clomazone, bromuconazole (cis), mecarbam, propaquizafop, aldicarb, aldicarb sulfoxide, atratone, deethylatrazine, azinphos-ethyl, aziprotryn, benzofenap, bioallethrin, bioresmethrin, sulprofos, bromacil, brompyrazon, chlorimuron, cycocel, chlorpoxime, chlorsulfuron, cinidon-ethyl, cinosulfuron, coumatetralyl, cyclosulfamuron, cythioate, diethyltoluamide, desmetryne, dialifos, diallate, dichlofenthion, dichlofluanid, dichlorobenzamide, dicyclohexyl phthalate, dimefox, dimethirimol, dimethyl phthalate, dioxabenzofos, disulfoton-sulfone, dimethylbenzenesulfonamide, dodine, emamectin benzoate-Bla, emamectin benzoate-B1b, etaconazole, ethiofencarb-sulfoxide, ethoprophos, ethoxysulfuron, ethylene thiourea, ofurace, fentrazamide, flamprop-isopropyl, flamprop-methyl, fluazifop-butyl, fluazuron, flubenzimine, flurochloridone, fluridone, fluthiacet, fonofos, furmecyclox, azinphos-methyl, pyrflumetocloprid, imazapic, imazethapyr, isofenphos, isomethiozin, isouron, kadethrin, kresoxim-methyl, malaoxon, mefenpyr-diethyl, mephosfolan, mefenoxam, methfuroxam, paraoxon-methyl, monalide, monuron, naptalam, nicotine, oxycarboxin, oxydemeton-methyl, phoratesulfone, phosfolan, pirimiphos-ethyl, propyzamide, propylenethiourea, pyrazosulfuron methyl, pyrethrin 1, pyributicarb, pyriftalid, pyrimidifen, pyrithiobac-sodium, quinoclamine, quizalofop, rabenzazole, simeton, pleocidin A, pleocidin D, tabatrex, sulfotepp, tau-fluvalinate, tetraethyl diphosphate, terbucarb, thiofanox sulfoxide, thionazin, thiophanate, triallate, triazoxide, tri-n-butyl phosphate, triiso-butyl phosphate, uniconazole, vamidothion sulfone and sulfallate.

4. The method for screening the pesticide residues in the MFH agricultural products as claimed in claim 1, wherein the flow rate of the liquid chromatography is 0.4 mL/min.

5. The method for screening the pesticide residues in the MFH agricultural products as claimed in claim 4, wherein a scanning range of the mass spectrometry comprises: 100-900 mass-to-charge ratios (M/Z) in a positive ion mode, or 100-700 M/Z in a negative ion mode.

6. The method for screening the pesticide residues in the MFH agricultural products as claimed in claim 5, wherein a resolution of the mass spectrometry comprises: 70000 in full mass spectrometry scanning, or 17500 in tandem mass spectrometry (MS/MS).

* * * * *